United States Patent
Rannard et al.

[11] Patent Number: 6,037,444
[45] Date of Patent: Mar. 14, 2000

[54] SELECTIVE CHEMICAL REACTIONS AND POLYMERS OF CONTROLLED ARCHITECTURE PRODUCED THEREBY

[75] Inventors: Steven Paul Rannard, Stratford-Upon-Avon; Nicola Jane Davis, Coventry, both of United Kingdom

[73] Assignee: Courtaulds Coatings (Holdings) Limited, United Kingdom

[21] Appl. No.: 09/091,493

[22] PCT Filed: Dec. 20, 1996

[86] PCT No.: PCT/GB96/03189

§ 371 Date: Jun. 18, 1998

§ 102(e) Date: Jun. 18, 1998

[87] PCT Pub. No.: WO97/23443

PCT Pub. Date: Jul. 3, 1997

[30] Foreign Application Priority Data

Dec. 22, 1995 [GB] United Kingdom ............... 9526419

[51] Int. Cl.⁷ ............... C08G 73/00; C08G 73/06
[52] U.S. Cl. ............ 528/423; 528/422; 528/367; 528/368; 528/369
[58] Field of Search .................... 528/422, 423, 528/367, 368, 369

[56] References Cited

U.S. PATENT DOCUMENTS

| | | | |
|---|---|---|---|
| 5,041,516 | 8/1991 | Frechet et al. | 528/44 |
| 5,229,490 | 7/1993 | Tam | 530/324 |

FOREIGN PATENT DOCUMENTS

| | | |
|---|---|---|
| 0115771 | 8/1984 | European Pat. Off. |
| 9011778 | 10/1990 | WIPO . |
| 9318075 | 9/1993 | WIPO . |

OTHER PUBLICATIONS

Chem Abstract: 123:144777 "Rigid rod polyimides with n–alkoxymethyl side chains" "Park et al."

A. Kumar et al., "A Novel One–pot Synthesis of Hyperbranched Polyurethanes" J. Chem. Soc., Chem. Commun., 1993; pp. 1453–1454.

CA 123:83995 and J. Shao et al., "Unprotected Peptides as Building Blocks for the Synthesis of Peptide Dendrimers with Oxima, Hydrazone, and Thiazolidine Linkages" J. Am. Chem. Soc., vol. 117, No. 14, 1995; pp. 3893–3899.

CA 117:112473 and A.D. Meltzer et al., "Chain Dynamics in Poly(amido amine) Dendrimers. A Study of C NMR Relaxation Parameters" Macromolecules, vol. 25, No. 18, 1992; pp. 4541–4548.

D.A. Tomalia et al., "Dendritic Polymers" Encyclopaedia of Polymer Science and Engineering, Index Volume, 1190, John Wiley & Sons, New York; pp. 46–92.

F.M. Houlihan et al., "Thermally Depolmerizable Polycarbonates. 2. Synthesis of Novel Linear Tertiary Copolycarbonates by Phase–Transfer Catalysis" Macromolecules, vol. 19, No. 1, 1986; pp. 13–19.

*Primary Examiner*—Duc Truong
*Attorney, Agent, or Firm*—Gifford, Krass, Groh, Sprinkle, Anderson & Citkowski, P.C.

[57] ABSTRACT

A process for the preparation of a compound or polymer having at least one functional group selected from hydroxyl, thiol, amino and carboxylic acid groups is characterized in that a compound or polymer (A) containing a group of formula (I),

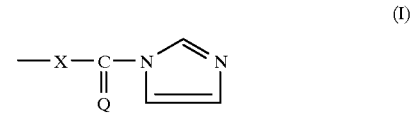

where Q represents O or S and X represents —O—, —S—, —NH— or a direct bond, the group being linked to the remainder of the compound or polymer through a carbon atom, is reacted with a compound (B) containing at least two functional groups selected from hydroxyl, thiol, amino and carboxylic acid groups, one of which functional groups (II) reacts with the group of formula (I) and one of which functional groups (III) is substantially unreactive with the group of formula (I) under the conditions of reaction, so that the compound (B) becomes bonded to (A) through the reaction of groups (I) and (II) forming a compound or polymer containing unreacted functional groups (III). The invention also includes dendritic polymers obtainable by the process and intermediates obtainable in the process.

47 Claims, No Drawings

SELECTIVE CHEMICAL REACTIONS AND POLYMERS OF CONTROLLED ARCHITECTURE PRODUCED THEREBY

FIELD OF THE INVENTION

This invention relates to selective chemical reactions and to branched molecules, including dendritic polymers, and to polymers tipped with functional groups. By selective chemical reactions we mean reactions of a compound or polymer containing two different functional groups with a reagent which reacts only or predominantly with one of the said functional groups, leaving the other functional group free to take part in a subsequent chemical reaction.

Dendritic polymers, otherwise known as dendrimers, comprise a multivalent core surrounded by layers of branched structural units. The successive layers around the core are called generations and in each generation the degree of branching of the structural units multiplies. The dendritic polymers thus have a substantially spherical molecular structure with a very large number of terminal groups at the surface of the molecule; the terminal groups may be functional groups so that the dendritic polymer may have very high functionality compared to its molecular size.

BACKGROUND ART

Dendritic polymers, particularly polyamidoamines and amidoalcohols, polyethers, polythioethers, polyethyleneimines and polyamides are described in Encyclopaedia of Polymer Science and Engineering, index volume, 1990, John Wiley & Sons, New York in an article by D. A. Tomalia et al. at pages 46–92. Dendritic polyesters are described in WO-A-93/18075. U.S. Pat. No. 5,229,490 describes dendritic polyamides having antigens bound thereto.

The spherical nature of dendrimers leads to high molecular weight molecules which do not suffer from entanglement, unlike conventional linear chain polymers. Dissolution in solvents is therefore fast and viscosities are low, leading to the possibility of "high solids" formulations, for example of coatings, sealants or adhesives, with favourable physical properties. The crosslinking of dendrimers leads to the formation of highly branched networks even after very few reactions have occurred, and the subsequent increase in molecular weight is dramatic, leading initially to linear-like entangled networks and then to highly crosslinked materials.

There is a need for dendrimers based on a wider range of chemical linkages and for alternative methods of preparation of dendrimers.

Functionally tipped polymers are known; for example hydroxyl and amino tipped polyethers, amino tipped polyamides and carboxyl tipped diene polymers are available commercially. There is a need for polymers tipped with a plurality of functional groups at each end and for convenient reactions for changing the terminal functionality of a polymer.

A paper by F. M. Houlihan et. al. in Macromolecules 1986, 19, pp 13–19, describes the synthesis of linear tertiary polycarbonates by reacting a ditertiary alcohol with carbonyl diimidazole and reacting the product with a diprimary alcohol.

DISCLOSURE OF THE INVENTION

According to one aspect of the invention, a process for the preparation of a compound or polymer having at least one functional group selected from hydroxyl, thiol, amino and carboxylic acid groups is characterised in that a compound or polymer (A) containing a group of the formula:

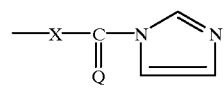

where Q represents O or S and X represents —O—, —S—, —NH— or a direct bond, the group being linked to the remainder of the compound or polymer through a carbon atom, is reacted with a compound (B) containing at least two functional groups selected from hydroxyl, thiol, amino and carboxylic acid groups, one of which functional groups (II) reacts with the group of formula (I) and one of which functional groups (III) is substantially unreactive with the group of formula (I), so that the compound (B) becomes bonded to (A) through the reaction of groups (I) and (II) forming a compound or polymer containing unreacted functional groups (III).

In a related process according to the invention for the preparation of a substituted amide, a compound containing an aliphatic carboxylic acid group and at least one substituent selected from alcohol and thiol groups is reacted with carbonyl diimidazole to convert the carboxylic acid group to a group of the formula:

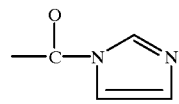

and the resulting compound (A') is reacted with a compound or polymer (B') containing at least one primary amine group to produce the substituted amide.

The invention also includes a dendritic polymer comprising at least two limbs radiating from a core, each of said limbs comprising at least two branches, characterised in that the branches contain a linkage selected from carbonate, urethane, urea, amide and ester linkages and that each limb has a linkage selected from carbonate, urethane and urea linkages between the branches and the core.

The invention further includes a dendritic polymer comprising at least three limbs radiating from a core, each of said limbs comprising at least two branches, characterised in that each limb has a linkage selected from carbonate, urethane and urea between the branches and the core.

The compound or polymer (A) can in general be produced by reaction of a compound or polymer containing hydroxyl, thiol, amine or carboxylic acid groups with carbonyl diimidazole or thiocarbonyl diimidazole. The imidazole ring can be substituted or can be fused to a benzene ring, leading to a substituted imidazole ring in the group of formula (I), but this is not preferred.

The preferred reagent is carbonyl diimidazole so that compound or polymer (A) is formed by reaction of groups selected from alcohol groups, thiol groups, primary amino groups and carboxylic acid groups with carbonyl diimidazole to form an imidazolide in which active hydrogen atoms of the alcohol, thiol and/or amino groups, and/or the whole carboxylic acid groups, are replaced by carbonyl imidazole groups of the formula:

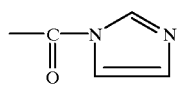

The term "imidazolide" is used in this specification to describe a 1-imidazole carboxyl ester of an alcohol having the structure

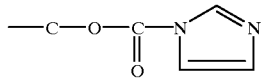

or a 1-imidazole carboxamide having the structure

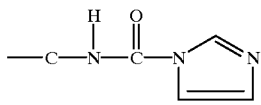

as well as an imidazolide having the structure

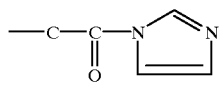

The imidazolides can be pre-oared in alternative ways, although preparation from carbonyl diimidazole is most convenient, especially as a step in dendrimer synthesis. 1-imidazole carboxyl esters can be prepared by reaction of a chloroformate with imidazole or by reaction of the carbonyl chloride of imidazole with an alcohol. 1-Imidazole carboxamides can be prepared by reaction of a carbamoyl chloride with imidazole or by reaction of the carbonyl chloride of imidazole with an amine. 1-Imidazole carbonyl compounds can be prepared by reaction of an acyl chloride with imidazole.

The groups reacted with carbonyl diimidazole are most preferably secondary or tertiary alcohol groups or carboxylic acid groups. We have found that secondary and tertiary alcohol groups, and carboxylic acid groups, each react with carbonyl diimidazole to replace one imidazole ring to form an imidazolide as shown below:

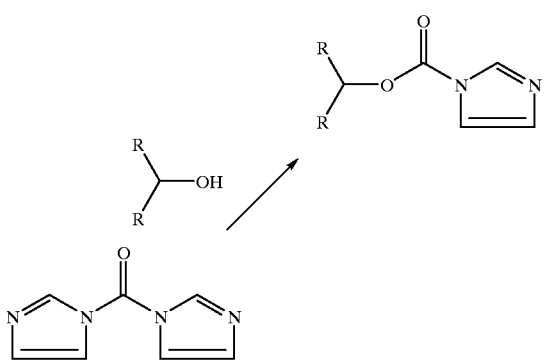

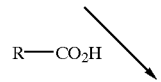

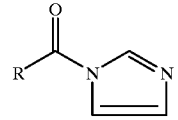

where each R is an alkyl group which may be substituted. This reaction proceeds with little tendency towards further reaction to replace the remaining imidazole ring. The reaction with a carboxylic acid takes place readily without need for a catalyst. The reaction with a secondary or tertiary alcohol proceeds only slowly in the absence of catalyst, but readily in the presence of a basic catalyst. Primary alcohols and primary amines, on the other hand, react readily with carbonyl diimidazole to replace both imidazole rings, forming a carbonate or urea linkage respectively, if the primary alcohol or primary amine is present in stoichiometric excess. This reaction can be used to produce linear polymers but is not helpful in producing dendritic polymers. The primary alcohols and primary amines will also, however, react with the imidazolides produced by reaction of a secondary or tertiary alcohol or carboxylic acid with carbonyl diimidazole, and this reaction can be used according to the invention as one step in the formation of a dendritic polymer.

The reaction of carbonyl diimidazole with a primary amine or primary alcohol can be used as one step in the preparation of a dendritic polymer if the reagents are used in stoichiometrically equivalent amounts or if the carbonyl diimidazole is used in excess, so that the predominant reaction is to replace only one of the imidazole rings of the carbonyl diimidazole. This reaction is more difficult to control than the reaction of carbonyl diimidazole with a secondary or tertiary alcohol, and separation of the desired 1-imidazole carboxyl ester or 1-imidazole carboxamide from carbonate or urea by-products may be necessary. Nevertheless, reaction of a primary amine with carbonyl diimidazole can be a useful step in preparing a dendrimer since it provides a route to dendrimers containing urea linkages which are otherwise difficult to prepare. We have found that although secondary amines react with carbonyl diimidazole, the resulting 1-imidazole carboxamide is unreactive with amine and alcohol groups.

Compounds or polymers prepared according to the invention can have one or more linkages selected from carbonate, urethane, urea, ester and amide linkages or their thio-equivalents where sulphur replaces oxygen. Examples of reaction schemes for producing such linkages are shown below:

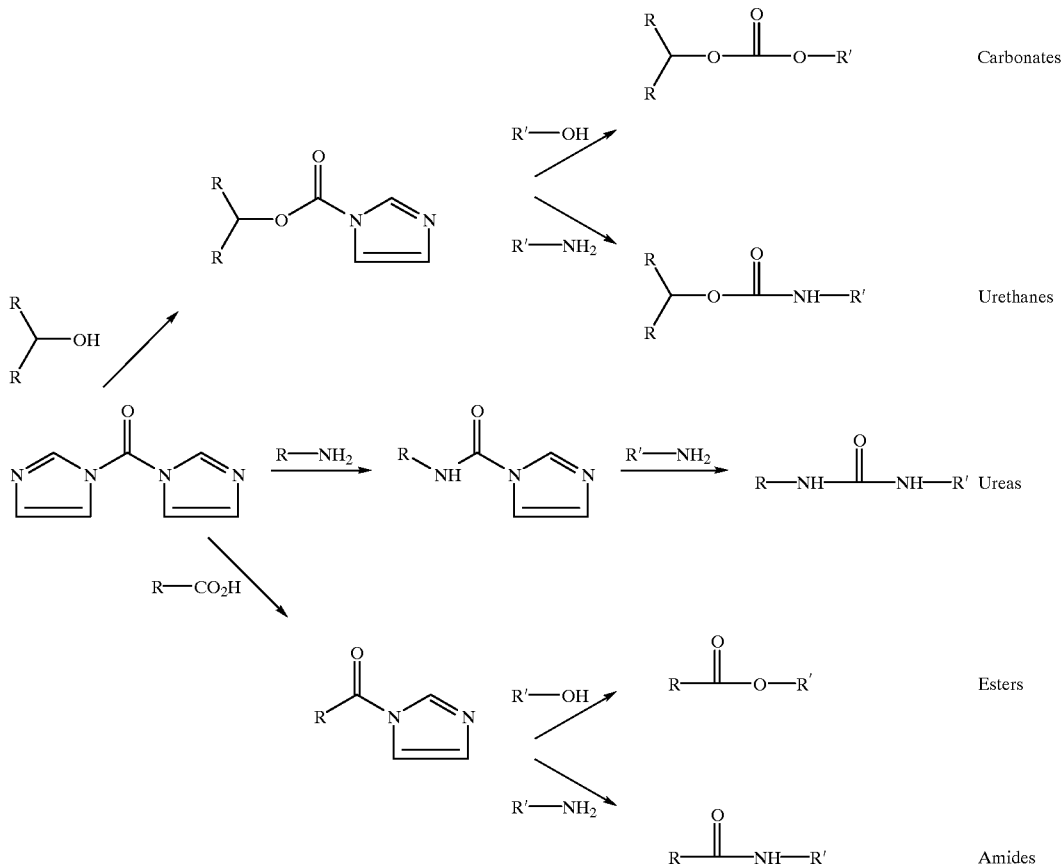

in which both the groups R and R are alkyl groups which can be substituted. In most cases R or R' can alternatively be aryl, although phenols and their 1-imidazole carboxyl esters are generally rather unreactive, as shown in Table 1 below.

The reactivity of different imidazolides with amines or alcohols of different structures is tabulated in Table 1. This reaction is based on reactions of the model compounds shown. Seventeen different compounds (four carboxylic acids of different structures, five amines of different structures and seven alcohols of different structures and a phenol) as set out across the top) of the table were each reacted with an equimolar amount of carbonyl imidazole to prepare an imidazolide. Each of the seventeen imidazolides was reacted with each of thirteen different compounds (five amines, seven alcohols and a phenol) as set out at the left of the table. The reaction conditions were as follows.

General Procedure for Evaluation of Specificity

A. Formation and reaction of an imidazolide from amine or alcohol

Carbonyl diimidazole (2.00 g, 12.30 mmol) was added to a round bottom flask. Toluene (40 ml) was added to the flask and the reaction mixture was stirred. A solution of alcohol or amine (12.30 mmol) in toluene (10 ml) was added dropwise to the reaction mixture. If an alcohol was used, KOH (0.1 g, 1.8 mmol) was also present. The reaction mixture was heated to 60° C. for 6 hours and then left to cool. A further solution of alcohol or amine (12.30 mmol) in toluene (5 ml) was added to the imidazolide solution and the resulting mixture was heated to 60° C. for a further 6 hours and then left to cool. The resulting solution was concentrated in vacuo and the residue was dissolved in dichloromethane, washed with water, dried (MgSC$_4$), filtered and concentrated in vacuo to give the product.

B. formation and reaction of an imidazolide from an aced

Acid (12.30 mmol) was added to a round bottom flask. Toluene (40 ml) was added to the flask and the reaction mixture was stirred. Carbonyl diimidazole (2.00 g, 12.30 mmol) was slowly added to the reaction mixture with resulting effervescence. After full addition the restriction was heated to 60° C. for 6 hours and then left to cool. A solution of alcohol or amine (12.30 mmol, in toluene (10 ml) was added dropwise to the reaction mixture. If an alcohol was used, KOH (0.1 g, 1.8 mmol) was also present. The reaction mixture was heated to 60° C. for 6 hours and then left to cool. The resulting solution was concentrated in vacuo and the residue was dissolved in dichloromethane, washed with water, dried (MgSO$_4$), filtered and concentrated in vacuo to give the product.

The reaction products were analysed by thin layer chromatography and nuclear magnetic resonance spectroscopy to determine whether reaction had taken place to form the amide, urea, urethane, ester or carbonate. In a majority of cases, the reaction proceeded readily; this is indicated in Table 1 by ✓. In many cases there was no reaction or only a limited amount of reaction. This is indicated in Table 1 by x.

TABLE 1

| | Imidazolide Intermediates | | | | | | | | |
|---|---|---|---|---|---|---|---|---|---|
| | Acetic Acid | Ethyl- butyric Acid | Benzoic Acid | Phenyl acetic Acid | Hexyl- amine | 1- Ethylpropyl- amine | Dibutyl- amine | Aniline | Benzyl- amine |
| Hexylamine | ✓ | ✓ | ✓ | ✓ | ✓ | ✓ | x | ✓ | ✓ |
| 1-Ethylpropylamine | ✓ | ✓ | ✓ | ✓ | ✓ | ✓ | x | ✓ | ✓ |
| Dibutylamine | x | x | ✓ | ✓ | ✓ | ✓ | x | ✓ | ✓ |
| Aniline | ✓ | ✓ | ✓ | ✓ | ✓ | ✓ | x | ✓ | ✓ |
| Benzylamine | ✓ | ✓ | ✓ | ✓ | ✓ | ✓ | x | ✓ | ✓ |
| 1-Butanol | ✓ | ✓ | ✓ | ✓ | ✓ | ✓ | x | ✓ | ✓ |
| 2-Propylpentanol | ✓ | ✓ | ✓ | ✓ | ✓ | ✓ | x | ✓ | ✓ |
| Neopentyl alcohol | x | x | ✓ | ✓ | x | x | x | ✓ | x |
| Isopropanol | ✓ | ✓ | ✓ | ✓ | ✓ | ✓ | x | ✓ | ✓ |
| 2,5-Dimethyl-4-heptanol | x | x | ✓ | ✓ | ✓ | x | x | ✓ | ✓ |
| t-Butanol | x | x | x | x | x | x | x | x | x |
| 3-Isopropyl phenol | ✓ | ✓ | ✓ | ✓ | x | x | x | ✓ | x |
| Benzyl alcohol | ✓ | ✓ | ✓ | ✓ | ✓ | ✓ | x | ✓ | ✓ |

| | Imidazolide Intermediates | | | | | | | |
|---|---|---|---|---|---|---|---|---|
| | 1- Butanol | 2-Propyl- pentanol | Neopentyl alcohol | Isopro- panol | 2,5-Dimethyl- 4-heptanol | t- Butanol | 3-Isopropyl phenol | Benzyl alcohol |
| Hexylamine | ✓ | ✓ | ✓ | ✓ | ✓ | ✓ | x | ✓ |
| 1-Ethylpropylamine | x | x | ✓ | ✓ | ✓ | ✓ | x | ✓ |
| Dibutylamine | ✓ | ✓ | x | ✓ | x | x | x | ✓ |
| Aniline | ✓ | x | ✓ | x | x | x | x | ✓ |
| Benzylamine | ✓ | ✓ | ✓ | ✓ | ✓ | ✓ | x | ✓ |
| 1-Butanol | ✓ | ✓ | x | ✓ | ✓ | ✓ | x | ✓ |
| 2-Propylpentanol | ✓ | ✓ | x | ✓ | ✓ | ✓ | x | ✓ |
| Neopentyl alcohol | x | x | x | ✓ | ✓ | ✓ | x | ✓ |
| Isopropanol | x | x | x | ✓ | x | x | x | ✓ |
| 2,5-Dimethyl-4-heptanol | x | x | x | x | x | x | x | ✓ |
| t-Butanol | x | x | x | x | x | x | x | x |
| 3-Isopropyl phenol | x | x | x | x | x | x | x | x |
| Benzyl alcohol | ✓ | ✓ | x | ✓ | ✓ | ✓ | x | ✓ |

In general, if an imidazolide is reacted with a compound containing two amine groups, one of which is of a type marked ✓ on Table 1 and the other of which is of a structure marked x on Table 1, the imidazolide will react substantially quantitatively with the group whose structure is marked ✓. Similarly, if an imidazolide is reacted with a compound containing two alcohol groups, one of which is of a type marked ✓ in Table 1 and the other of which is of a structure marked x in Table 1, the imidazolide will react substantially quantitatively with the group whose structure is marked ✓.

In general, if an imidazolide will react with a particular type of amine according to Table 1, it will react preferentially with the amine group of a compound containing that type of amine group and also containing a hydroxyl or carboxylic acid group if the reaction is carried out in the absence of any added base. The imidazolides do not in general react with carboxylic acid groups, so that if an imidazolide will react only with a particular type of alcohol according to Table 1, it will react with the alcohol group of a compound containing that type of alcohol group and also a carboxylic acid group.

Thus, in a process according to the invention for the preparation of a substituted amide, a compound or polymer (A) of the formula:

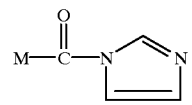

derived from an aliphatic carboxylic acid MCOOH in which M is an aliphatic group is reacted with a compound (B) containing at least one primary amine group and at least one substituent selected from alcohol, thiol, carboxylic acid and secondary amine groups to produce the substituted amide. In another process for the preparation of a substituted amide, a compound or polymer (A) of the formula:

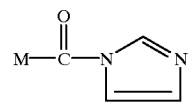

derived from an aromatic carboxylic acid MCOOH in which M is a phenyl, substituted phenyl, benzyl or substituted benzyl group is reacted with a compound (B) containing at least one amine group and at least one substituent selected from alcohol, thiol and carboxylic acid groups to produce the substituted amide.

In a process according to the invention for the preparation of a substituted ester, a compound or a polymer (A) of the formula:

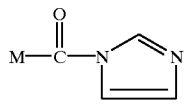

derived from a carboxylic acid MCOOH is reacted with a compound (B) containing at least one primary or secondary hydroxyl group and at least one substituent selected from tertiary alcohol and carboxylic acid groups in the presence of a base to produce the substituted ester.

In one process according to the invention for the preparation of a substituted urethane, a compound or polymer (A) of the formula:

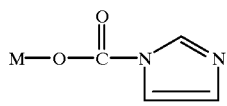

derived from a secondary or tertiary aliphatic alcohol MOH where M is a secondary or tertiary aliphatic group containing at least 4 carbon atoms is reacted with a compound (B) containing at least one primary amine group and at least one substituent selected from alcohol, thiol, carboxylic acid and secondary amine groups to produce the substituted urethane. In another process for the preparation of a substituted urethane, a compound or polymer (A) of the formula:

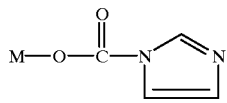

derived from a primary alcohol MOH is reacted with a compound (B) containing at least one amine group and at least one substituent selected from alcohol, thiol and carboxylic acid groups to produce the substituted urethane.

In a process according to the invention for the preparation of a substituted organic carbonate, a compound or polymer (A) of the formula:

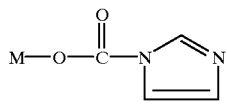

derived from aliphatic alcohol MOH is reacted with a compound (B) containing at least one primary alcohol group and at least one substituent selected from secondary or tertiary alcohol, thiol and carboxylic acid groups in the presence of a basic catalyst to produce the substituted carbonate.

For the formation of branched compounds or polymers, and eventually dendritic polymers, the compound (B) should contain one group of one type and at least two groups of the other type, that is to say it should contain one group (II) and at least two groups (III) or one group (III) and at least two groups (II).

Dendritic polymers can in general be formed according to the invention either by divergent polymer growth or by convergent polymer growth.

In convergent polymer growth, an initial reagent having one reactive functional group is reacted with a branching reagent having at least two groups reactive with that functional group and a single functional group which is not reactive with (and may be the same as) the reactive functional group in the initial reagent. A "wedge"-shaped molecule is produced having at least two branches based on a residue of the initial reagent and a single functional group; this can be reacted with the branching reagent to form a further generation of the dendrimer, forming a larger and more branched "wedge", still with a single functional group. In the final step of convergent polymer growth, the highly branched "wedge" is reacted with a reagent having at least two, and preferably three or more, groups reactive with the functional group of the wedge. The dendritic polymer formed has terminal groups at its surface which are the residues of the initial reagent. These residues may be unsubstituted or may contain a functional group which is unreactive in the reaction steps of dendritic polymer growth but which modifies the properties of the dendritic polymer produced. Thus in a process for the preparation of a branched compound or polymer containing at least two linkages selected from carbonate, urethane, urea, amide and ester linkages, which may be a step in the preparation of a dendritic polymer by convergent growth, the compound (B) contains at least two functional groups which are reactive with the group of formula (I).

The said branched compound or polymer can be further reacted with carbonyl diimidazole or thiocarbonyl diimidazole to produce a branched compound or polymer of the formula:

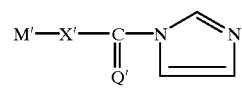

(IV)

where Q' represents O or S, X' represents —O—, —S—, —NH— or a direct bond and M' represents a branched organic radical formed by the reaction of compound or polymer (A) and compound (B).

The branched compound or polymer of formula (IV) can be further reacted with a compound or polymer (C) containing at least two groups reactive with the group of formula:

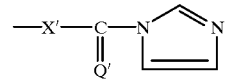

thereby forming a dendritic polymer containing at least two of the branched organic radicals M' by convergent growth.

The compound or polymer (C) may additionally contain a functional group selected from hydroxyl, thiol, amino and carboxylic acid groups which is substantially unreactive with the group of formula:

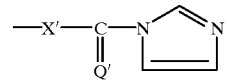

thereby forming a dendritic polymer containing a functional group. This dendritic polymer can be further reacted with carbonyl diimidazole or thiocarbonyl diimidazole to produce a dendritic polymer (D) in which the said functional group is converted to a group of the formula:

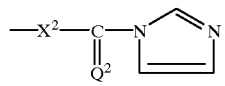

where $Q^2$ represents O or S and $X^2$ represents —O—, —S—, —NH— or a direct bond. The dendritic polymer (D) can be further reacted with a compound or polymer (E) containing at least two groups reactive with the group of formula:

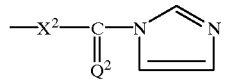

thereby forming a dendritic polymer containing an increased number of branches.

The compound or polymer (C) or (E) containing at least two reactive groups may be a polymer in which said reactive groups are present as chain terminating groups, whereby a polymer capped with at least two dendritic structures is produced.

The process of the invention can for example be used to prepare a dendritic polymer by convergent polymer growth by a reaction scheme in which:

(a) in a first step a compound (C1) which is a secondary or tertiary alcohol or a carboxylic acid is reacted with carbonyl diimidazole to form an imidazolide in which the carboxylic acid group, or active hydrogen atom of the alcohol group, is replaced by a carbonyl imidazole group of the formula:

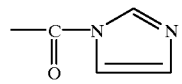

(b) in a second step the resulting imidazolide is reacted with a compound (C2) having at least two groups (II) selected from primary alcohol groups and primary amine groups and one group selected from alcohol groups (III) which are unreactive with imidazolide groups and carboxylic acid groups, whereby the compound (C2) reacts through its primary alcohol or primary amine groups to replace the imidazole ring, thus forming a compound containing at least two residues of (C1) and a group selected from alcohol groups and carboxylic acid groups.

As can be seen from Table 1, secondary amines can be used as unreactive groups (III) if the compound (C1) is a secondary or tertiary alcohol or an aliphatic carboxylic acid, or can be used as reactive groups (II) if the compound (C1) is an aryl or aralkyl carboxylic acid.

The reaction steps (a) and (b) can be repeated alternately to produce successive generations of dendritic polymer growth. In a final step following formation of an imidazolide by reaction (a), the imidazolide can be reacted with a compound containing at least two, preferably three or more, groups selected from primary alcohol groups and primary amine groups.

In divergent polymer growth, a core reagent having at least two functional groups is reacted with a branching reagent having one functional group which reacts with the core reagent and at least two functional groups which remain available for further reaction. In successive steps in divergent dendritic polymer growth, the number of functional terminal groups is multiplied, forming a dendritic polymer with a high concentration of reactive functional groups at the surface of the molecule. Thus in a process for the preparation of a compound or polymer having at least two functional groups selected from hydroxyl, thiol, amino and carboxylic acid groups, which may be a step in the preparation of a dendritic polymer by divergent growth, the compound (B) contains at least two functional groups (III) which are substantially unreactive with the group of formula (I). In an alternative process, the compound or polymer (B') contains at least two primary amine groups.

The compound or polymer having at least two functional groups can be further reacted with carbonyl diimidazole or thiocarbonyl diimidazole to produce a compound or polymer of the formula:

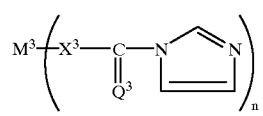

(V)

where $Q^3$ represents O or S, $X^3$ represents —O—, —S—, —NH— or a direct bond, $M^3$ represents an organic radical formed either by the reaction of compound or polymer (A) with compound (B) or by the reaction of compound (A') with compound or polymer (B') and n is an integer of at least 2 corresponding to the number of functional groups (III) in compound (B) or the number of primary amine groups In the compound or polymer (B').

The compound or polymer (V) can be reacted with a compound (F) having at least one functional group selected from hydroxyl, thiol and amino groups which is reactive with the group of formula:

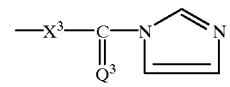

thereby forming a branched molecule having a linkage, selected from carbonate; urethane, urea, amide and ester linkages, in each branch.

If the compound (F) additionally contains at least two functional groups selected from hydroxyl, thiol, amino and carboxylic acid groups which are substantially unreactive with the

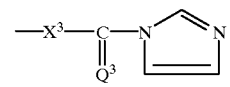

group but which are reactive with carbonyl diimidazole, and the said branched molecule is reacted with carbonyl diimidazole or thiocarbonyl diimidazole to form at least two

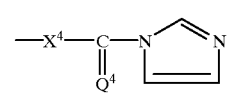

groups in each branch, where $Q^4$ represents O or S and $X^4$ represents —O—, —S—, —NH— or a direct bond, and is then reacted with a compound having at least one functional group selected from hydroxyl, thiol and amino groups which is reactive with the group of formula:

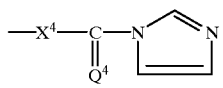

thereby forming a dendritic polymer by divergent growth.

For example the process of the invention can be used to prepare a dendritic polymer by divergent polymer growth by a reaction scheme in which:

(a) in a first step a compound (D1) having at least two groups selected from secondary or tertiary alcohol groups and carboxylic acid groups and which contains no primary alcohol groups or amino groups is reacted with carbonyl diimidazole to form an imidazolide (A) in which the carboxylic acid groups, or the active hydrogen atoms of the alcohol groups, are replaced by carbonyl imidazole groups of the formula:

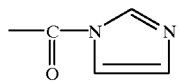

(b) in a second step the resulting imidazolide (A) is reacted with a compound (B) having one group selected from primary alcohol groups and primary amine groups and at least two groups selected from secondary and tertiary alcohol groups and carboxylic acid groups, whereby the imidazole ring is replaced by a residue of the compound (B) reacted through its primary alcohol or primary amine group, thus forming a compound having at least two groups selected from secondary and tertiary alcohol groups and carboxylic acid groups.

The reaction steps (a) and (b) can be repeated alternately to produce successive generations of dendritic polymer growth.

If the reaction steps (a) and (b) are repeated, the compound (B) used in the final step need not have secondary or tertiary alcohol groups or carboxylic acid groups. It need only have one group selected from primary alcohol groups and primary amine groups. In many cases it will be desired to have reactive groups such as alcohol, secondary amine or carboxylic acid groups at the surface of the dendritic polymer to take part in crosslinking/curing reactions; this is in general an advantage of dendritic polymers prepared by divergent growth. The primary alcohol or primary amine used in the final step can however be unsubstituted to leave hydrocarbon groups at the surface of the dendritic polymer or can be substituted by groups which are not reactive with the imidazolide and which can be chosen to give specific properties, for example fluoro groups or siloxane groups to give a low energy surface, phosphate ester groups to promote adhesion to metal, U.V. absorbing groups such as benzotriazole or ethylenically unsaturated groups for reaction with crosslinking monomers.

Substantially all alcohol groups will react with carbonyl diimidazole under certain reaction conditions, for example at a temperature of at least 50° C. in a solvent (such as toluene) in which carbonyl diimidazole is soluble at such a temperature and in the presence of a strong base, for example potassium hydroxide, sodium hydroxide, a quaternary ammonium hydroxide or a strongly basic tertiary amine such as diazabicycloundecene. Reactions of amines and carboxylic acids with carbonyl diimidazole generally proceed at ambient temperature in the absence of catalyst.

The alcohol groups which are unreactive with imidazolide groups are generally secondary or tertiary alcohol groups but can alternatively be primary alcohol groups which are sterically hindered. Table 1 shows that neopentyl alcohol (2,2-dimethylpropan-1-ol) is less reactive with imidazolides than other primary alcohols and this applies in general to —$CH_2OH$ groups attached to a tertiary alkyl structure. Conversely, isopropanol is much more reactive than other secondary alcohols. Pentaerythritol, for example, may react as a polyol having three primary alcohol groups and one hindered alcohol group which is unreactive with imidazolide. 2,2-Bis(hydroxymethyl)-butanol (trimethylolpropane) and 2-methyl-2-hydroxymethylpropane-1,3-diol (trimethylolethane) are examples of polyhydric alcohols which under some reactive conditions will react as tri(primary alcohols) but under controlled reaction conditions will react as di(primary alcohols) having an additional hindered alcohol group. If trimethylolpropane is reacted with an imidazolide in molar ratio 1:3 in toluene solution at a temperature of at least 50° C. in the presence of a strong base catalyst, all three of its alcohol groups will react with the imidazolide groups, whereas if it is reacted in t-butanol solution the dicarbonate is predominantly formed (at least 80% if the trimethylolpropane and imidazolide are reacted in molar ratio 1:2). In the latter reaction the remaining hydroxyl group is so sterically hindered that it reacts similarly to a secondary alcohol group; it will react with carbonyl diimidazole but not with an imidazolide.

The process of the invention can for example be used to prepare dendritic polycarbonates. In this case, the groups chosen to react with the carbonyl diimidazole and the imidazolide are all alcohol groups. In the preparation of a dendritic polycarbonate by divergent growth, (D1) is a compound having at least two groups selected from secondary and tertiary alcohol groups and (B) is a compound having a primary alcohol group and two groups selected from secondary or tertiary alcohol (or sterically hindered primary alcohol groups). In the preparation of a dendritic polycarbonate by convergent growth, (C1) is a secondary or tertiary alcohol and (C2) is a compound having at least two primary alcohol groups and one secondary or tertiary alcohol group. Dendritic polycarbonates or indeed any dendritic polymers containing carbonate linkages have not previously been described.

Thus, according to a further aspect of the invention, a dendritic polymer comprises at least two limbs radiating from a core radical, each of said limbs comprising at least two branches, characterised in that the branches contain a linkage selected from carbonate, urethane, urea, amide and ester linkages, and that each limb has a linkage selected from carbonate, urethane, urea, amide and ester linkages between the branches and the core, at least one of the said linkages being a carbonate linkage.

The steps in the formation of a dendritic polycarbonate by divergent growth are shown in the following reaction scheme, in which a disecondary alcohol such as pentane-2,4-diol forming the core of the dendrimer is reacted in alternate steps (i) with carbonyl diimidazole (CDI) and (ii) with a primary disecondary alcohol such as 4-hydroxymethyl-heptane-2,6-diol.

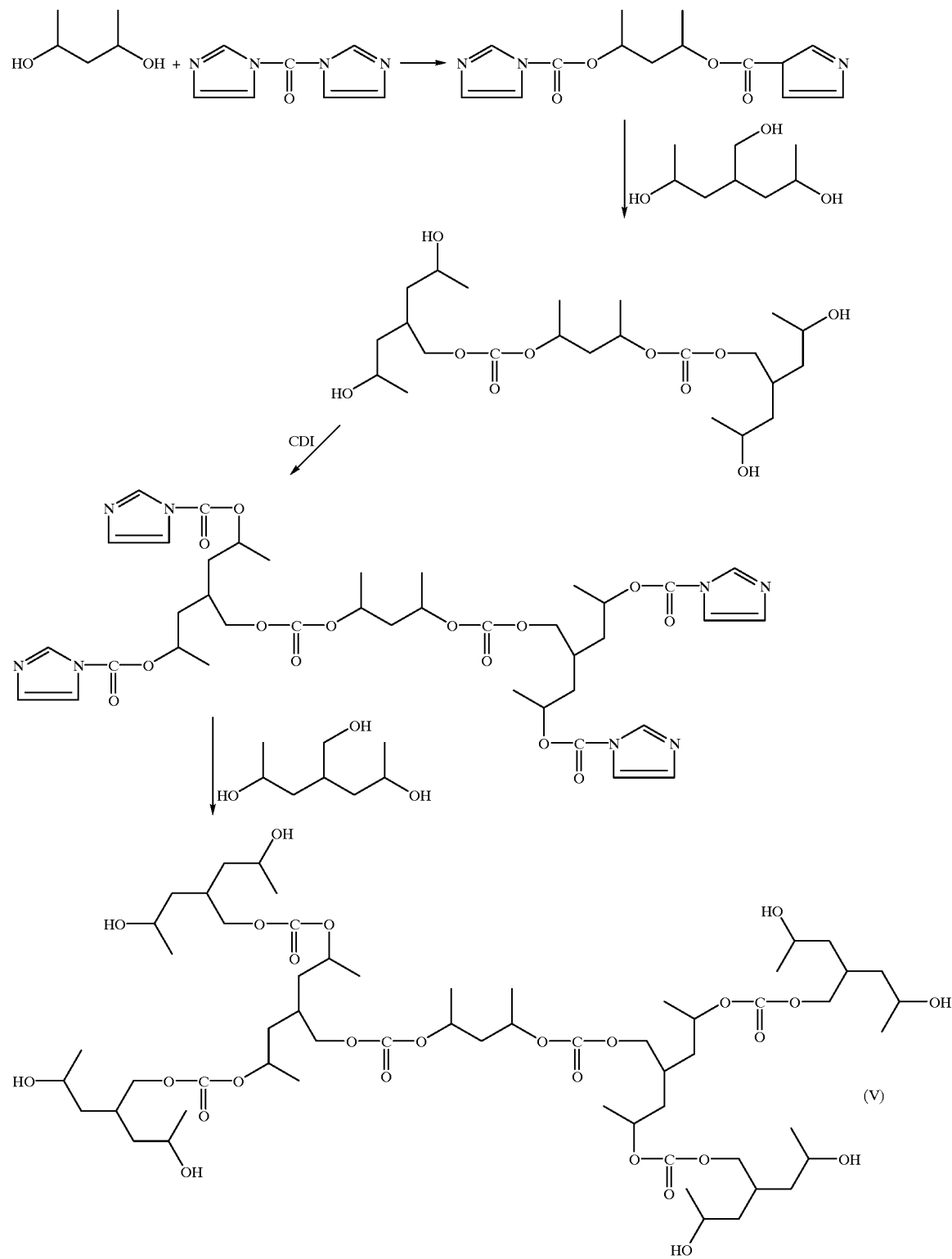

The product (VI) is a dendritic polycarbonate which may be useful in coatings formulations or can be reacted further with carbonyl diimidazole and then a primary disecondary alcohol to produce a further generation of dendritic polymer growth. (VI), as is typical of dendritic polymers prepared by divergent growth, has a multiplicity of functional groups, namely hydroxyl groups, at its surface, which may be useful for crosslinking.

Examples of other disecondary alcohols which can be used in place of pentane-2,4-diol are hexane-2,5-diol and heptane-2,6-diol and tertiary amines containing two secondary alkyl groups such as methyl bis(2-hydroxypropyl)

amine. Trisecondary alcohols such as tris (2-hydroxypropyl) amine (also known as triisopropanolamine) can alternatively be used, as can ditertiary alcohols such as 2,5-dimethylhexane-2,5-diol or tertiary secondary alcohols such as 2-methylhexane-2,5-diol.

Examples of ether primary disecondary alcohols which can be used in place of 4-hydroxymethyl-heptan-2,6-diol are

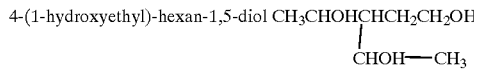

and 2-hydroxyethyl bis(2-hydroxypropyl) amine.

In general, the polyhydric alcohols used in the process of the invention should not have hydroxyl groups in a 1,2-relationship, i.e. attached to adjacent carbon atoms, since adjacent hydroxyl groups have the possibility of taking part in side reactions such as the formation of cyclic carbonates. If polymers containing cyclic carbonate groups are wanted, triols such as glycerol can react with carbonyl diimidazole to form a cyclic carbonate with a remaining imidazolide group for attachment to a polymer.

The steps in the formation of a dendritic polycarbonate by convergent growth are shown in the following reaction scheme, in which a secondary alcohol

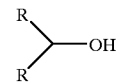

is reacted with carbonyl diimidazole to form an imidazolide

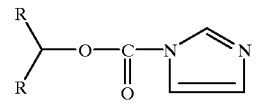

and this imidazolide is reacted in alternate reaction steps with a diprimary secondary alcohol such as heptane-1,4,7-triol and then with carbonyl diimidazole to form a growing "wedge" molecule. In a final step the "wedge" molecules are joined by a polyfunctional primary alcohol which preferably has at least three alcohol groups such as trimethylolpropane but could alternatively be a diol.

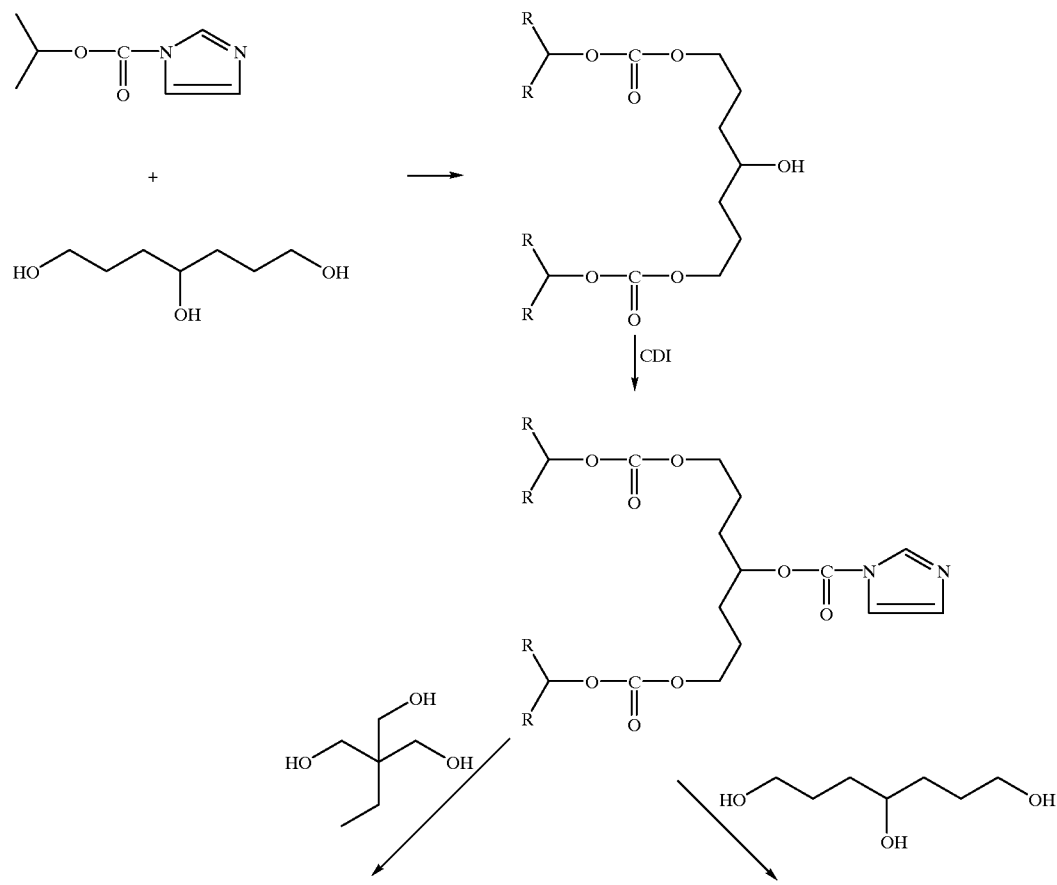

-continued

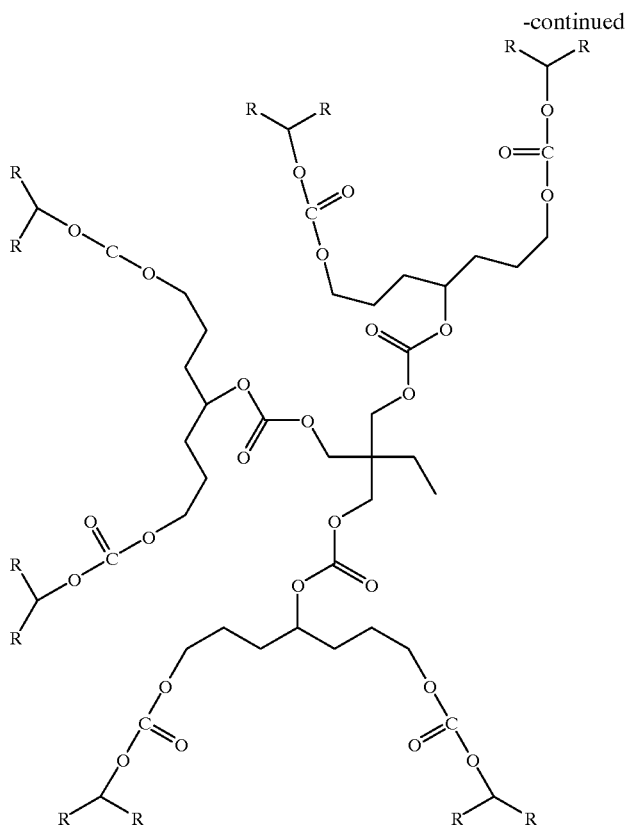

Terminated Growth to form final Dendrimer

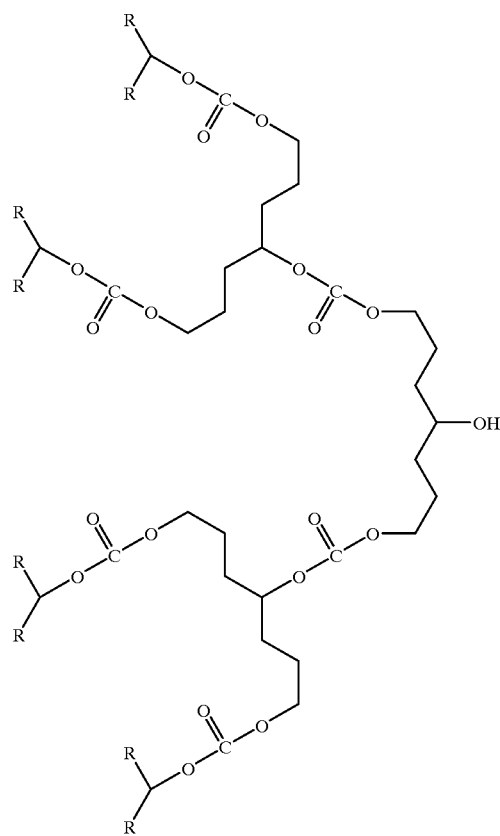

Coupled Wedges to form larger Wedge

The product (VII) is a dendritic polycarbonate having surface groups R derived from the secondary alcohol These can be unsubstituted hydrocarbon groups or can be other groups chosen to give a desired surface effect, for example fluorocarbon groups to give a low energy surface material. The "larger wedge" (VIII) can be coupled by a polyfunctional primary alcohol such as trimethylolpropane to produce a larger dendritic polycarbonate molecule, again having the groups R at the surface of the molecule.

The secondary alcohol can for example be isopropanol, 2-butanol, $CF_3CHOHCF_3$, a branched secondary alcohol such as 2,6-dimethyl-4-heptanol, an aralkyl alcohol such as 1-phenylethanol, a cyclic alcohol such as cyclohexanol, an ether alcohol such as 1-methoxy-propan-2-ol, an ester alcohol such as triethyl citrate or diethyl hydroxyglutarate, or a tertiary amine containing a secondary alcohol group such as dimethyl isopropanolamine. A tertiary alcohol, for example t-butanol, can be used in place of the secondary alcohol. Tertiary alcohols such as t-butanol have the advantage that the t-butoxy group can be thermally or chemically removed after the dendrimer has been synthesised, thereby generating surface hydroxyl functionality.

The diprimary secondary alcohol can for example be heptane-1,4-7-triol (as shown), pentane-1,3,5-triol, 2,5-bis (hydroxymethyl)-cyclohexanol or 3-hydroxymethylpentane-1,4-diol, or a tertiary amine derivative such as 1-(N,N-bis(2-hydroxyethyl)amino)-2-propanol, which is commercially available. The non-amine diprimary secondary alcohols which do not have alcohol groups on adjacent carbon atoms are not readily available commercially but can be synthesised by lithium aluminium hydride reduction of hydroxy-diesters, keto-diesters and keto-substituted lactones. For example, heptane-1,4,7-triol, pentane-1,3,5-triol and 3-hydroxymethyl-pentane-1,4-diol have been prepared by lithium aluminium hydride reduction of diethyl 4-oxopimelate, diethyl 3-hydroxyglutarate and 2-acetylbutyrolactone respectively. The diprimary secondary alcohols which are tertiary amine derivatives, such as 1-(N,N-bis(2-hydroxyethyl)amino)-2-propanol, are generally preferred to the non-amine diprimary secondary alcohols because of their greater solubility in aromatic hydrocarbons, which are the preferred solvents for dendritic polycarbonate preparation according to the invention.

The polyfunctional primary alcohol used in the final step of convergent growth of a dendritic polycarbonate preferably has at least three primary alcohol groups, for example trimethylolpropane, trimethylolethane, pentaerythritol or dipentaerythritol (bis(2,2-bis(hydroxymethyl)-3-hydroxypropyl) ether). It can alternatively be a diol; for example it can be a polymer tipped with primary alcohol groups such as a polyethylene glycol or polytetramethylene glycol, a hydroxy-tipped polyester or hydroxy-tipped polybutadiene. Such polymers comprising two dendritic wedges joined by a polymer chain may be useful as crosslinking agents and/or viscosity modifiers in coating compositions and sealants.

We have found that all the reaction steps involved in forming a dendritic polycarbonate by convergent growth can be carried out in solution, preferably in an aromatic hydrocarbon and preferably in the presence of a base, that is the reaction of a secondary or tertiary alcohol with carbonyl diimidazole and the reaction of the subsequent imidazolide with a diprimary secondary alcohol and the final coupling step with a polyfunctional primary alcohol. The preferred aromatic hydrocarbon is toluene, although xylene for example can be used. Alternative solvents such as tetrahydrofuran, methylene chloride, ester solvents such as butyl acetate, dimethyl sulphoxide or dimethyl formamide can be used but are not preferred. The base is preferably an alkali metal hydroxide with potassium hydroxide being most preferred although sodium hydroxide or a quaternary ammonium hydroxide can alternatively be used. The preferred temperature of reaction is from 20 or 40° C. up to the boiling point of the reaction solution, most preferably in the range 5° C. to 80° C. In general, the alcohol-functional reagents (with the exception of some of the diprimary secondary alcohols as discussed above), the imidazolides and the intermediate and final products of dendrimer synthesis are soluble in both hot and cold aromatic hydrocarbons, but carbonyl diimidazole and the imidazole formed as by-product are soluble in hot toluene but insoluble in cold toluene. The imidazole by-product can thus be removed simply by cooling the reaction solution to precipate imidazole and then removing it by filtration. Moreover, excess carbonyl diimidazole can be used to ensure complete conversion of secondary alcohol groups to imidazolide groups, with subsequent removal of unreacted carbonyl diimidazole by cooling and filtration. The imidazolide and the growing dendritic polycarbonate need not be isolated from solution during the whole dendrimer synthesis. For example, a four-step convergent reaction has been carried out with addition of reagents to the reaction solution in each step and without working of the solution apart from cooling and filtration, leading to a dendritic polycarbonate wedge of 95% purity as measured by NMR. The final dendritic polycarbonate can be isolated if required by evaporation of the solvent after cooling and filtering off the imidazole. In some cases the polymer solution can be used as the basis for a coating or adhesive formulation without removal of the solvent, particularly if the solvent has a relatively high flash point such as xylene or trimethylbenzene.

The process described above can in general be used to prepare various types of poly(thiocarbonate)s. Thiolcarbonate linkages can be formed by replacing either the secondary or tertiary alcohol of step (a) or the primary alcohol of step (b) by the corresponding thiol. Thionocarbonate linkages can be produced by the use of thiocarbonyl diimidazole in place of carbonyl diimidazole.

The process of the invention can also be used to prepare dendritic polyurethanes. For example, a compound (A) containing two or more secondary or tertiary alcohol groups can be reacted with carbonyl diimidazole to form an imidazolide, and the imidazolide can be reacted with a compound (B) containing one primary amine group (which reacts with the imidazolide to form a urethane linkage) and at least two secondary or tertiary alcohol groups, which can subsequently be reacted with carbonyl diimidazole to form further imidazolide groups, thus generating a dendritic polyurethane by divergent growth.

The compound (A) can for example be pentane-2,4-diol, 2,5-dimethyl-hexane-2,5-diol, triisopropanolamine or any of the diols (I) used in dendritic polycarbonate synthesis by divergent growth. The compound (B) can for example be N-(2-aminoethyl)-diisopropanolamine.

In a process for forming a simple dendrimer containing urethane linkages, the imidazolide formed by reaction of carbonyl diimidazole with the compound (A) can be reacted with a tertiary carbinamine (i.e. a tertiary alkyl primary amine), preferably a tri(substituted alkyl) methylamine in which the alkyl group is substituted by a functional group such as hydroxyl, for example tris(hydroxylmethyl) methylamine. The resulting dendritic molecule has three limbs each having three functionally substituted branches, and is useful as a crosslinking agent, for example in coating compositions. The reaction with the tris(hydroxymethyl) methylamine can be carried out at room temperature in an organic solvent without significant reaction of the hydroxyl groups. Tetrahydrofuran is a suitable solvent for both stages of this preparation.

Alternatively, a dendritic polyurethane can be prepared by convergent growth as shown in the following reaction scheme:

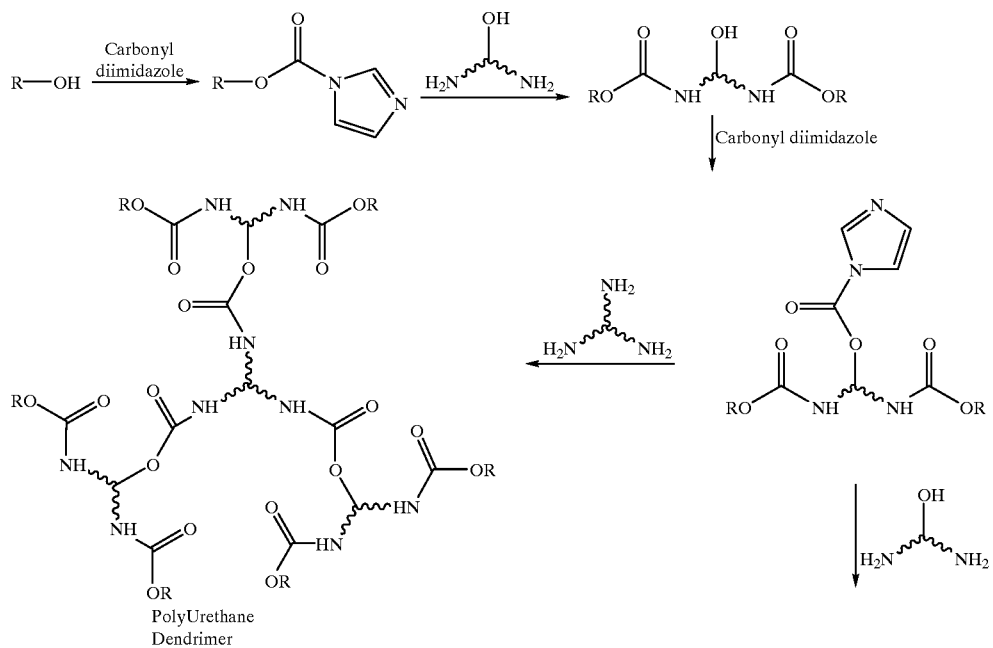

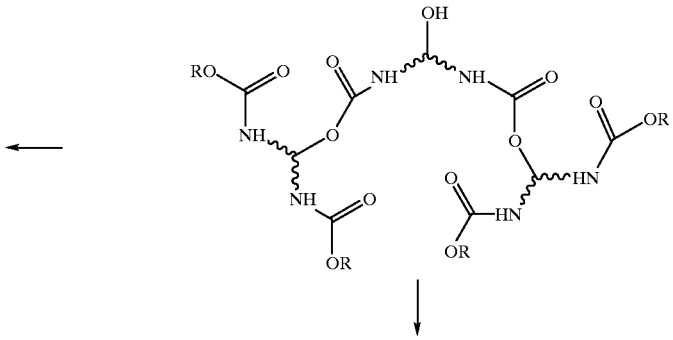

The alcohol (C1) is a secondary or tertiary alcohol, for example isopropanol, t-butanol, 2,6-dimethyl-4-heptanol or any of those mentioned above in connection with the preparation of dendritic polycarbonates by convergent growth. The compound (C2) is an aminoalcohol containing one secondary or tertiary hydroxyl group and at least two primary amine groups, for example 2-hydroxy-propane-1,3-diamine or 2-hydroxy-2-aminoethyl-propane-1,3-diamine. The polyamine used to couple the wedge-shaped imidazolide in the final stage of convergent growth of a dendritic polyurethane can for example be a triamine, tetramine or diamine, for example tris(2-aminoethyl)amine, tris(3-aminopropyl)amine, 4-aminomethyl-1,8-octanediamine, melamine or a polyether tipped with primary amine groups.

The reaction of the imidazolide with the compound (B) or (C2) containing one or more primary amine groups can be carried out at ambient temperature (for example 15–25° C.), preferably in an aromatic hydrocarbon solvent such as toluene, although the alternative solvents listed above can be used. The imidazole by-product precipitates from solution as it is formed and can be removed by filtration. Successive reaction steps in the preparation of the dendritic polyurethane can be carried out with removal of imidazole by-product and/or excess carbonyl diimidazole but without isolation of the intermediate reaction product.

As an alternative to reaction with the aminoalcohol, the imidazolide can be reacted with a diprimary secondary triamine such as diethylene triamine, which is widely available commercially. The primary amino groups react with the imidazolide groups, forming "wedge" molecules containing a secondary amine group. This can be reacted with an alkyl-substituted oxirane such as propylene oxide in a ring-opening reaction to form a N-hydroxyalkyl tertiary amine in which the alcohol group is a secondary alcohol group. This can then be reacted with carbonyl diimidazole (CDI) followed by a poly(primary amine) such as tris(2-aminoethyl) amine to form a polyurethane dendrimer, as shown in the following reaction scheme, R and R' being identical or different alkyl groups which can be substituted.

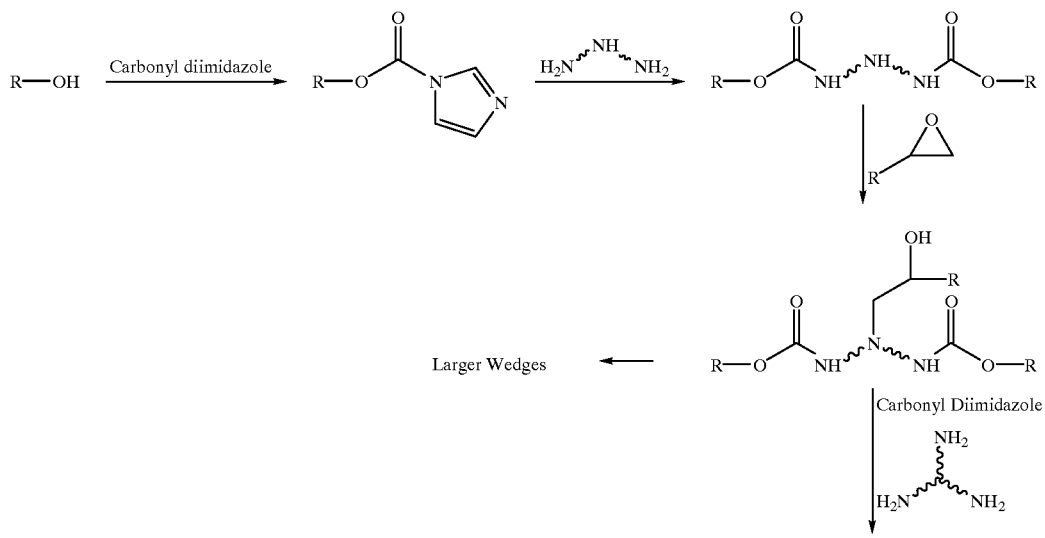

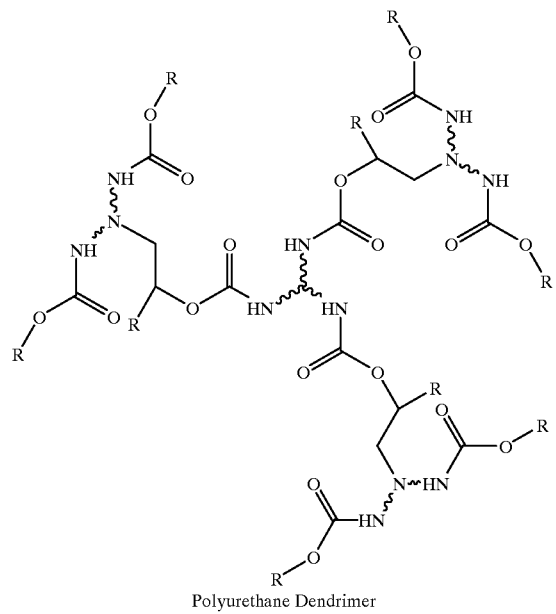

Polyurethane Dendrimer

Dendritic polyurethanes have not previously been described.

Dendritic polyurethanes can alternatively be prepared according to the invention by reacting a primary amine with excess carbonyl diimidazole to produce an imidazole carboxamide, which can be reacted with a diprimary secondary alcohol or diprimary tertiary alcohol to produce a "wedge" containing a secondary or tertiary alcohol group. This can be reacted to produce a dendritic polyurethane described above.

The process of the invention can be used in modified form to prepare dendritic polyureas. In a first reaction step, a primary amine is reacted with excess carboxyl diimidazole (CDI) to produce an imidazolide.

This imidazolide can be reacted at 0° C. or below with a polyamine containing one secondary amine group and at least two primary amine groups, for example diethylene triamine, forming a "wedge" molecule containing a secondary amine group (at higher temperatures there is no selectivity). The secondary amine group can be reacted with aziridine to convert it to a N-aminoethyl tertiary amine group. The aminoethyl primary amine group can be reacted with CDI to form a further imidazolide, and then with a polyvalent primary amine such as tris(aminoethyl)amine (TAEA) to produce a dendritic polyurea as shown in the following reaction scheme:

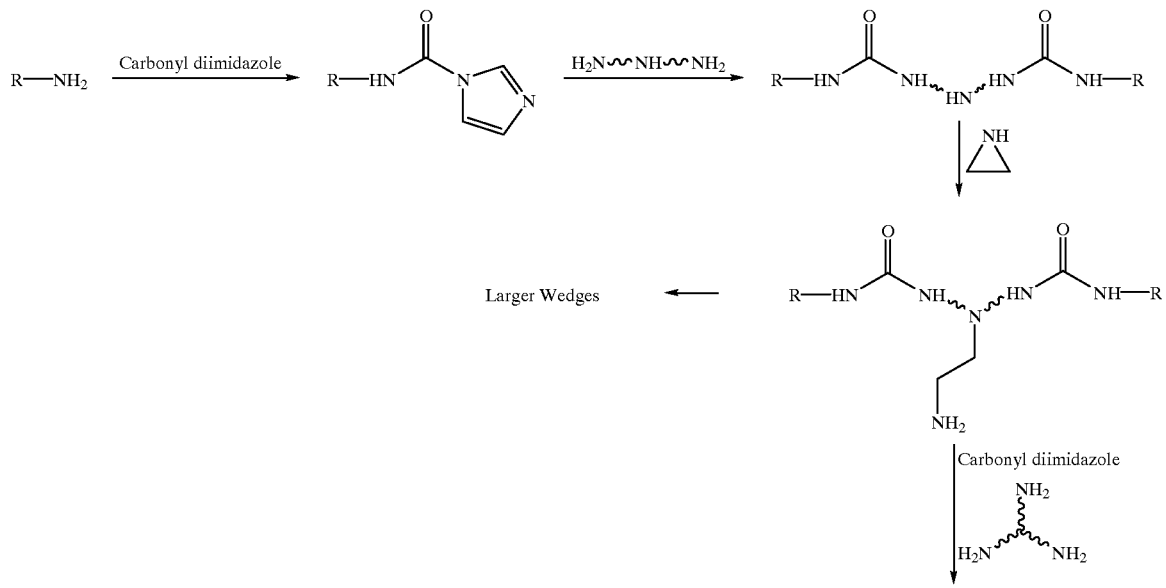

-continued

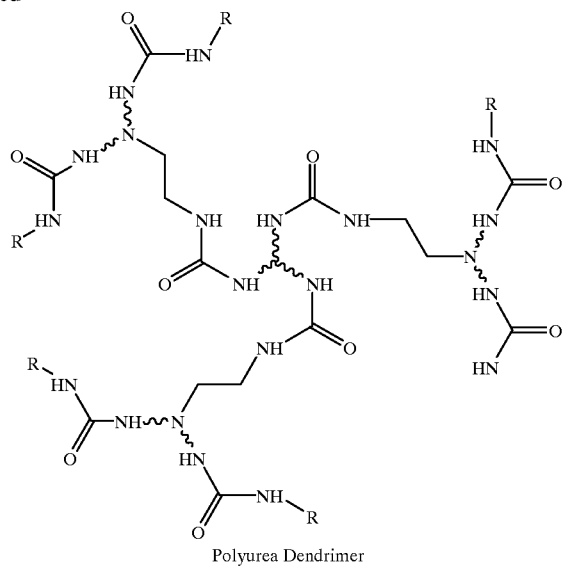

Polyurea Dendrimer

The imidazolide can alternatively be reacted with a polyvalent primary amine in which one amine group is protected from reaction, for example by a tertiary butyl oxy-carbonyl group formed by reaction with a stoichimometric amount of tertiary butyloxy-carbonyl anhydride $$(CH_3)_3C-O-\overset{O}{\underset{\|}{C}}-O-\overset{O}{\underset{\|}{C}}-O-C(CH_3)_3.$$

This forms a "wedge" molecule containing the protected amine group, which can be deprotected by heating to eliminate carbon dioxide and isobutylene and reacted with CDI followed by TAEA to form a dendritic polymer.

These reactions are shown in the following reaction scheme:

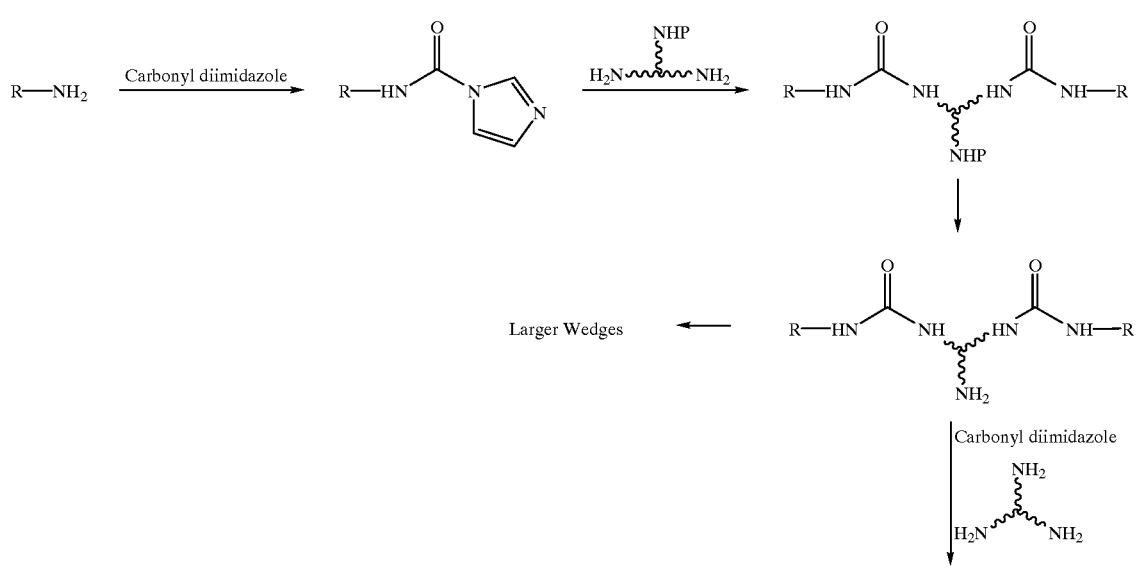

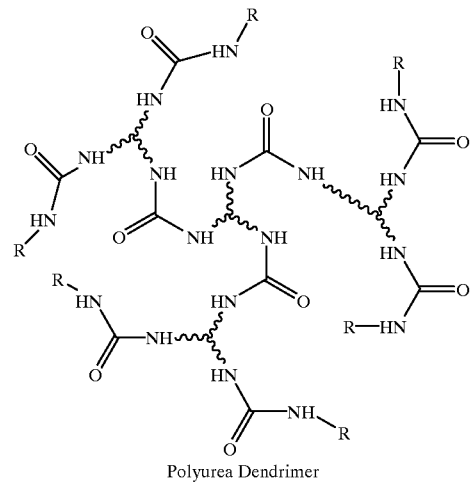

Polyurea Dendrimer

Dendritic polyureas have not previously been described. They are highly solvent-resistant, particularly to "Skydrol" alkyl phosphate esters used as hydraulic fluids and are useful in sealant and coating compositions for aerospace use.

The process of the invention can also be used to prepare dendritic polyamides. In a process for preparing a dendritic polyamide by divergent growth, a polyvalent carboxylic acid such as adipic, sebacic, succinic, phthalic or terephthalic acid is reacted with carbonyl diimidazole to produce an imidazolide. This reaction can be carried out in methanol solution at ambient temperature. We have found that at temperatures below about 30° C. the carbonyl diimidazole reacts exclusively with the carboxylic acid groups despite the presence of primary hydroxyl groups in methanol. The imidazolide can then be reacted with a compound containing one primary amino group and two or more carboxylic acid groups, for example aspartic acid or glutamic acid, to produce a compound containing amide linkages and free carboxylic acid groups. These steps can be repeated to form the polyamide dendrimer.

In a process for preparing a dendritic polyamide by convergent growth, a carboxylic acid is first reacted with carbonyl diimidazole to form an imidazolide. The imidazolide can be reacted with a compound containing two or more primary amine groups and one carboxylic acid group to produce a "wedge" containing amide linkages and one free carboxylic acid group. These steps can be repeated if desired. In a final reaction step, a "wedge" molecule whose carboxylic acid groups have been converted to imidazolide groups is reacted with a polyfunctional primary amine such as tris(2-aminoethyl) amine to produce the dendritic polyamide. In both the divergent and convergent growth preparations of dendritic polyamides, a reaction step involving use of an amino acid may need to be carried out in a more polar solvent such as dimethyl formamide or dimethyl sulphoxide. The preparation of dendritic polyamides by convergent growth has not previously been described.

In a preferred process for preparing a dendritic polyamide by convergent growth, a carboxylic acid is reacted with carbonyl diimidazole as described above, but the imidazolide formed is reacted with a polyamine having one secondary amine group and at least two primary amine groups, for example diethylene triamine. This forms a "wedge" molecule having amide linkages and a free secondary amine group. This is reacted with a cyclic carboxylic acid anhydride such as succinic, glutaric, diglycolic or maleic anhydride to produce a compound having a carboxylic acid-tipped chain bonded to the "wedge" through an amide linkage. The reaction with the anhydride can be carried out in an organic solvent at ambient temperature. The resulting carboxylic acid-functional molecule can be reacted with carbonyl diimidazole to produce an imidazolide which can be further reacted with diethylene triamine to produce a larger "wedge" or with a polyamine which is preferably a triprimary amine but could be a di- or tetra-primary amine to produce a polyamide dendrimer. This process is preferred because all steps of the process can be carried out in an aromatic hydrocarbon solvent such as toluene. If desired the steps can be carried out successively in such a solvent without isolation of intermediates. This process is illustrated by the reaction scheme below:

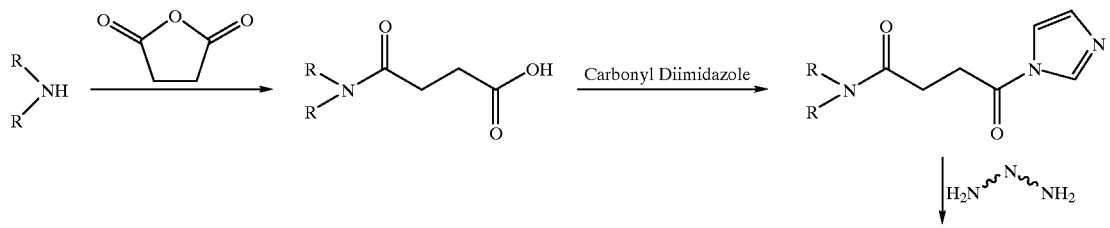

-continued

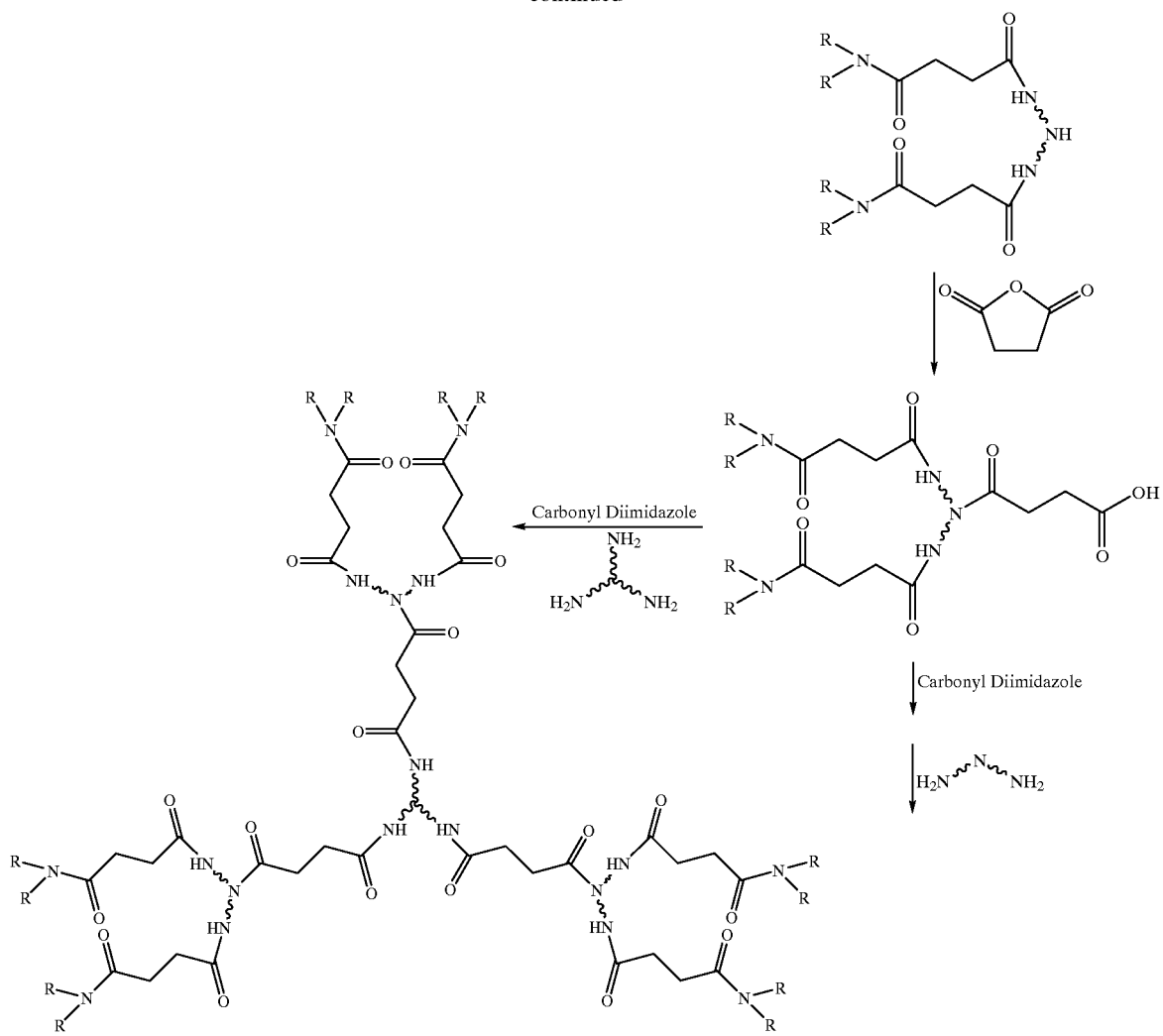

The initial carboxylic acid reacted with carbonyl diimidazole can be a simple carboxylic acid such as acetic acid, or it can be a fatty acid, or it can be an amide-containing carboxylic acid which may be formed by reaction of an amine (primary or secondary amine) and an anhydride as shown. The surface groups of the dendritic polyamide are derived from this carboxylic acid and can be chosen to be crosslinking groups such as alcohol groups or groups giving a surface effect such as fluoro or silane groups. For example, the amine shown as

above can be a hydroxy-substituted amine such as diethanolamine or tris(hydroxymethyl)methylamine. If the anhydride and carbonyl diimidazole are each used in a stoichiometric amount relative to amine groups and carboxylic acid groups respectively, and if the reactions are carried out at ambient temperature (10–30° C.), there is no significant reaction of the alcohol groups.

When joining dendritic polyamide "wedges" containing a secondary amine group to form a dendrimer, the secondary amine can alternatively be reacted with a compound containing two or more imidazolide groups derived from aromatic carboxylic acid groups, for example the bis (imidazolide) of diphenic acid (2,2'-biphenyldicarboxylic acid) or the bis(imidazolide) of terephthalic acid.

A simple dendrimer containing amide linkages can be formed by the reaction of a polycarboxylic acid having at least two, preferably at least three, carboxyl groups, for example citric acid or trimellitic acid, with carbonyl diimidazole (CDI) to form an imidazolide followed by reaction with a tertiary carbinamine (i.e. a tertiary alkyl primary amine). The reaction between the polycarboxylic acid and the CDI is preferably carried out in organic solvent, for example it can be carried out in methanol at room temperature and the same solvent can be used for the next stage of the reaction. The tertiary carbinamine is preferably a tri (substituted alkyl) methylamine in which the alkyl group is substituted by a functional group such as hydroxyl, for example tris (hydroxymethyl) methylamine. The resulting dendritic molecule has three limbs each having three functionally substituted branches and is formed in greater than 95% yield.

The hydroxy-functional dendrimer product can be used as a cross-linking agent in for example coating compositions.

The process of the invention can also be used to prepare dendritic polymers containing ester linkages. For example, a carboxylic acid can be reacted with carbonyl diimidazole to produce an imidazolide, which can then be reacted with a compound having at least two primary hydroxyl groups and one group such as a carboxylic acid group which is not reactive with the imidazolide groups but is reactive with carbonyl diimidazole, thereby forming a "wedge" polyester molecule which can be further reacted with carbonyl diimidazole to start the next generation of dendrimer growth. Similarly, a polycarboxylic acid can be reacted with carbonyl diimidazole to produce an imidazolide, which can then be reacted with a compound (B) having one primary hydroxyl group) and more than one group such as carboxylic acid which is not reactive with the imidazolide group but which is reactive with carbonyl diimidazole. For example the compound (B) can be N-(2-hydroxyethyl)iminodioacetic acid. A dendritic polyester can thereby be produced by divergent growth. The reactions involving hydroxycarboxylic acids may need to be carried out in a more polar solvent such as dimethyl sulphoxide or dimethyl formamide.

A dendritic aromatic polyester can be produced by reaction of a dihydroxybenzoic acid, for example 3,5-dihydroxybenzoic acid, with the imidazolide of a carboxylic acid such as benzoic acid. This esterifies the hydroxyl groups but leaves the carboxylic acid group of the dihydroxybenzoic acid free for reaction with CDI to produce an imidazolide which can be further reacted with dihydroxybenzoic acid to produce a dendritic "wedge".

In a process for preparing a dendritic polymer containing ester and amide linkages, a carboxylic acid is reacted with carbonyl diimidazole as described above. The resulting imidazolide is reacted with an aminoalcohol having two primary alcohol groups and one secondary amine group, for example diethanolamine, forming a "wedge" molecule containing ester linkages and one secondary amine group. This can be reacted with a cyclic carboxylic acid anhydride as described above in connection with polyamide preparation, forming a carboxylic acid-functional molecule which can be reacted with carbonyl diimidazole to produce an imidazolide. This imidazolide can be further reacted with diethanolamine to produce a larger "wedge" as shown below or with a poly (primary alcohol) such as trimethylolpropane, pentaerythritol or butanediol to produce a dendrimer.

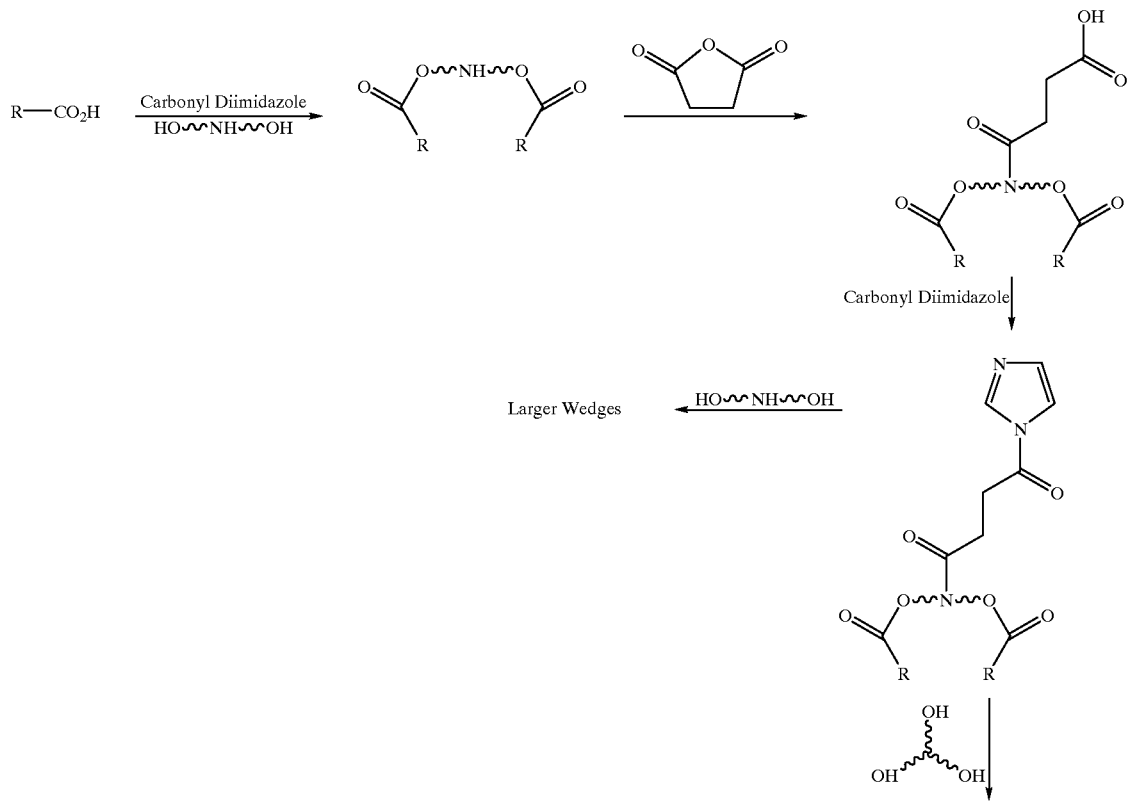

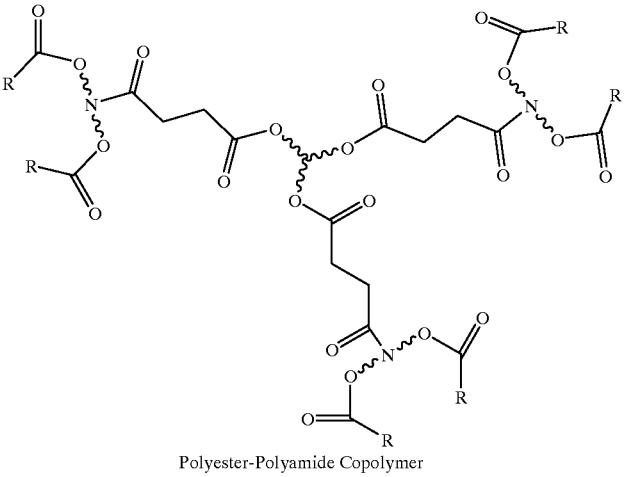
Polyester-Polyamide Copolymer

The process of the invention can readily be used to form dendritic polymers containing more than one type of linkage selected from carbonate, urethane, urea, amide and ester linkages. In particular, dendritic polymers can be formed containing different linkages in different generations of the dendritic polymer. For example, a secondary or tertiary alcohol can be reacted successively with carbonyl diimidazole and a triol containing two primary and one secondary alcohol group, for example 1-(N,N-bis(2-hydroxyethyl)-amino)-2-propanol to form a "wedge" containing carbonate linkages and a secondary alcohol group; these reactions can if desired be repeated alternately to form a large "wedge". The "wedge" can then be reacted with carbonyl diimidazole followed by reaction with a poly(primary amine), for example tris(2-aminoethyl) amine, to form a dendritic polymer containing carbonate and urethane linkages as shown in the following reaction scheme.

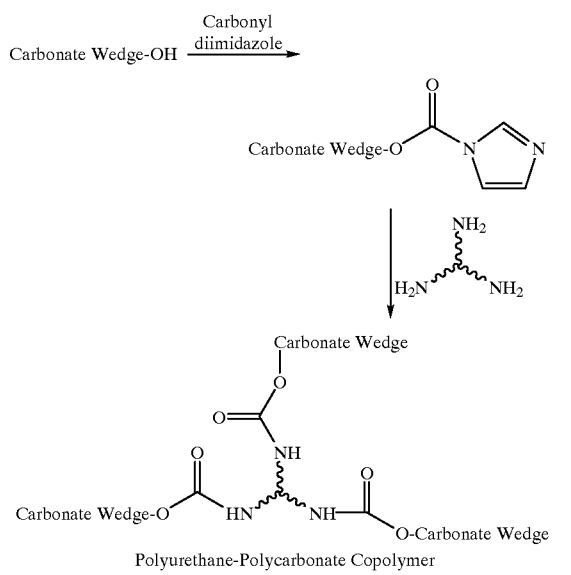
Polyurethane-Polycarbonate Copolymer

Alternatively, a secondary or tertiary alcohol can be reacted successively with carbonyl diimidazole and a compound (C2) containing two primary amine groups and one secondary alcohol group, for example 2-hydroxy-propane-1,3-diamine, to form a "wedge" containing urethane linkages and a secondary alcohol group, optionally repeating the reactions alternately to form a larger "wedge". The "wedge" can then be reacted with a polyol having primary hydroxyl groups such as trimethylolpropane, triethanolamine or dipentaerythritol to form a dendritic polymer containing urethane and carbonate linkages as shown below:

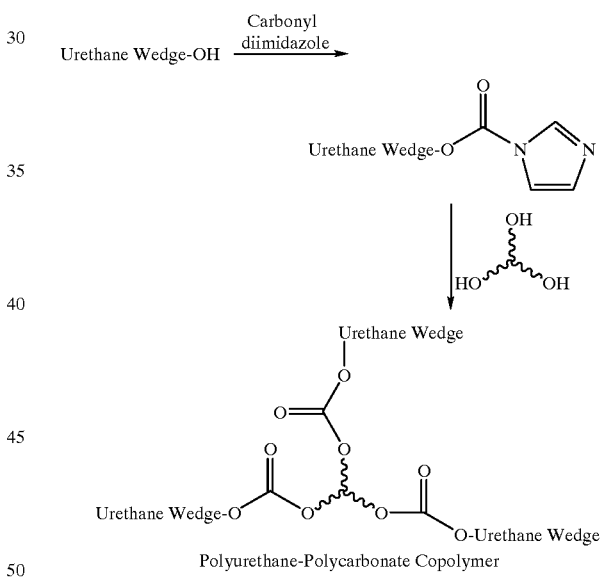
Polyurethane-Polycarbonate Copolymer

Dendritic polymers containing urea linkages and carbonate or urethane linkages can be produced by the reaction of the imidazole carboxamide of a primary amine with a compound (C2) containing at least two amine groups (which can be primary and/or secondary amine groups) and an alcohol group, preferably a secondary alcohol group, for example N-(2-hydroxypropyl) ethylene diamine. Both the primary and the secondary amine group will react with the imidazole carboxamide, forming urea linkages. The alcohol group will not react in the absence of strong base. An alcohol-functional wedge is thus formed, which can be reacted with CDI and then with an amine or an alcohol to form urethane or carbonate linkages respectively.

The process of the invention can alternatively be used to produce segmented copolymers containing "wedges" of different type, for example polyamide wedges with polycarbonate wedges or polycarbonate wedges with polyurethane wedges. In this case a first dendritic wedge (A) containing an imidazolide group is reacted with a compound (B) containing a functional group which is reactive with that imidazolide group and another functional group which is not reactive or is much less reactive with that imidazolide group but which is capable of subsequent reaction with a different imidazolide group of a different wedge. In general the compound or polymer (B) can contain a functional group (III) which does not react with the imidazolide group (I) under the reaction conditions used but is capable of reaction with an imidazolide group (I) under different reaction conditions. This can be as well as or instead of a functional group (III) which is substantially unreactive with imidazolide groups but which is reactive with other reagents such as carboxyl diimidazole. For example a compound containing a primary amine group and a primary alcohol group can be reacted with a first dendritic "wedge", which may for example be a polyamide containing

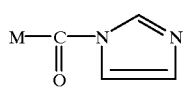

groups. If the aminoalcohol is used in at least an equimolar amount, it will react substantially entirely through its primary amine group. The resulting product can then be reacted with a second dendritic "wedge", which may for example be a polycarbonate containing

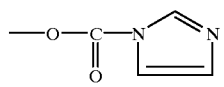

groups derived from a secondary alcohol group, in the presence of a base such as KOH so that the second dendritic wedge becomes bonded to the product through a carbonate linkage. The aminoalcohol can be a simple aminoalcohol such as ethanolamine or can contain a further functional croup such as a secondary amine group or secondary alcohol croup which does not react in either of the above process steps but which can subsequently be reacted. For example the aminoalcohol can be N-(2-hydroxyethyl) ethylene diamine. The reaction product containing two dendritic wedges then contains a secondary amine group which can be reacted successively with (i) a cyclic carboxylic anhydride such as succinic anhydride, (ii) CDI to produce imidazolide groups and (iii) a compound containing two or three reactive groups such as amine or alcohol groups which are reactive with the imidazolide groups, thereby producing a dendrimer containing two or three polyamide "wedges" and two or three polycarbonate "wedges".

Dendritic polymers containing two or more different types of linkage can alternatively be formed by divergent growth. For example, a disecondary or ditertiary alcohol such as pentane-2,4-diol or 2,5-dimethylhexane-2,5-diol can be reacted with carbonyl diimidazole to form an imidazolide followed by reaction with a triol (IIa) having one primary and two secondary alcohol groups to form a first generation dendrimer having carbonate linkages and secondary alcohol groups. This can be further reacted with carbonyl diimidazole and then with a primary disecondary triamine (IIb) to produce a second generation dendrimer having carbonate linkages nearer the core, urethane linkages in the branches and secondary amine groups at the surface. Alternatively, a compound having one primary amine group and two secondary hydroxyl groups can be used in place of (IIb) to produce a second generation dendrimer having carbonate and urethane linkages but with hydroxyl groups at the surface. The compound (IIb) can alternatively be replaced by any primary amine containing no other groups reactive with the imidazolide group; for example it can be unsubstituted to leave hydrocarbon groups at the surface or may be fluorinated to give a low-surface-energy polymer.

A modified process according to the invention can be used to prepare dendritic polymers containing urethane and amide linkages. A secondary or tertiary alcohol ROH is reacted with carbonyl diimidazole followed by reaction with a triamine having two primary and one secondary amine groups, for example diethylene triamine, to form a "wedge" having urethane linkages and a secondary amine group. This "wedge" can be reacted with a dicarboxylic acid anhydride, for example succinic anhydride, to introduce a carboxyalkyl group joined via an amide linkage, as shown below. The carboxylic acid groups introduced can then be reacted with carbonyl diimidazole and the resulting imidazolide can be reacted with a poly(primary amine) such as tris(2-aminoethyl) amine to produce a dendritic polymer containing urethane and amide linkages.

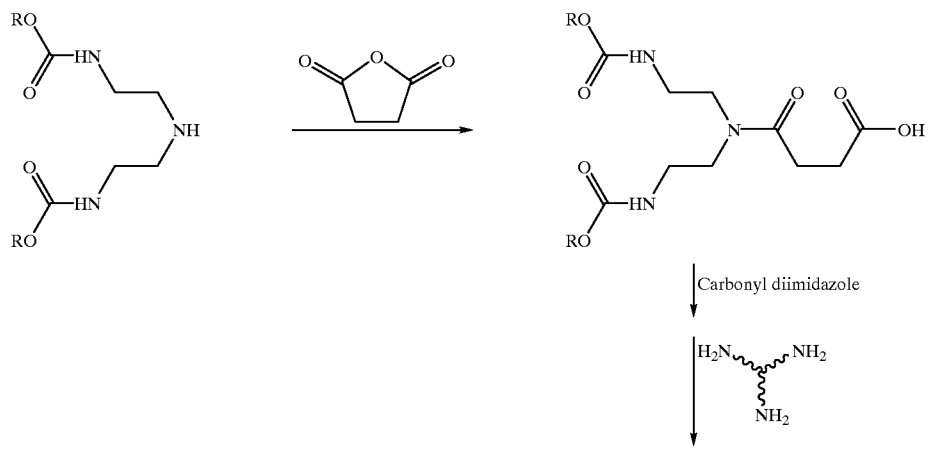

-continued

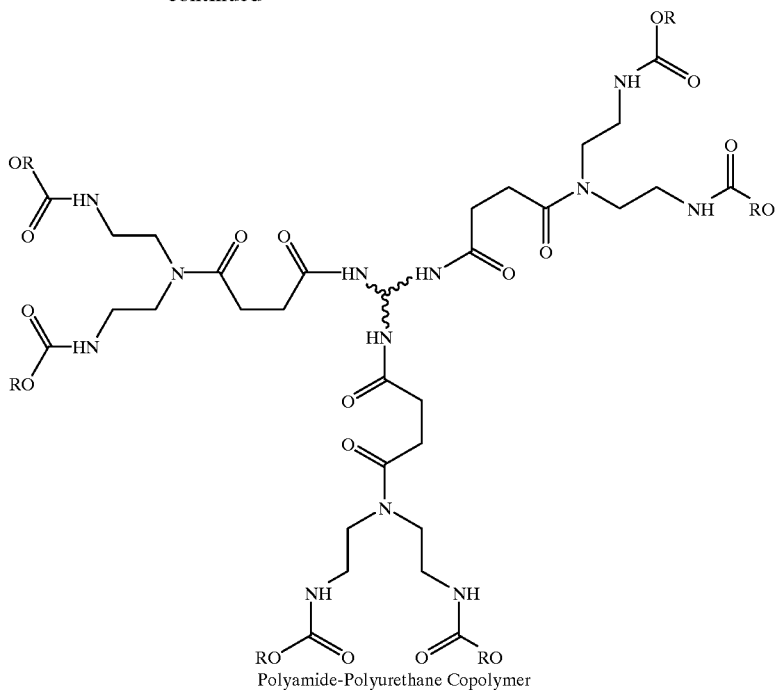
Polyamide-Polyurethane Copolymer

The tri(primary amine) used in the above process can if desired be replaced by a polyol having primary alcohol groups such as trimethylolpropane or dipentaerythritol which reacts with the imidazolide groups to form ester groups, thereby forming a dendritic polymer containing urethane, amide and ester groups.

A modification of the above process can be used to produce "wedge" molecules containing reactive groups which are useful intermediates in dendrimer synthesis. If the group R is a tertiary alkyl, the tertiary alkyl carboxylate moiety is capable of being removed by heating, leaving free primary amino groups. For example, t-butanol can be reacted successively with (i) CDI, (ii) diethylene triamine, (iii) succinic anhydride, (iv) CDI and (v) diethylene triamine to produce a dendritic polyamide "wedge" containing one secondary amine group and four t-butyl carbamate groups, which can be converted by heating to four primary amine groups as shown below.

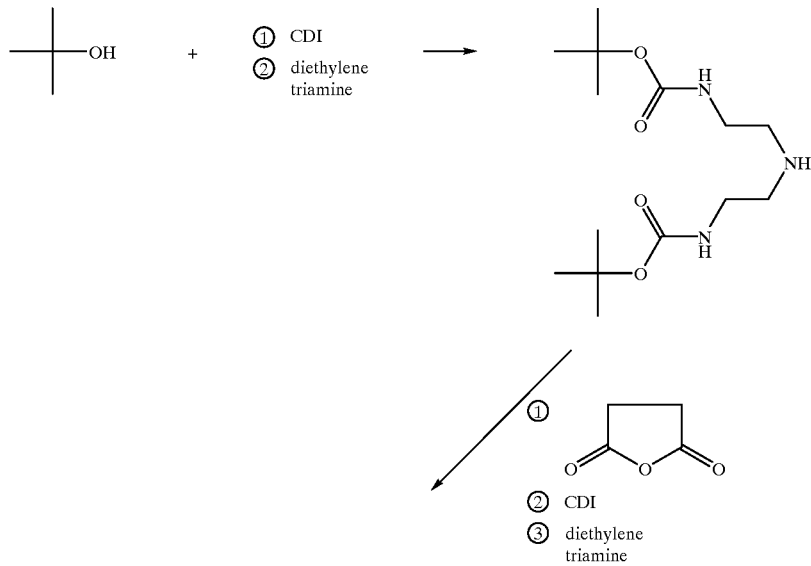

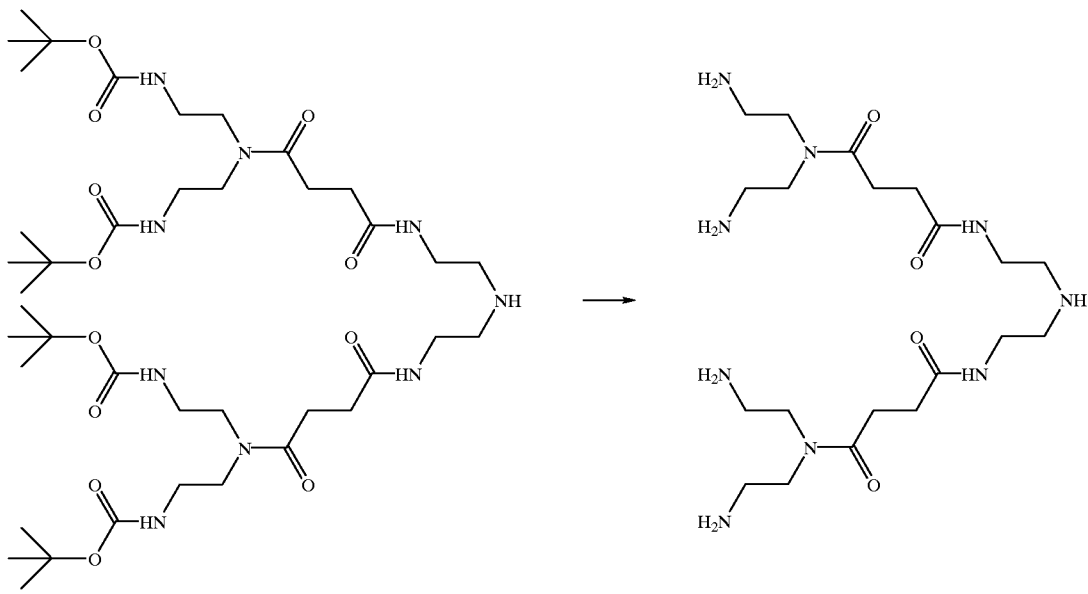

The "wedge" containing four primary amine groups and one secondary amine group can be used as a compound (B) in the process of the invention for reaction with a compound or polymer (A) containing an imidazolide group preferably derived from a carboxylic acid or alternatively from an alcohol or amine. This reaction is useful in dendrimer synthesis since two generations of dendritic growth are introduced in a single reaction. The carboxylic acid used to form the imidazolide may contain any desired substituent, which will be present as a surface substituent in the dendritic polymer produced. Alternatively the "wedge" containing four primary amine groups and one secondary amine group can itself be used as a curing agent, for example for epoxy resins.

An alternative type of dendritic copolymer which can be produced according to the invention is a "random" or "statistical" dendrimer copolymer. For example, this can be accomplished by a convergent route when (in the formation of an amide) a mixture of two or more secondary amines is used to ring open an anhydride (or a mixture of anhydrides) to form a distribution of acid functional "wedges". These are reacted with CDI to form the imidazolide followed by reaction with a diprimary secondary triamine or a mixture of such triamines (eg diethylene triamine, dipropylene triamine, bishexamethylene triamine,) to couple the distribution in a random way. The result would be a distribution of secondary amine functional wedges, all with a random array of coupled groups. Such wedges can undergo further dendrimer growth and/or can be linked by a polyfunctional core molecule or a mixture of such core molecules.

Thus the invention includes a dendritic polymer comprising at least two limbs radiating from a core radical, each of said limbs comprising at least two branches, characterised in that the branches contain a linkage selected from carbonate, urethane, urea, amide and ester linkages and that each limb has a linkage selected from carbonate, urethane, urea, amide and ester linkages between the branches and the core, and that the polymer is a statistical copolymer comprising dendritic polymer molecules containing at least two different branches in the differing ratios, different branches containing the same linkages but containing different organic radicals.

The dendritic polymers of the invention are usually liquids of low viscosity. Some of the dendritic polymers, particularly those having urethane and amide linkages, are solid at room temperature but these too have low viscosity when in solution. Dendritic polymers have an unusual viscosity to molecular weight relationship; unlike other polymers, the viscosity of a liquid dendrimer or a solution of a dendrimer does not necessarily increase with increasing molecular weight. The melting point and Tg of dendritic polymers can readily be varied according to the present invention, as explained in more detail following Example 31. The dendritic polymers of the invention, particularly those having reactive functional groups at the surface, can be used as ingredients of high solids coatings and sealants; they can be cured through their functional groups to form solid coating films. They can also be used as reactive plasticisers in thermoplastic compositions. The dendritic polymers can alternatively be used as rheology modifiers in coating and sealant compositions, causing a greater reduction of viscosity than a similar amount of volatile solvent.

Since the properties of a dendritic polymer depend largely on the groups at its surface, water-soluble dendritic polymers can be produced having hydrophilic groups for example hydroxyl or amine groups at the surface even if the core of the dendritic polymer is hydrophobic. Curing of the coating by reaction of the hydrophilic groups can form a hydrophobic coating from a water-based composition.

Dendrimers having reactive functional groups at the surface can be used to bind biological reagents such as enzymes or antigens, as described for example in U.S. Pat. No. 5,229,490, providing a high concentration of the biological reagent in a low molecular volume. Alternatively, new colourants can be formed by attaching chromophores at the surface of the dendrimer.

Many of the intermediate products produced by the process of the invention are new compounds; in particular the "wedge" compounds produced during convergent growth of a dendritic polymer. For example the compounds of the formulae:

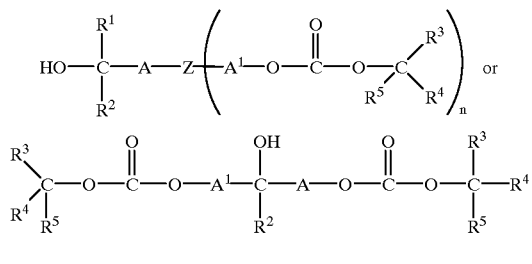

where $R^1$, $R^3$ and $R^4$ are each alkyl or aryl groups which can be substituted, $R^2$ and $R^5$ are each selected from hydrogen or an alkyl group which can be substituted, A and $A^1$ each represent a divalent organic linkage, n is an integer of at least 2 and Z is a core radical of valency n+1, are new and useful compounds. In particular they are useful in the production of a dendritic polycarbonate. Similarly compounds of the formula:

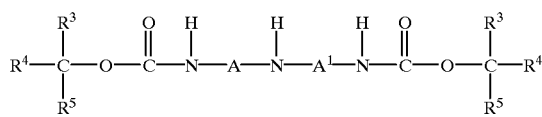

in which $R^3$, $R^4$, $R^5$, A and $A^1$ have the meanings given above are new compounds useful in the preparation of dendritic polymers containing urethane linkages. Compounds of the formula:

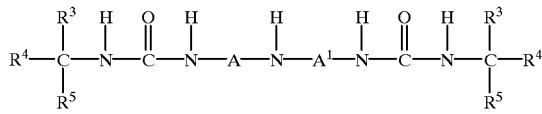

are new compounds useful in the preparation of dendritic polymers containing urea linkages.

These "wedge" compounds have some dendritic character and generally have a reactive functional group such as a hydroxyl or amine group at the focal point of the wedge. They can be used themselves in coating, adhesive and sealant compositions as reactive components, in particular as rheology-modifying additions which become bound into the composition when it is cured. Amine groups at the focal point of a "wedge" compound can for example react with epoxide groups, or they can react with acrylate groups in a Michael reaction. Alternatively, the "wedge" compounds can be modified to incorporate them into a polymer. They can for example be reacted with a compound such as acrylic or methacrylic acid or acryloyl or methacryloyl chloride to introduce ethylenic unsaturation and subsequently polymerised or copolymerised with ethylenically unsaturated comonomers such as acrylic and/or methacrylic esters, styrene, olefins or vinyl compounds. Alternatively the "wedge" molecules can be modified to introduce chain transfer agent groups, and subsequently used as chain transfer agents during ethylenic polymerisation, whereby the dendritic "wedge" molecule becomes incorporated at the end of polymer chains. The "wedge" molecules can be bonded to natural polymer, for example they can be bonded to cellulose through the —$CH_2OH$ groups of cellulose.

Intermediate products produced during divergent growth of a dendritic polymer are also new, for example a compound of the formula:

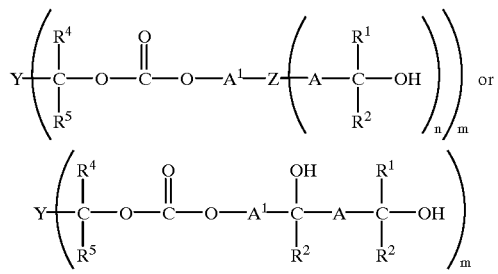

where $R^1$, $R^2$, $R^4$, $R^5$, A, $A_1$, Z and n are defined as above and Y is a core radical of valency m which is at least 2 is new and is the first generation of a dendritic polycarbonate. Similarly, a compound of the formula:

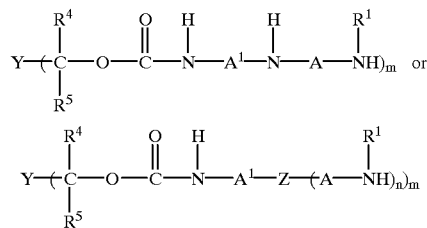

where $R^1$, $R^4$, $R^5$, A, $A^1$, Y, Z, n and m are defined as above is new and is the first generation of a dendritic polyurethane.

In some cases the first generation dendrimer formed by the reaction of an imidazolide with a polyvalent primary alcohol or polyvalent primary amine has many of the characteristics of a dendrimer, and these compounds are in general new. The invention thus includes compounds of the formula:

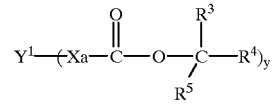

in which $Y^1$ is a core radical of valency y which is at least 3, Xa is —O— or —NH— and $R^3$, $R^4$ and $R^5$ are defined above. Particularly preferred compounds of the above formula are those in which y is at least 4, for example the compounds where y=6 derived from dipentaerythritol, and those in which at least one of the groups $R^3$, $R^4$ and $R^5$ is a branched alkyl group, for example the compounds derived from 2,6-dimethyl-4-heptanol where both $R^3$ and $R^4$ are isopropyl groups.

The process of the invention can be used to prepare polymers tipped with functional groups. A compound or polymer (A) containing at least two imidazolide groups as chain terminating groups can be reacted with a compound (B) in which the functional group (III) which is unreactive with the imidazolide groups (I) is the desired functional group for tipping the polymer, for example hydroxyl, thiol or carboxylic acid groups. (B) preferably contains at least two groups (III). For example a polymer tipped with carboxylic acid groups or alcohol groups can be reacted with CDI to produce an imidazolide and this can be reacted with a compound containing an amine group and the desired functional tipping groups. In one preferred process the imidazolide is the reaction product of a carboxylic acid-terminated polymer with carbonyl diimidazole and the compound (B) is an aliphatic compound such as tris(methylol)

melamine containing one primary amine group at least two hydroxyl groups, and the reaction of the carboxylic acid-terminated polymer with carbonyl diimidazole and the reaction of the polymer (A) with the compound (B) are carried out in an alcohol solvent, generally an alcohol having 1 to 5 carbon atoms, without isolation of the polymer (A).

Alternatively, a polymer containing primary amine groups can be reacted with an imidazolide substituted with alcohol or thiol groups. This process is particularly convenient for tipping a polymer with thiol groups. Amine-terminated polymers are well known, for example the amine-terminated polyethers sold under the Trademark "Jeffamine". These can be reacted with the imidazolide of a mercaptoalkyl carboxylic acid, e.g. the reaction product of 3-mercaptopropionic acid with CDI. The thiol-tipped polymer formed, which generally have the formula:

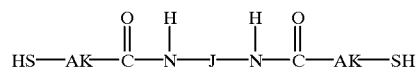

in which each group AK represents an alkylene group having 1 to 4 carbon atoms and J represents a polymer chain of molecular weight 200 to 10,000, preferably a polyether of molecular weight 400 to 3,000, is particularly useful as a sealant for aerospace. Polymers tipped with thiol groups can readily be cured to elastomers with good resistance to weathering, oil, ozone and water.

The invention is illustrated by the following Examples.

Abbreviations used in Examples

AEAE—2-(2-Aminoethylamino)ethanol
AEIPA—2-Aminoethyldiisopropanolamine
BA—Benzoic acid
BEHA—Bis(2-ethylhexyl)amine
BID—Biscarbonylimidazolide of 2,5-dimethyl-2,5-hexanediol
BIH—Biscarbonylimidazolide of 2,5-hexanediol
CDI—1,1'-Carbonyldiimidazole
CIB—Carbonylimidazolide of t-butanol
CIH—Carbonylimidazolide of 2,6-dimethyl-4-heptanol
DHBA—3,5-Dihydroxybenzoic acid
DPA—Dipropylamine
DTA—Diethylene triamine
HEAP—1-[N,N-bis(2-hydroxyethyl)amino]-2-propanol
HEIPA—2-Hydroxyethyldiisopropanolamine
KOH—Potassium Hydroxide
MAA—Mercaptoacetic acid
PAE—2-(propylamino)ethanol
PP—2-Propyl-1-pentanol
PrD—1,3-Propanediol
SAn—Succinic Anhydride
TAEA—Tris-(2-aminoethyl)amine
TEA—Triethanolamine
THAM—Tris(hydroxymethyl)aminomethane
THF—Tetrahydrofuran
TIPA—Triscarbonylimidazolide of triisopropanolamine
TMP—Trimethylol propane

EXAMPLE 1

1(a) 1-Imidazolecarboxylate of 2,6-Dimethyl-4-heptanol (CIH)

A solution of 2,6-dimethyl-4-heptanol (20.00 g, 0.14 mol), 1,1'-carbonyldiimidazole (CDI) (25.32 g, 0.16 mol) and potassium hydroxide (0.66 g, 12 mmol) in toluene (100 ml) was heated at 50–60° C. under nitrogen for 5 hours and then allowed to cool overnight. The precipitated solid was removed by filtration and the filtrate concentrated in vacuo to give the product as a white crystalline solid (30.74 g, 93%).

1(b) Reaction of CIH with 1-[N,N-Bis2-hydroxyethyl) amino]-2-propanol (HEAP)—(CIH-HEAP-OH Synthesis)

A solution of HEAP (1.36 g, 8.33 mmol), CIH (3.97 g, 16.70 mmol) and potassium hydroxide (0.4 g, 7.30 mmol) in toluene (50 ml) was heated at 50–60° C. under nitrogen for 4 hours and then allowed to cool overnight. The crystallised solid was removed by filtration and the filtrate concentrated in vacuo. The residue was dissolved in dichloromethane, washed with water, dried (MgSO$_4$), filtered and concentrated in vacuo to give the dendritic "wedge" product (CIH-HEAP-OH) as a clear viscous liquid (3.88 g, 92.4%).

EXAMPLE 2

2(a) Derivatisation of a Hydroxyl-Functional Polycarbonate Wedge with CDI

CDI (0.32 g, 2.0 mmol) and KOH (0.10 g, 1,8 mmol) were added to a solution of CIH-HEAP-OH prepared in Example 1(b) (1.0 g, 2.0 mmol) in toluene (10 ml). The reaction mixture was heated at 50–60° C. under nitrogen for 5 hours and then allowed to cool overnight. The crystallised solid was removed by filtration and the filtrate concentrated in vacuo. The residue was dissolved in dichloromethane, washed with water, dried (MgSO$_4$), filtered and concentrated in vacuo to give the product (CIH-HEAP-Imid) as a clear viscous liquid (1.12 g, 94%)

2(b) Formation of a Second Generation Polycarbonate Wedge—CIH-HEAP-HEAP-OH

CIH-HEAP-Imid (4.0 g, 6.7 mmol) (as prepared in Example 2a) and KOH (0.2 g, 3.6 mmol) were added to toluene 50 ml) A solution of HEAP (0–55 g, 3.33 mmol) in toluene (10 ml) was slowly added to the mixture and the solution was heated at 55–60° C. under nitrogen for 5 hours. The react on mixture was allowed to cool overnight. The crystallised solid was removed by filtration and the filtrate concentrated in vacuo. The residue was dissolved in dichloromethane, washed with water, dried (MgSO$_4$), filtered and concentrated in vacuo to give the product (CIH-HEAP-HEAP-OH) as a clear viscous liquid (3.80 g, 95%)

EXAMPLE 3

Dendrimer Formation by Convergent Growth—
CIH-HEAP-HEAP-TMP

CDI (0.55 g, 3.4 mmol) and KOH (0.1 g, 1.8 mmol) were added to a solution of CIH-HEAP-HEAP-OH (4 g, 3.33 mmol) (as prepared in Example 2(b)) in toluene 50 ml. The reaction mixture was heated to 50–60° C. under nitrogen or 5 hours. Trimethylolpropane (0.15 g, 1.11 mmol) was added and the mixture was stirred for a further 3 hours. The reaction mixture was allowed to cool overnight. The crystallised solid was removed by filtration and the filtrate concentrated in vacuo. The residue was dissolved in dichloromethane, washed with water, dried (MgSO$_4$), filtered and concentrated in vacuo to give the dendrimer product (CIH-HEAP-HEAP-TMP) shown below as a clear viscous liquid (3.96 g, 92%)

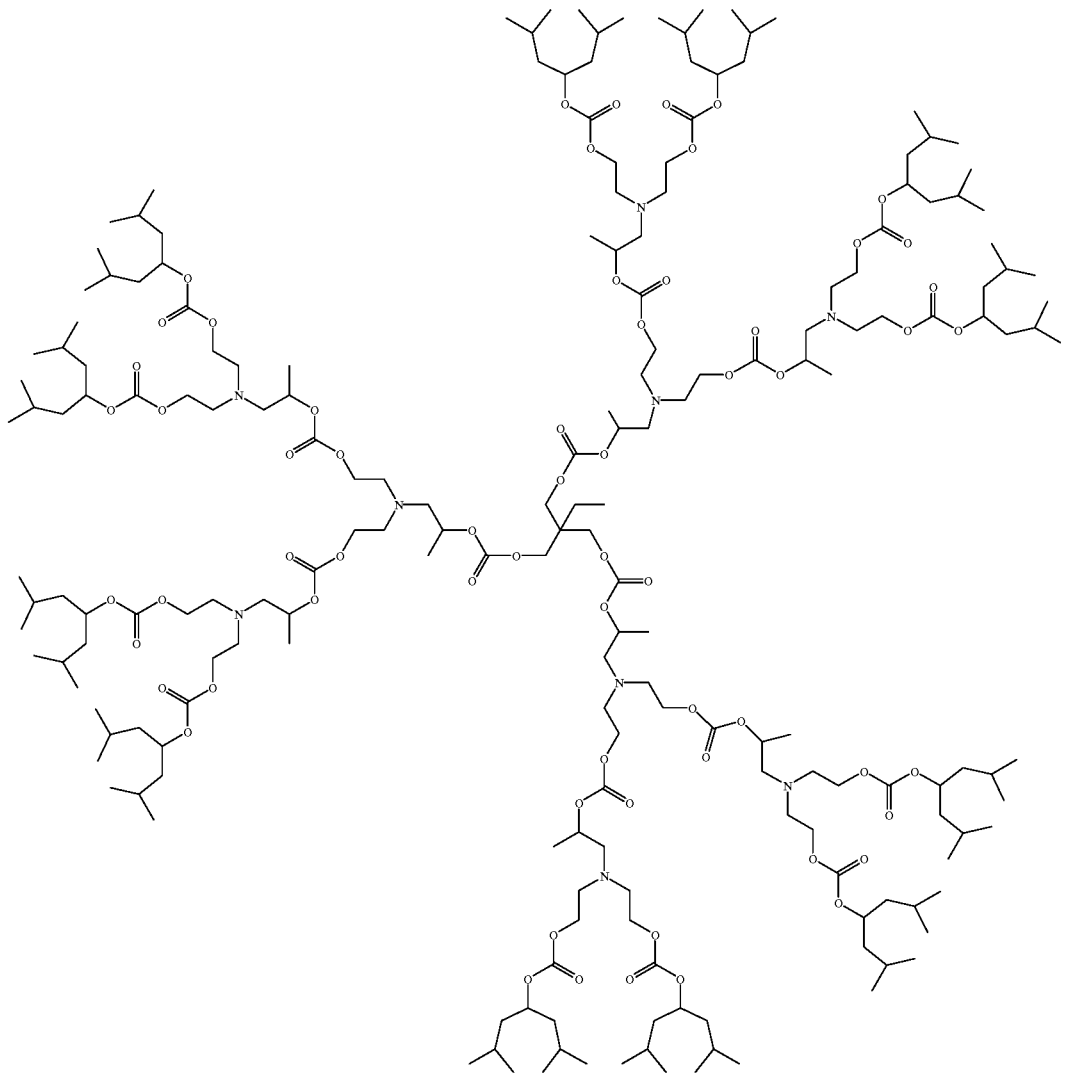

EXAMPLE 4

Reaction of CIH with TMP—Dendrimer Formation

2-Ethyl-2-hydroxymethyl-1,3-propanediol (trimethylol propane, TMP) (1.00 g, 7.4 mmol), CIH prepared in Example 1(a) (5.86 g, 24.6 mmol (1:1.1 ratio of CIH to hydroxyl groups)) and potassium hydroxide (0.20 g, 3.7 mmol) in toluene (70 ml) were heated at 80° C. for 5–6 hours and allowed to cool overnight. The solution was concentrated in vacuo. The residue was dissolved in dichloromethane, washed with water, dried (MgSO$_4$), filtered and concentrated in vacuo to give the product as clear viscous liquid (3.93 g, 83.6%).

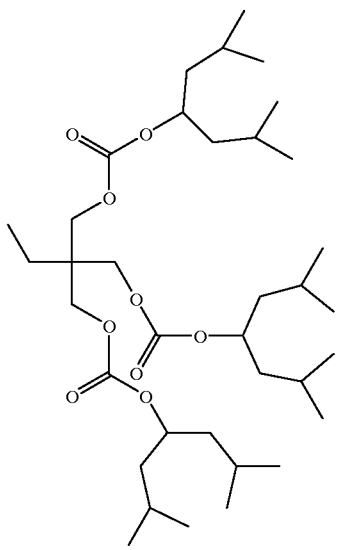
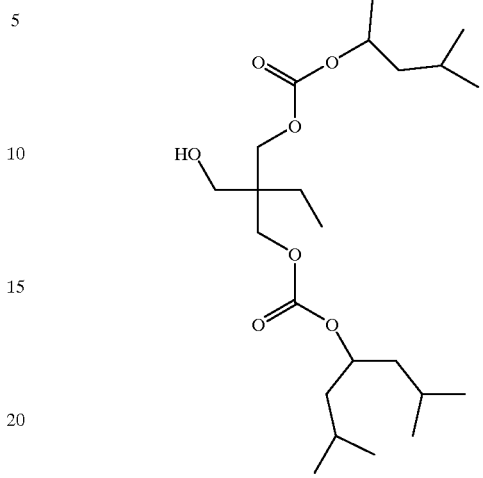

EXAMPLE 5

5(a) Reaction of CIH with TMP—Dicarbonate formation

A solution of CIH prepared in Example 1(a) (7.10 g, 30.0 mmol) in t-butanol (20 ml) was added dropwise to a solution of 2-ethyl-2-hydroxymethyl-1,3-propanediol (2.00 g, 15.0 mmol) and potassium hydroxide (0.2 g, 3.6 mmol) in t-butanol (15 ml) at 60° C. and stirred for 6 hours, then allowed to cool overnight. The reaction mixture was concentrated in vacuo. The residue was dissolved in dichloromethane, washed with water, dried (MgSO$_4$), filtered and concentrated in vacuo to give a colorless gum which was purified by flash chromatography on silica [ethyl acetate/petroleum ether (b.p. 40–60° C.), 1:1] to give the dicarbonate CIH-TMP-OH (shown below) as a colourless gum (4.61 g, 65%).

5(b) Dendrimer Formation

A solution of CIH-TMP-OH (2.00 g, 4.2 mmol) in toluene (40 ml) was added dropwise over 30 minutes to a solution of 1,1'-carbonyldiimidazole (1.36 g, 8.4 mmol) and potassium hydroxide (0.40 g, 7 mmol) in toluene (40 ml) at 60° C. and stirred for 6 hours and cooled. The precipitated imidazole as removed by filtration, the filtrate was washed with water, dried (MgSO$_4$), filtered and concentrated in vacuo to give CIH-TMP-Imid as a white solid (2.21 g, 92%). A solution of CIH-TMP-Imid (0.50 g, 0.89 mmol) and tris (2-aminoethyl)amine (43 mg, 0.30 mmol) in toluene was stirred at room temperature for 6 hours. The precipitated solid was removed by filtration and the filtrate concentrated in vacuo to produce the dendrimer shown below having carbonate and urethane linkages (0.45 g, 92%).

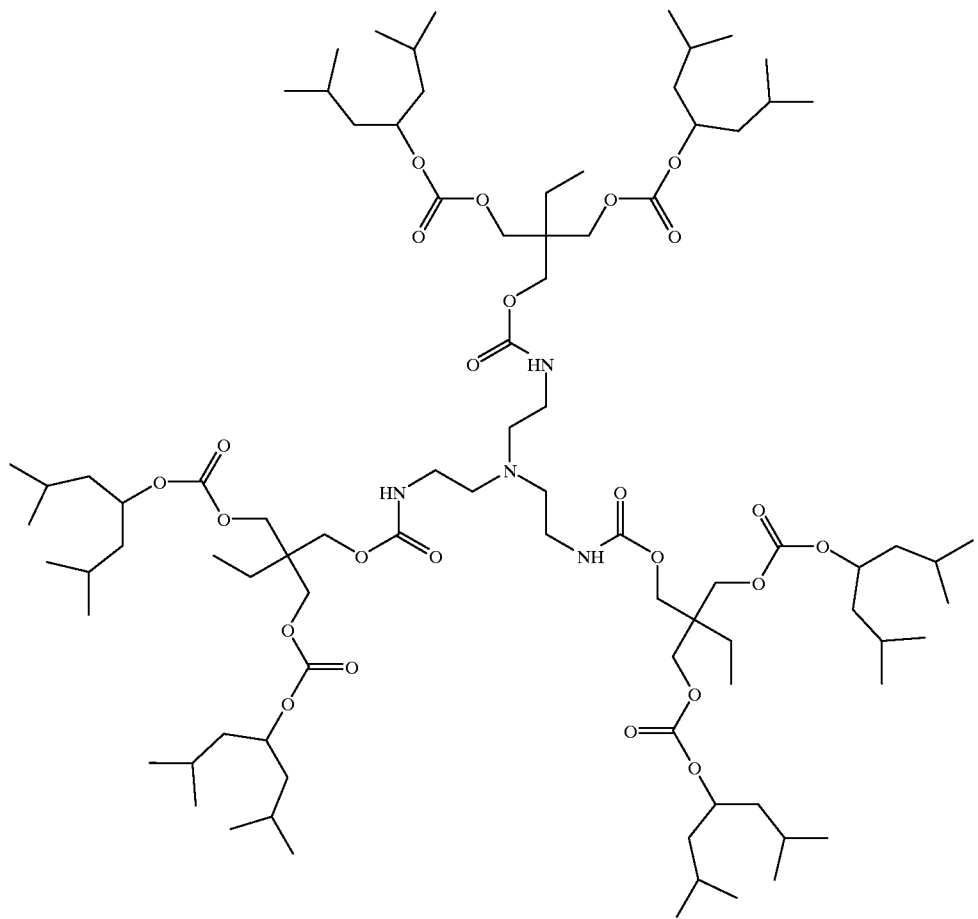

EXAMPLE 6

Reaction of Dipentaerythritol with CIH

Dipentaerythritol (0.50 g, 1.97 mmol), CIH prepared in Example 1(a) (2.81 g, 11.80 mmol) and potassium hydroxide (66 mg, 1.18 mmol) in DMSO (20 ml) and toluene (5 ml) were heated at 50–60° C. for 4 hours and allowed to cool overnight. The reaction mixture was diluted with dichloromethane, washed with water, dried (MgSO$_4$), filtered and concentrated in vacuo to give the dendrimer shown below as a yellow gum (2.40 g, 96%).

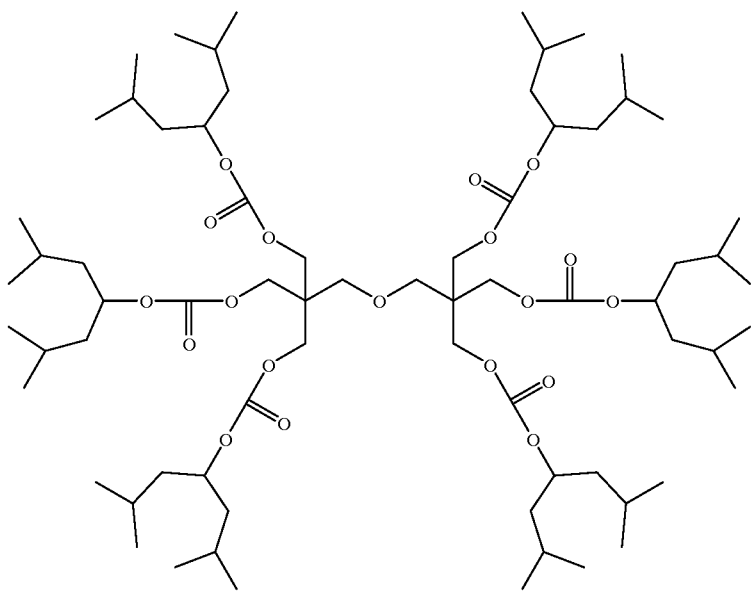

EXAMPLE 7

7(a) Carbonyl Imidazolide of t-Butanol (CIB)

A solution of t-butanol (5.0 g, 6.75 mmol), 1,1'-carbonyldiimidazole (10.0 g, 61.7 mmol) and potassium hydroxide (0.3 g, 5.3 mmol) in toluene (100 ml) was heated at 50–60° C. under nitrogen for 5 hours and then allowed to cool overnight. The crystalline solid that formed on cooling was removed by filtration and the solvent was removed in vacuo. The residue was dissolved in dichloromethane, washed with water, dried (MgSO$_4$), filtered and concentrated in vacuo to give the product as a white solid (10.19 g, 93%).

7(b) Reaction of CIB with TMP—Dicarbonate Formation

A solution of CIB (5.00 g, 30 mmol) in tertiary butanol (20 ml) was added dropwise over 30 minutes to a solution of TMP (2.00 g, 15 mmol) and potassium hydroxide (0.20 g, 3.6 mmol) in tertiary butanol (20 ml) at 60° C. and heated for 6 hours then cooled. The reaction mixture was concentrated in vacuo. The residue was dissolved in toluene, washed with water, dried (MgSO$_4$), filtered and concentrated in vacuo. The residue was purified by flash silica chromatography [ethyl acetate/petroleum ether (b.p. 40–60° C.), 1:1] to give CIB-TMP-OH as a white solid (3.38 g, 68%).

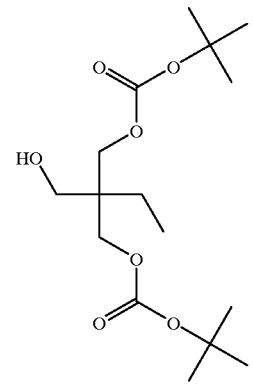

7(c) Dendrimer Formation

A solution of the CIB-TMP-OH (1.80 g, 5.4 mol), prepared in example 7b, in toluene (20 ml) was added dropwise over 30 minutes to a solution of 1,1'-carbonyl diimidazole (1.75 g, 10.8 mmol) and potassium hydroxide (0.30 g, 5.4 mmol) in toluene (20 ml) and heated to 60° C. for 5 hours then cooled. The reaction mixture was filtered. Tris (2-aminoethyl)amine (0.26 g, 1.78 mmol) was added to the filtrate and stirred at room temperature for 6 hours. The precipitated imidazole was removed by filtration. The filtrate was washed with water, dried (MgSO$_4$), filtered and concentrated in vacuo to produce a dendrimer having urethane and carbonate linkages as a colourless gum (2.15 g, 98%).

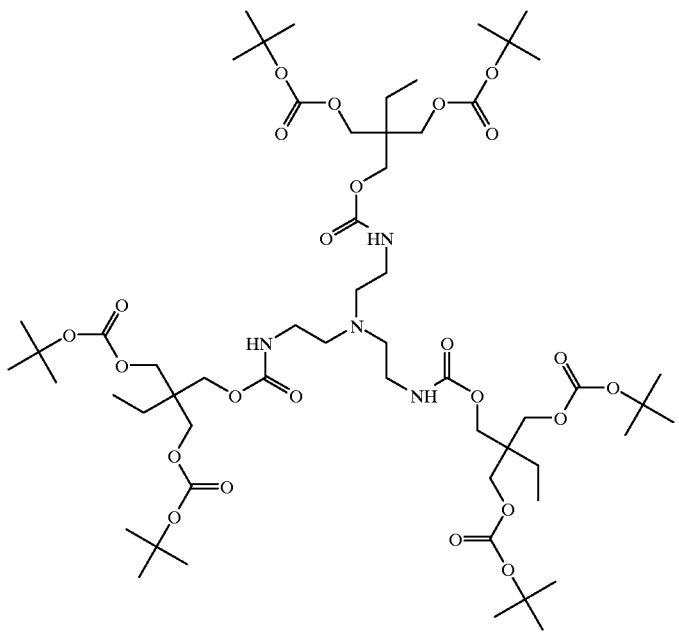

EXAMPLE 8

8(a) Biscarbonylimidazolide of 2,5-Dimethylhexane-2,5-diol (BID)

A solution of 2,5-dimethylhexane-2,5-diol (5.0 g, 34 mmol), 1,1'-carbonyldiimidazole (11.1 g, 69 mmol), and potassium hydroxide (160 mg, 3 mmol) in toluene (25 ml) was heated at 50–60° C. under nitrogen for 5 hours and then allowed to cool overnight. The solvent was removed in vacuo. The residue was dissolved in dichloromethane, washed with water, dried ($MgSO_4$), filtered and concentrated in vacuo to give the product as a white solid (10.82 g, 95%).

8(b) Formation of THAM-AEIPA-BID-Dendrimer

A solution of BID prepared in Example 8a (2 g, 5.99 mmol), 2-amninoethyldiisopropanolamine (AEIPA) (2.11 g, 12 mmol) in THF (40 ml) was stirred at room temperature for 6 hours and then filtered. 1,1'-Carbonyl diimidazole (3.88 g, 24 mmol) and potassium hydroxide (34 mg, 0.6 mmol were then added to the filtrate and heated at 60° C. for 6 hours and cooled. The reaction mixture was filtered. Trishydroxyaminomethane (THAM) (2.90 g, 24 mmol) was added to the filtrate and stirred at room temperature for 6 hours. The reaction mixture was concentrated in vacuo. The residue was extracted with hot toluene to give the product as a white solid.

EXAMPLE 9

9(a) Biscarbonylimidazolide of Hexane-2,5-diol (BIH)

A solution of hexane-2,5-diol (5.00 g, 42 mmol), 1,1'-carbonyldiimidazole (13.75 g, 85 mmol) and potassium hydroxide (200 mg, 3.75 mmol) in toluene (30 ml) was heated at 50–60° C. under nitrogen for 5 hours and allowed to cool overnight. The precipitated solid was removed by filtration and the filtrate concentrated in vacuo to give the product as a white gummy solid (11.50 g, 89%).

9(b) Formation of CIH-THAM-BIH-Dendrimer

A solution of BIH prepared in Example 9a (2 g, 6.54 mmol) and trishydroxyaminomethane (1.58 g, 13 mmol) in THF (40 ml) was stirred at room temperature for 6 hours. The reaction mixture was filtered. CIH (9.33 g, 39 mmol) and potassium hydroxide (0.2 g, 3.6 mmol) were added to the filtrate and heated at 60° C. for 6 hours and cooled. The reaction mixture was concentrated in vacuo. The residue was dissolved in dichloromethane, washed with water, dried ($MgSO_4$), filtered and concentrated in vacuo to give the product as a colourless gum.

EXAMPLE 10

10(a)Triscarbonylimidazolide of Triisopropanolamine (TIPA)

A solution of triisopropanolamine (5.00 g, 26.1 mmol) in toluene (15 ml) was added dropwise, over 1 hr, to a stirred suspension of 1,1'-carbonyldiimidazole 12.71 g, 78.4 mmol) in toluene (50 ml) at room temperature. During addition, the suspension slowly dissolved leaving a clear solution. The solution was allowed to stir for a further 5 hours at 60° C. before the solvent was removed in vacuo. The residue was dissolved in dichloromethane, washed with water, dried ($MgSO_4$), filtered and concentrated in vacuo to give the product as a yellow viscous liquid (11.50 g, 93%)

10(b) Formation of PP-HEIPA-TIPA-Dendrimer

A solution of TIPA prepared in example 10a (2 g, 4.23 mmol), 2-hydroxyethyldiisopropanolamine (HEIPA)(2.25 g, 12.6 mmol) and potassium hydroxide (0.1 g, 1.79 mmol) in THF (50 ml) was heated at 60° C. for 6 hours and cooled. 1,1'-Carbonyl diimidazole (4.11 g, 25.4 mmol) and potassium hydroxide (0.1 g, 1.79 mmol) were added to the reaction mixture and heated at 60° C. for 6 hours. 2-Propyl-1-pentanol (3.30 g, 25.4 mmol) and potassium hydroxide (0.1 g, 1.79 mmol) were added to the reaction mixture and heated to 60° C. for 6 hours and cooled and concentrated. The residue was dissolved in dichloromethane, washed with water, dried ($MgSO_4$), filtered and concentrated in vacuo to give the product as a colourless gum.

EXAMPLE 11

Formation of a Polyurethane Dendrimer

Tris(2-aminoethyl)amine (1.00 g, 6.84 mmol) and CIH prepared in Example 1(a) (4.89 g, 20.5 mmol) in toluene (50 ml) were stirred at room temperature for 5 hours and allowed to stand for 3 days. The crystalline solid that formed was removed by filtration and the filtrate concentrated in vacuo. The residual viscous liquid was dissolved in dichloromethane, washed with water, dried (MgSO$_4$), filtered and concentrated in vacuo to give the product as a thick waxy solid (3.89 g, 87%).

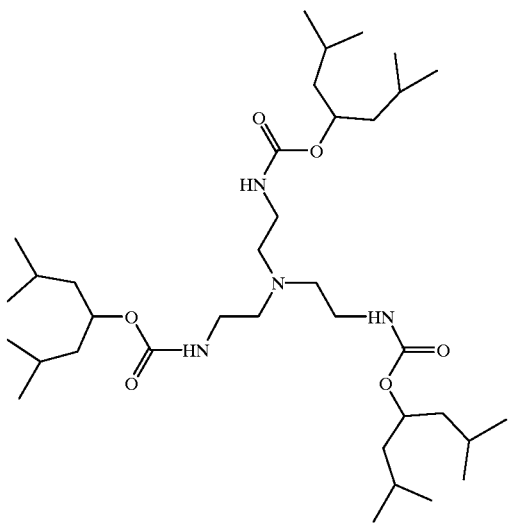

EXAMPLE 12

Dendrimer Formation by Convergent Growth—CIH-TEA

A solution of 2,6-dimethyl-4-heptanol (22.40 g, 5.28 mmol), CDI (25.17 g, 155.23 mmol) and KOH (0.7 g, 12 mmol) in toluene (150 ml) was heated at 50–60° C. under nitrogen for 4 hours. A solution of triethanolamine (7.72 g, 51.74 mmol) in toluene (20 ml) was added slowly to the reaction mixture and heating was continued for a further 4 hours. The reaction mixture was allowed to cool overnight. The crystallised solid was removed by filtration and the filtrate concentrated in vacuo. The residue was dissolved in dichloromethane, washed with water, dried (MgSO$_4$), filtered and concentrated in vacuo to give the product (CIH-TEA) as a clear viscous liquid (33.50 g, 98%).

EXAMPLE 13

Dendrimer Formation by Convergent Growth Multiple Addition Method—CIH-HEAP-TEA

A solution of 2,6-dimethyl-4-heptanol (22.40 g, 155.28 mmol), CDI (25.17 g, 155.23 mmol) and KOH (0.7 g, 12 mmol) in toluene (150 ml) was heated at 50–60° C. under nitrogen for 4 hours. A solution of HEAP (12.67 g, 76.80 mmol) in toluene (20 ml) was added slowly to the reaction mixture and heating was continued for a further 4 hours. The reaction was allowed to cool overnight. The crystallised solid was removed by filtration and the filtrate was returned directly to the reaction vessel. CDI (12.59 g, 77.62 mmol) and KOH (0.2 g, 3.6 mmol) were added to the solution and the reaction mixture was heated to 50–60° C. for 4 hours. The reaction mixture was allowed to cool overnight. The crystallised solid was removed by filtration and the filtrate was returned directly to the reaction vessel. The mixture was heated to 50–60° C. and KOH (0.1 g, 1.8 mmol) was added. A solution of triethanolamine (3.86 g, 25.87 mmol) in toluene (20 ml) was added slowly to the reaction mixture and heating was continued or a further 4 hours. The reaction was allowed to cool overnight. The crystallised solid was removed by filtration and the filtrate concentrated in vacuo. The residue was dissolved in dichloromethane, washed with water, dried (MgSO$_4$), filtered and concentrated in vacuo to give the product (CIH-HEAP-TEA) as a clear viscous liquid (43.11 g, 96%).

EXAMPLE 14

Dendrimer Formation by Convergent Growth—CIH-HEAP-HEAP-TEA Synthesis

A solution of CIH-HEAP-HEAP-OH (1.00 g, 0.82 mmol) (prepared in example 2b), 1,1'-carbonyl diimidazole 3.20 g, 1.23 mmol) and potassium hydroxide (0.10 g, 1.79 mmol) in toluene (20 ml) was heated at 60° C. for 5 hours then cooled. The reaction mixture was filtered. Triethanolamine (41 mg, 0.28 mmol) and potassium hydroxide (0.10 g, 1.79 mmol) in tertiary butanol (5 ml) were added to the filtrate and heated at 60° C. for 5 hours then cooled. The precipitated solid was removed by filtration. The filtrate was washed with water, dried (MgSO$_4$), filtered and concentrated in vacuo to give the polycarbonate dendrimer as a colourless gum (0.83 g, 78%).

EXAMPLE 12
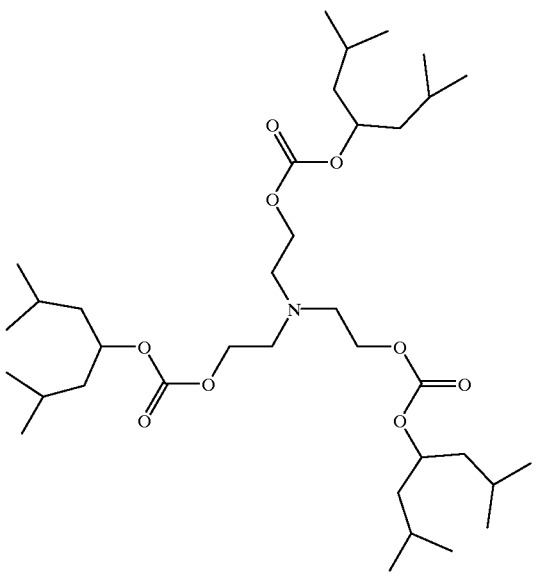
EXAMPLE 13
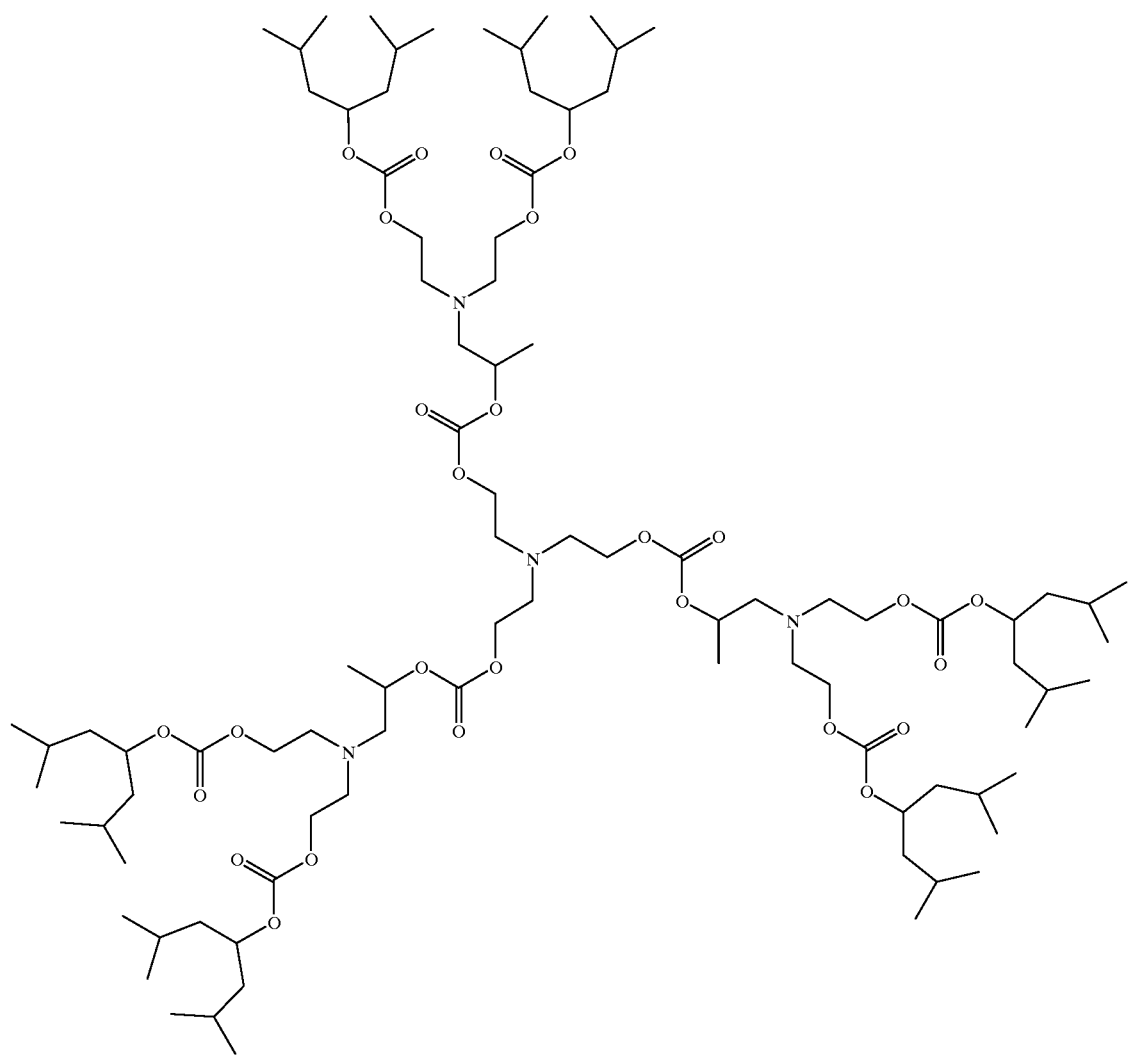

-continued
EXAMPLE 14

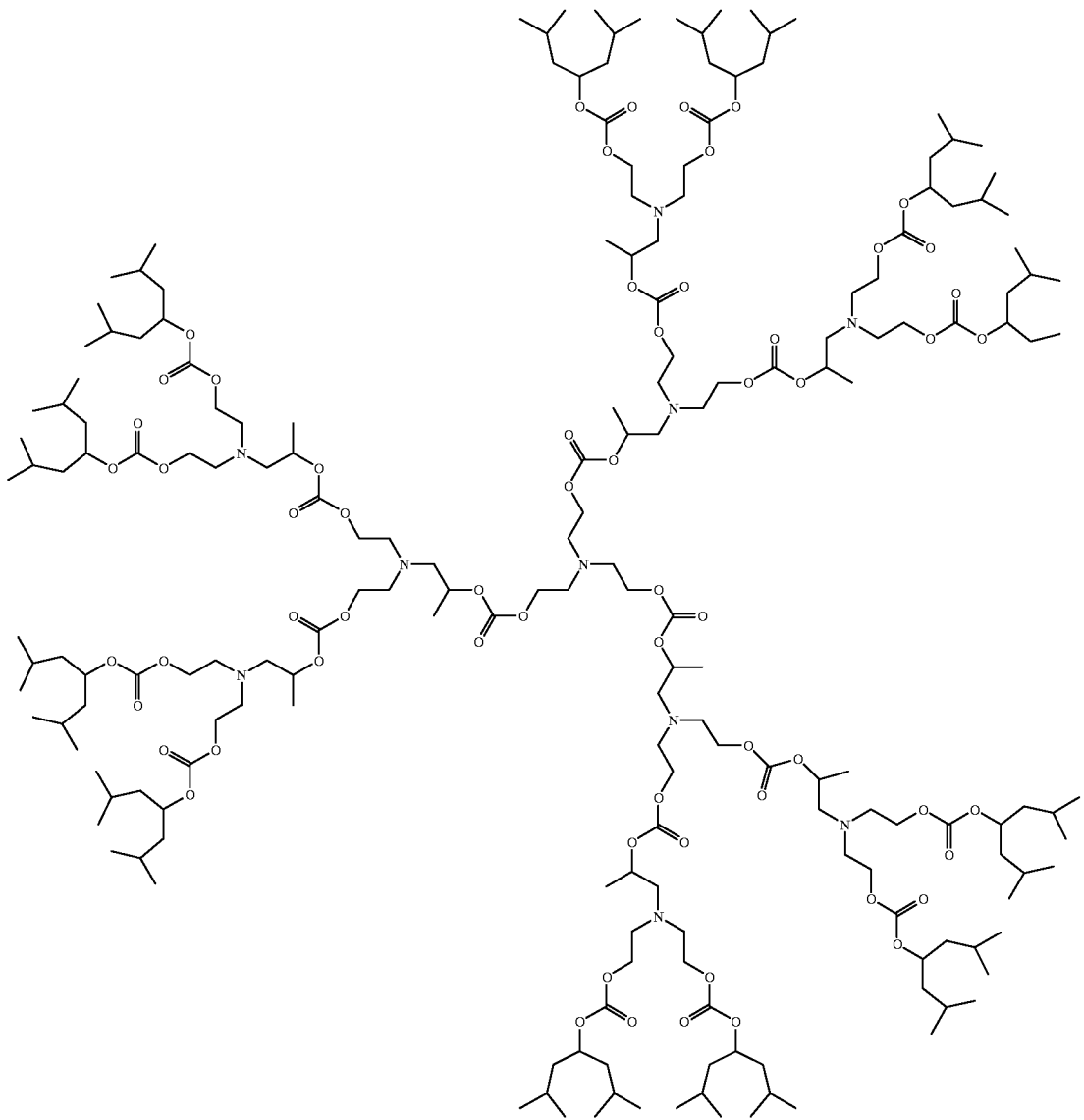

EXAMPLE 15

Dendrimer Formation by Convergent Growth—CIB-TEA Synthesis

A solution of tertiary butanol (28.00 g, 0.38 mol) and 1,1'-carbonyldiimidazole (60.00 g, 0.37 mol) in toluene (150 ml) with potassium hydroxide (1.78 g, 32 mmol) was heated at 60° C. for 5 hours and cooled. The mixture was reheated to 60° C. when a solution of triethanolamine (TEA) (17.68 g, 0.12 mol) in tertiary butanol (20 ml) was added over 30 minutes and the mixture heated at 60° C. for 6 hours and cooled. The precipitated solid was removed by filtration, and the filtrate was washed with water, dried ($MgSO_4$), filtered and concentrated in vacuo to give the dendrimer as a colourless gum (51.53 g, 97%).

EXAMPLE 16

16(a) formation of CIB-HEAP-OH

A solution of tertiary butanol (20.22 g, 0.28 mol) and 1,1'-carbonyldiimidazole (43.78 g, 0.28 mol) in toluene (150 ml) with potassium hydroxide (1.30 g, 23 mmol) was heated at 60° C. for 5 hours and cooled. The reaction mixture was reheated to 60° C. when a solution of HEAP (21.20 g, 0.13 mol) in toluene (60 ml) was added dropwise over 30 minutes and the mixture heated at 60° C. for 5 hours then cooled. The precipitated solid was removed by filtration, the filtrate was washed with water, tried ($MgSO_4$), filtered and concentrated in vacuo to give the product as a colourless gum (46.73 g, 99%).

16(b) Dendrimer Formation by Convergent Growth—CIB-HEAP-TEA Synthesis

A solution of CIB-HEAP-OH (9.53 g, 26 mmol) and 1,1'-carbonyl diimidazole (4.25 g, 26 mmol) in toluene (100 ml) with potassium hydroxide (0.20 g, 3.6 mmol) was heated at 60° C. for 1.5 hours and cooled. The reaction mixture was filtered. Triethanolamine (1.30 g, 8.75 mmol) in tertiary butanol (5 g) and potassium hydroxide (0.20 g, 3.6 mmol) were added to the filtrate and the reaction mixture heated at 60° C. for 9 hours then cooled. The precipitated solid was removed by filtration, the filtrate was washed with water, dried (MgSO₄), filtered and concentrated in vacuo to give the dendrimer as a colourless gum (9.45 g, 82%).

EXAMPLE 17

Dendrimer Formation by Convergent Growth—CIB-HEAP-HEAP-TEA

A solution of CIB-HEAP-OH prepared in Example 16(a) (9.50 g, 26.0 mmol), CDI (4.25 g, 26.0 mmol) and KOH (0.20 g, 3.6 mmol) in toluene (100 ml) was heated at 50–60° C. for 5 hours. The reaction was allowed to cool overnight. The crystallised solid was removed by filtration and the filtrate was returned directly to the reaction vessel. KOH (0.10 g, 1.8 mmol) was added to the mixture and the reaction mixture was heated to 50–60° C. A solution of HEAP (2.12 g, 13 mmol) in toluene (10 ml) was slowly added and the solution was heated for a further 5 hours. CDI (2.11 g, 13.0 mmol) and KOH (0.1 g, 1.8 mmol) were added and the reaction mixture was heated for 3 hours. The reaction mixture was allowed to cool overnight. The crystallised solid was removed by filtration and the filtrate was returned directly to the reaction vessel. KOH (0.01 g, 1.8 mmol) was added to the solution and the mixture was heated to 50–60° C. A solution of triethanolamine (0.65 g, 4.33 mmol) in tertiary butanol (5 g) was added slowly and the reaction was heated for a further 5 hours. The reaction mixture was allowed to cool overnight. The crystallised solid was removed by filtration and the filtrate concentrated in vacuo. The residue was dissolved in dichloromethane, washed with water, dried (MgSO₄), filtered and concentrated in vacuo to give the product (CIB-HEAP-HEAP-TEA) as a clear viscous liquid (12.03 g, 91%).

EXAMPLE 15

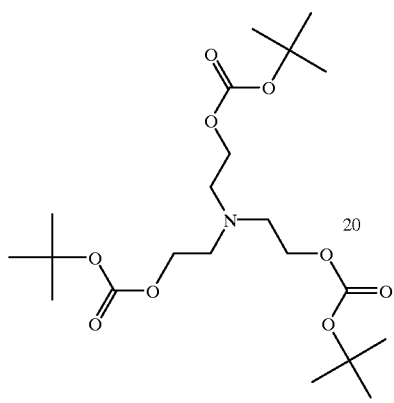

EXAMPLE 16

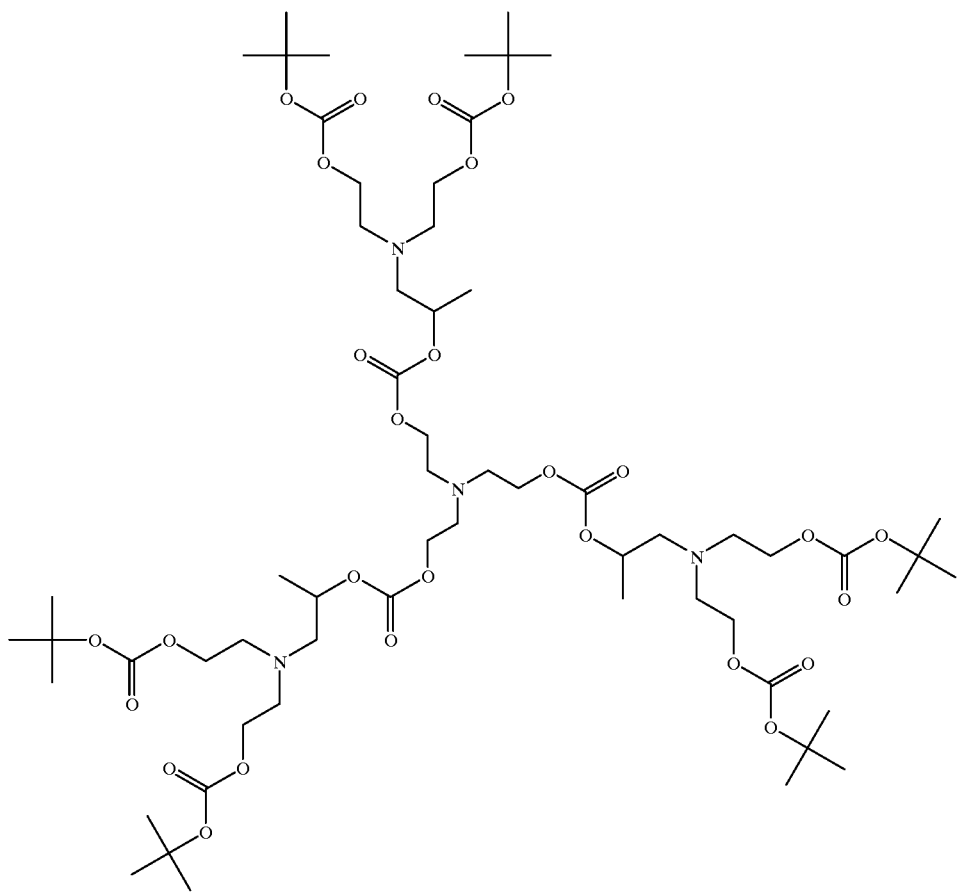

-continued
EXAMPLE 17

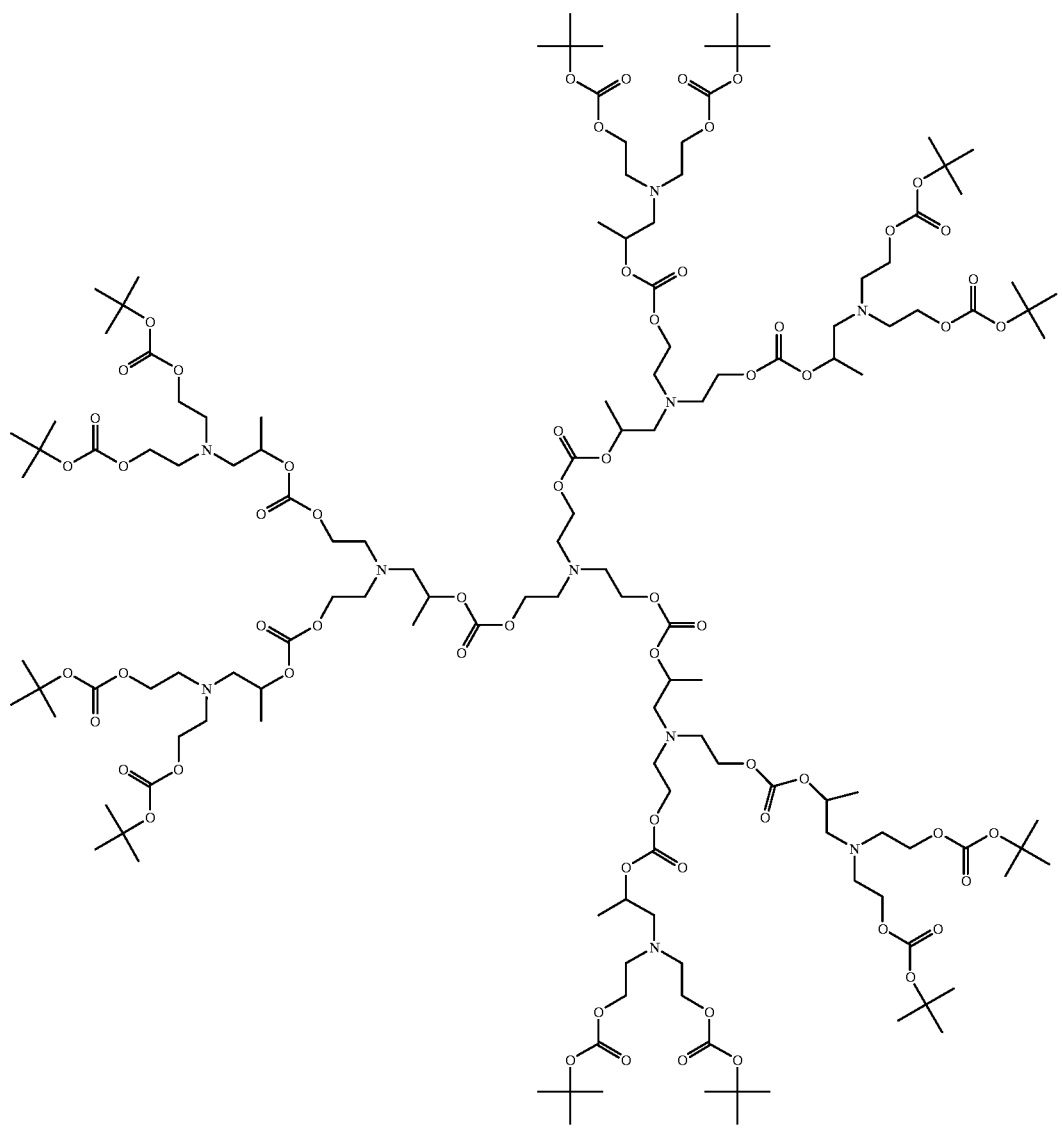

EXAMPLE 18

Formation of CTB-HEAP-Dendrimer

A solution of CIB-HEAP-OH prepared in Example 16(a) (2.00 g, 5.5 mmol), 1,1'-carbonyl diimidazole (1.34 g, 8.27 mmol) and potassium hydroxide (0.20 g, 3.6 mmol) in toluene (20 ml) was heated at 60° C. for 4 hours and cooled. The reaction mixture was filtered. Propanediol (PrD) (0.21 g, 2.76 mmol) and potassium hydroxide (0.10 g, 1.79 mmol) were added to the filtrate and heated at 60° C. for 6 hours and cooled. The reaction mixture was filtered. The filtrate was washed with water, dried ($MgSO_4$), filtered and concentrated in vacuo to give the product as a pale yellow gum (2.31 g, 98%).

EXAMPLE 19

Formation of CIH-HEAP-PrD-Dendrimer

A solution of CIH-HEAP-OH prepared in Example 1 (2.00 g, 3.98 mmol), 1,1'-carbonyl diimidazole (0.97 g, 5.99 mmol) and potassium hydroxide (0.20 g, 3.6 mmol) in toluene (20 ml) was heated at 60° C. for 4 hours and cooled. The reaction mixture was filtered. Propanediol (0.15 g, 1.97 mmol) and potassium hydroxide (0.20 g, 3.6 mmol) were added to the filtrate and heated at 60° C. for 5 hours and cooled. The reaction mixture was filtered. The filtrate was washed with water, dried ($MgSO_4$), filtered and concentrated in vacuo to give the product as a pale yellow gum (2.21 g, 95%).

EXAMPLE 20

20(a) Formation of CTB-HEAP-HEAP-OH

A solution of CIB-HEAP-OH (43.00 g, 0.12 mol) and 1,1'-carbonyl diimidazole (28.79 g, 0.18 mol) in toluene (100 ml) with potassium hydroxide (1.00 g, 18 mmol) was heated at 60° C. for 3 hours and cooled. The reaction mixture was filtered. HEAP (9.56 g, 59 mmol) and potassium hydroxide (1.00 g, 18 mmol) were added to the filtrate and the reaction mixture heated at 60° C. for 5 hours then cooled. The reaction mixture was filtered, the filtrate washed with water, dried (MgSO$_4$), filtered and concentrated in vacuo to give the product as a colourless gum (54.74 g, 99%).

This product CIB-HEAP-HEAP-OH was formed as an intermediate product during the preparation of Example 17, but was not isolated then. In the present preparation CIB-HEAP-HEAP-OH was isolated, although the process of Example 20(b) could alternatively have been carried out using the filtered reaction mixture of Example 20(a) before isolation.

A solution of CIB-HEAP-HEAP-OH (1.00 g, 1.06 mmol), 1,1'-carbonyl diimidazole (0.258 g, 7.59 mmol; and potassium hydroxide (0.10 g, 1.79 mmol) in toluene (20 ml) was heated at 60° C. for 6 hours and cooled. The reaction mixture was filtered. Propanediol (0.04 g, 0.53 mmol) and potassium hydroxide (0.10 g, 1.79 mmol) were added to the filtrate and heated at 60° C. for 6 hours and cooled. The reaction mixture was filtered. The filtrate was washed with water, dried (MgSO$_4$), filtered and concentrated in vacuo to give the product as a colourless gum (1.02 g, 95%).

EXAMPLE 21

Formation of CIH-HEAP-HEAP-PrD-Dendrimer

A solution of CIH-REAP-HEAP-OH prepared in Example 2b) (2.00 g, 1.6 mmol), 1,1'-carbonyl diimidazole (0.40 g, 2.5 mmol) and potassium hydroxide (0.20 g, 3.6 mmol) in toluene (20 ml) was heated at 60° C. for 5 hours and cooled. The reaction mixture was filtered. Propanediol (0.062 g, 0.80 mmol) and potassium hydroxide (0.20 g, 3.6 mmol) were added to the filtrate and heated at 60° C. for 5 hours and cooled. The reaction mixture was filtered. The filtrate was washed with water, dried (MgSO$_4$), filtered and concentrated in vacuo to give the product as a colourless gum (2.04 g, 97%)

EXAMPLE 22

Formation of CIB-HEAP-TAEA-Dendrimer

A solution of CIB-HEAP-OH prepared in Example 16(a) (3.00 g, 8.3 mmol), 1,1'-carbonyl diimidazole (2.01 g, 12.4 mmol) and potassium hydroxide (0.20 g, 3.6 mmol) in toluene (20 ml) was heated at 60° C. for 1, hour then cooled. The reaction mixture was filtered. Tris(2-aminoethyl) amine (TAEA) (0.40 g, 2.74 mmol) was added to the filtrate and stirred at room temperature for 6 hours. The reaction mixture was filtered, the filtrate was washed with water, dried (MgSO$_4$), filtered and concentrated in vacuo to give the product as a pale yellow gum (3.34 g, 93%).

EXAMPLE 23

Formation of CIH-HEAP-TAEA-Dendrimer

A solution of CIH-HEAP-OH prepared in Example 1(b) (3.000 g, 5.96 mmol), 1,1'-carbonyl diimidazole (1.45 g, 8.95 mmol) and potassium hydroxide (0.20 g, 3.6 mmol) in toluene (20 ml) was heated at 60° C. for 2 hours then cooled. The reaction mixture was filtered. Tris(2-aminoethyl) amine (0.29 g, 1.99 mmol) was added to the filtrate and stirred at room temperature for 6 hours and then at 60° C. for 5 hours then cooled. The reaction mixture was filtered, the filtrate was washed with water, dried (MgSO$_4$), filtered and concentrated in vacuo to give the product as a pale yellow gum (3.31 g, 96%).

EXAMPLE 24

Formation of CIB-HEAP-HEAP-TAEA-Dendrimer

A solution of CIB-HEAP-HEAP-OH prepared in Example 20(a) (4.00 g, 4.25 mmol), 1,1'-carbonyl diimidazole (1.04 g, 6.42 mmol) and potassium hydroxide (0.40 g, 7.14 mmol) in toluene (40 ml) was heated at 60° C. for 6 hours then cooled. The reaction mixture was filtered. Tris (2-aminoethyl) amine (0.207 g, 1.42 mmol) was added to the filtrate and stirred at 60° C. for 6 hours, then cooled. The reaction mixture was filtered, the filtrate was washed with water, dried (MgSO$_4$), filtered and concentrated in vacuo to give the product as a pale yellow gum (4.16 g, 96%).

EXAMPLE 25

25(a) Formation of BEHA-SAn-CO$_2$H (N,N-bis(2-ethylhexyl) monoamide of succinic acid)

A solution of bis (2-ethylhexyl)amine (BEHA) (2.00 g, 8.3 mmol) and succinic anhydride (SAn) (0.83 g, 8.3 mmol) in toluene (20 ml) was stirred at room temperature for 6 hours. The reaction mixture was concentrated in vacuo to give the product as a colourless gum (2.83 g, 100%).

25(b) Formation of BEHA-SAn-TAEA-Dendrimer

A solution of BEHA-SAn-CO$_2$H (1.00 g, 2.93 mmol) and 1,1'-carbonyl diimidazole (0.48 g, 2.96 mmol) in toluene (20 ml) and THF (20 ml) was stirred at room temperature for 2 hours and then at 60° C. for 1 hour. Tris(2-aminoethyl)amine (0.14 g, 0.96 mmol) was added and the solution stirred at 60° C. for 3 hours, then cooled. The reaction mixture was filtered and concentrated in vacuo. The residue was dissolved in toluene, washed with water, dried (MgSO$_4$), filtered and concentrated in vacuo to give the product as a pale yellow gum (1.05 g, 96%)

EXAMPLE 26

Formation or CIH-DTA-SAn-TAEA-Dendrimer

A solution of CIH (6.00 g, 25 mmol) and diethylene triamine (DTA) (1.30 g, 12.6 mmol) in toluene (50 ml) was heated at 60° C. for 9 hours and cooled. The reaction mixture was washed with water, dried (MgSO$_4$), filtered and concentrated in vacuo to give CIH-DTA-NH as a colourless gum (5.45 g, 97%). A solution of CIH-DTA-NH (4.10 g, 9.2 mmol) and succinic anhydride (0.92 g, 9.2 mmol) in toluene (40 ml) was stirred at room temperature for 24 hours. 1,1'-Carbonyl diimidazole (1.52 g, 9.4 mmol) in THF (20 ml) was added and stirred at room temperature for 24 hours. Tris (2-aminoethyl) amine was added and stirred at 60° C. for 6 hours cooled and concentrated in vacuo. The mixture was dissolved in toluene, washed with water, dried (MgSO$_4$), filtered and concentrated in vacuo to give the product as a yellow glassy solid (4.99 g, 90%).

EXAMPLE 26

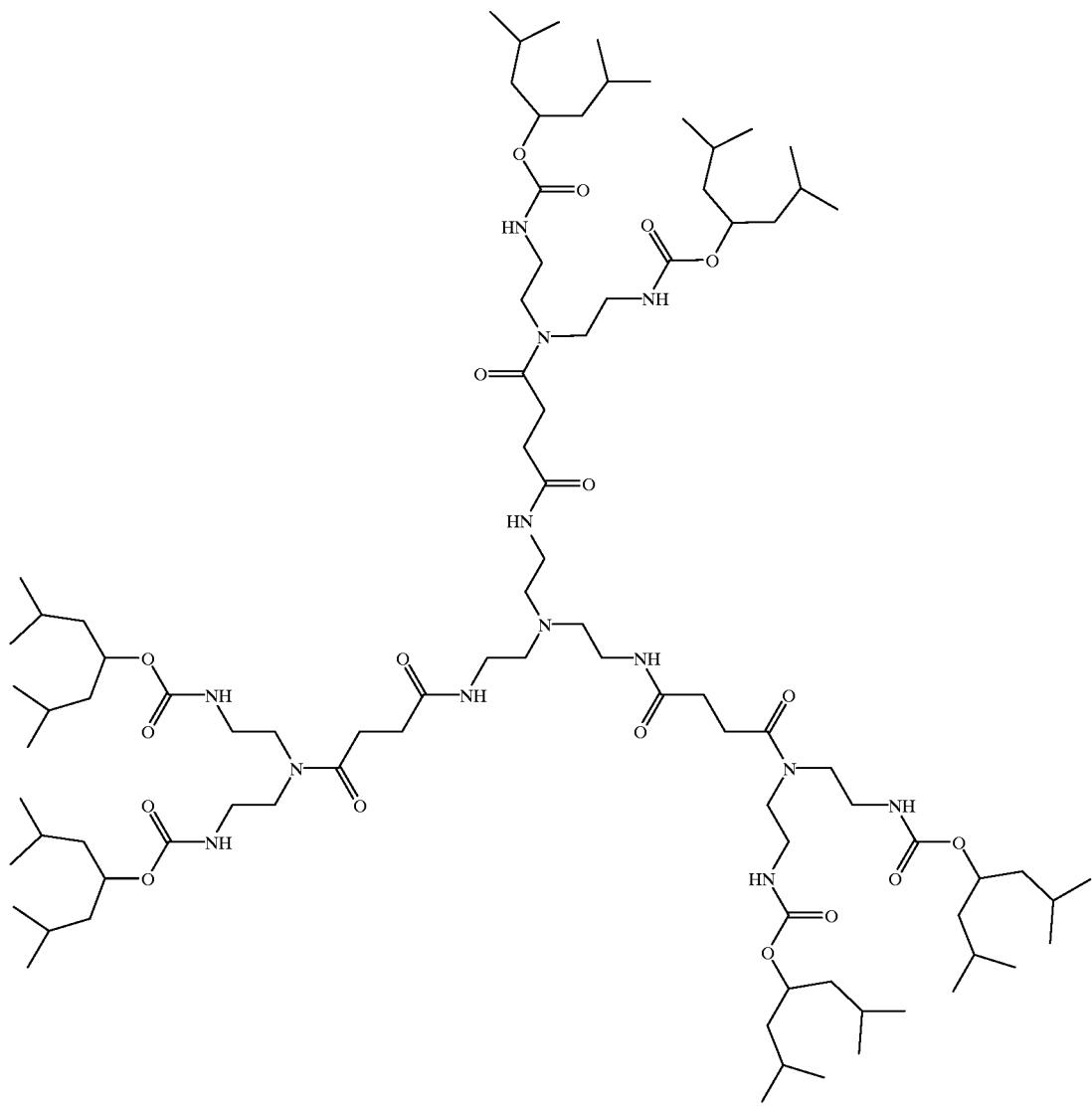

EXAMPLE 27

Formation of CIH-HEAP-DTA-SAn-TAEA-Dendrimer

A solution of CIH-HEAP-OH (5 g, 9.9 mmol), 1,1'-carbonyl diimidazole (2.42 g, 15 mmol) and potassium hydroxide (0.40 g, 7.14 mmol) in toluene (40 ml) was heated at 60° C. for 6 hours and cooled. The reaction mixture was filtered. Diethylene triamine (0.51 g, 4.95 mmol) was added to the filtrate and the reaction mixture heated at 60° C. for 6 hours and cooled. The reaction mixture was filtered, the filtrate was washed with water, dried (MgSO$_4$), filtered and concentrated in vacuo to give CIH-HEAP-DTA-NH as a colorless gum (5.63 g, 98i). A solution of CIH-HEAP-DTA-NH (5.50 g, 4.7 mmol) and succinic anhydride (0.47 g, 4.7 mmol) in toluene (40 ml) was stirred at room temperature or 6 hours. 1,1'-Carbonyl diimidazole (0.77 g, 4.75 mmol) in toluene (40 ml) was stirred at room temperature for 16 hours. Tris (2-aminoethyl) amine (0.23 g, 1.58 mmol, was added and stirred at 60° C. for 6 hours and cooled then concentrated in vacuo. The reaction mixture was dissolved in toluene, washed with water, dried (MgSO$_4$), filtered and concentrated in vacuo to give the dendrimer as a yellow gum (5.99 g, 97%).

EXAMPLE 27

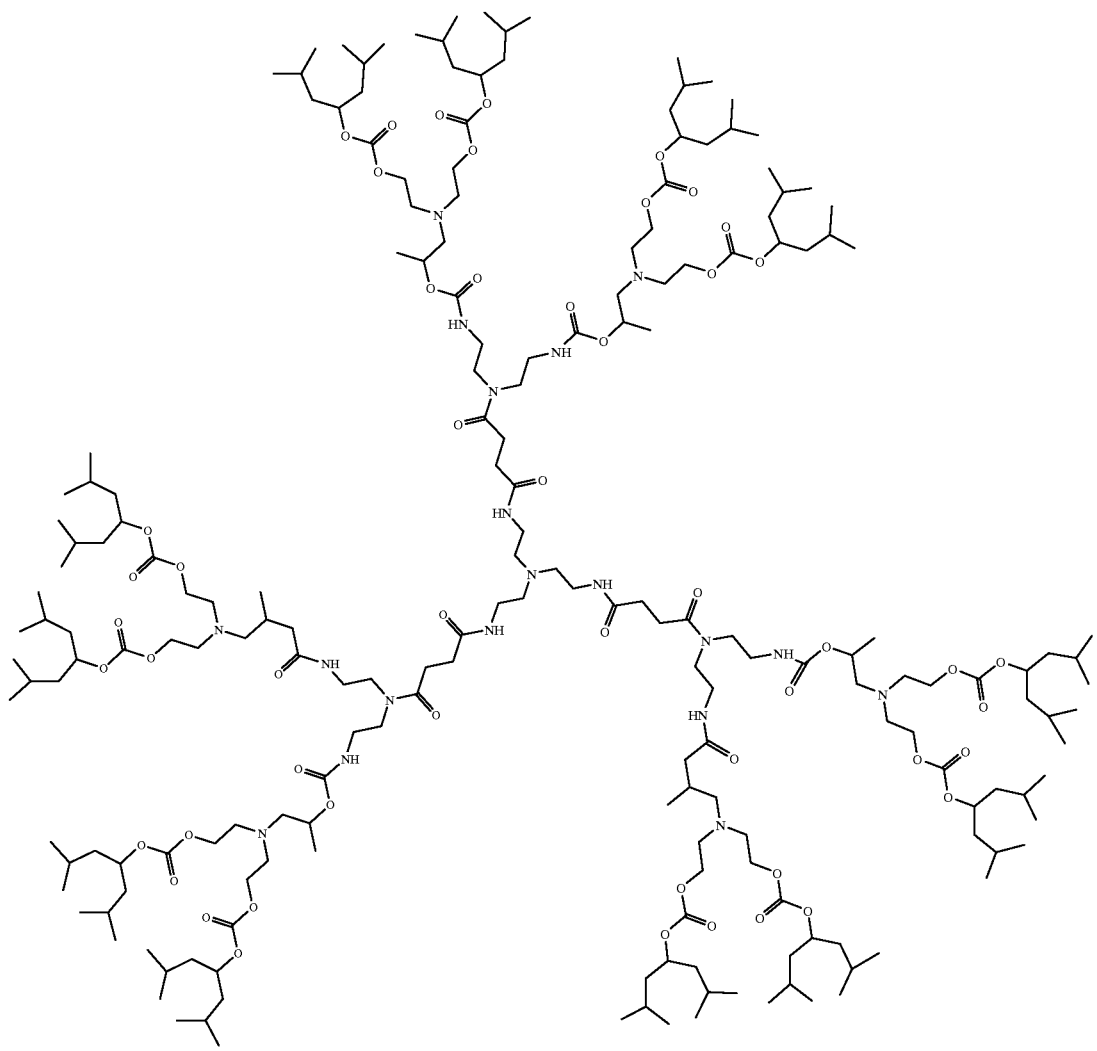

EXAMPLE 28

Formation of CIB-HEAP-DTA-SAn-TAEA-Dendrimer

A solution of CIB-HEAP-OH (5 g, 13.8 mmol), 1,1'-carbonyl diimidazole (3.35 g, 20.7 mmol) and potassium hydroxide (0.40 g, 7.14 mmol) in toluene (40 ml) was heated at 60° C. for 4 hours and cooled. The reaction mixture was filtered. Diethylene triamine (0.709 g, 6.9 mmol) was added to the filtrate and the reaction mixture heated at 60° C. for 6 hours and cooled. The reaction mixture was filtered, the filtrate was washed with water, dried ($MgSO_4$), filtered and concentrated in vacuo to give CIB-HEAP-DTA-NH as a yellow gum (5.94 g, 98%). A solution of CIB-HEAP-DTA-NH (4.34 g, 4.93 mmol) and succinic anhydride (0.49 g, 4.9 mmol) in toluene (40 ml) was stirred at room temperature for 24 hours then concentrated in vacuo to give CIB-HEAP-DTA-SAn-$CO_2$H as a yellow gum (4.72 g, 98%). A solution of CIB-HEAP-DTA-SAn-$CO_2$H (4.14 g, 4.2 mmol) and 1,1'-carbonyl diimidazole (0.68 g, 4.2 mmol) in toluene (20 ml) and THF (20 ml) was stirred at room temperature for 24 hours. Tris (2-aminoethyl) amine (0.21 g, 1.4 mmol) was added and stirred at 60° C. for 6 hours and cooled then concentrated in vacuo. The reaction mixture was dissolved in toluene, washed with water, dried ($MgSO_4$), filtered and concentrated in vacuo to give the dendrimer as a yellow glassy solid (4.15 g, 95%).

EXAMPLE 28

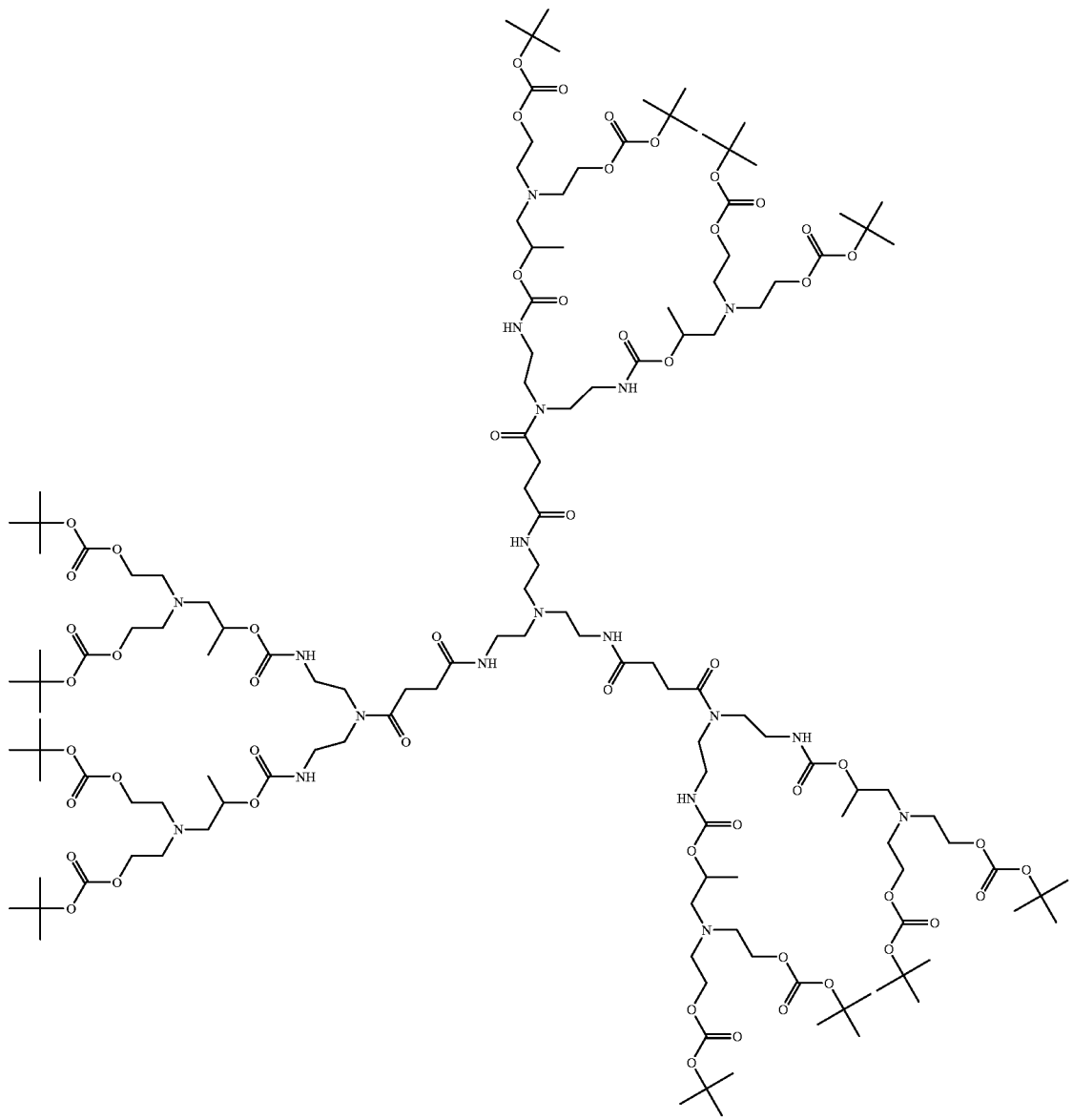

EXAMPLE 29

Formation of CIB-DTA-SAn-TAEA-Dendrimer

A solution of DTA (1.53 g, 14.86 mmol) in toluene (10 ml) was added dropwise to a solution of CIB (5 g, 29.73 mmol) in toluene (50 ml). The resulting solution was heated to 60° C. for 5 hours and left to cool overnight. The crystallised solid was removed by filtration and the filtrate concentrated in vacuo. The residue was dissolved in dichloromethane, washed with water, dried ($MgSO_4$), filtered and concentrated (3.65 g, 81%). Some of the product was retained for analysis. The product CIB-DTA-NH (3.56 g, 11.73 mmol) and succinic anhydride (1.17 g, 11.70 mmol) were stirred at room temperature in toluene (50 ml). The mixture cleared after approximately 1 hour. The solution was left to stir overnight. CDI (1.00 g, 11.70 mmol) was added at room temperature with stirring and $CO_2$ liberation. When the effervescence had ceased, a solution of TAEA (0.57 g, 3.90 mmol) in toluene (5 ml) was added and the reaction was left to stir overnight at room temperature. The reaction was concentrated in vacuo. The residue was dissolved in dichloromethane, washed with water, dried ($MgSO_4$), filtered and concentrated in vacuo to give the solid product (CIB-DTA-SAn-TAEA-Dend) (4.28 g, 81%).

EXAMPLE 29

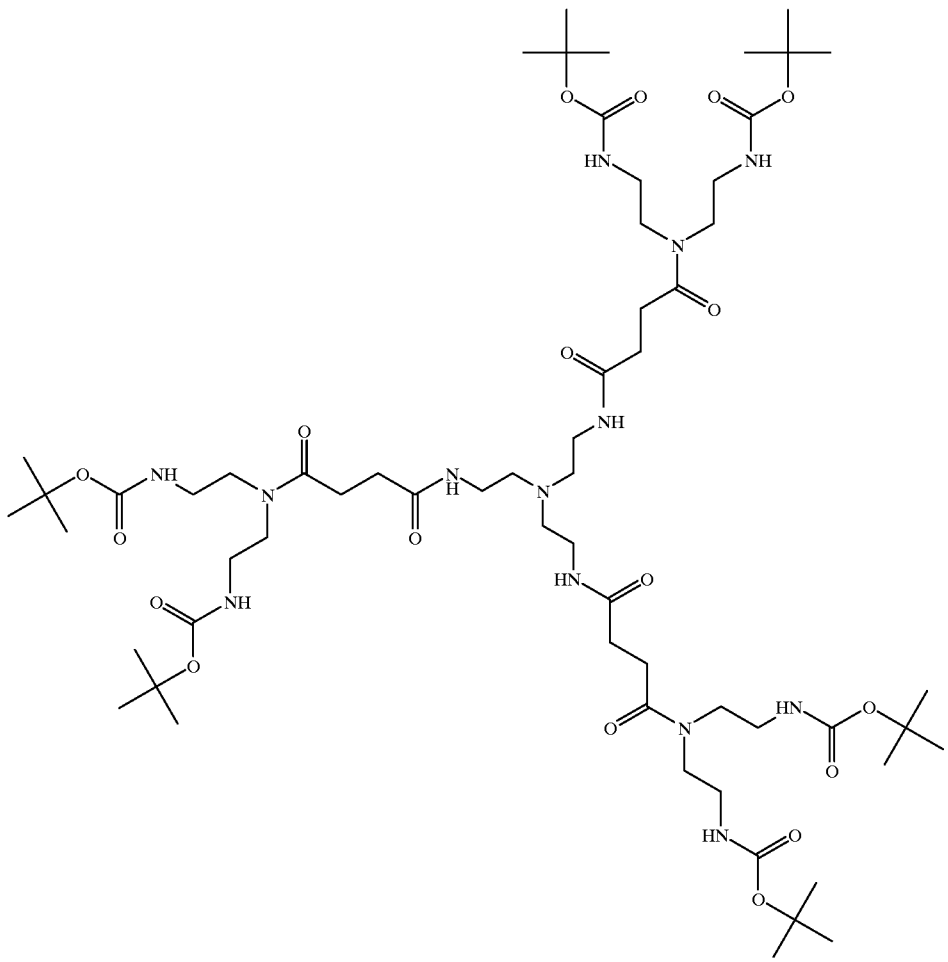

EXAMPLE 30

Formation of CIB-DTA-SAn-DTA-NH Dendritic Wedge

A solution of t-butanol (5.00 g, 67.46 mmol) in toluene (100 ml), CDI (10.00 g, 61.67 mmol) and KOH (0.2 g, 3.6 mmol) was stirred at 50–60° C. for 4 hours. Without work-up, a solution of DTA (3.06 g, 29.66 mmol) in toluene (10 ml) was added and the reaction was allowed to stir while cooling to room temperature. The solution was left to stand overnight. The crystallised solid was removed by filtration and the filtrate concentrated in vacuo. The residue was dissolved in dichloromethane, washed with water, dried (MgSO$_4$), filtered and concentrated (8.04 g, 91%). The product (4.42 g, 14.57 mmol) and succinic anhydride (1.46 g, 14.57 mmol) were stirred at room temperature in toluene for 6 hours. CDI (2.36, 14.57 mmol) was added. The reaction mixture was left to stir at room temperature until effervescence had ceased. A solution of DTA (0.75 g, 7.29 mmol) in toluene (20 ml) was slowly added and a thick precipitate formed. THF (20 ml) was added and the solution was heated to 50–60° C. For 6 hours. The solution was left to cool overnight. The reaction was concentrated in vacuo. The residue was dissolved in dichloromethane, washed with water, dried (MgSO$_4$), filtered and concentrated in vacuo to give the solid product (CIB-DTA-SAn-DTA-NH) (5.01 g, 76%). This is a dendritic wedge having secondary amine functionality.

EXAMPLE 30

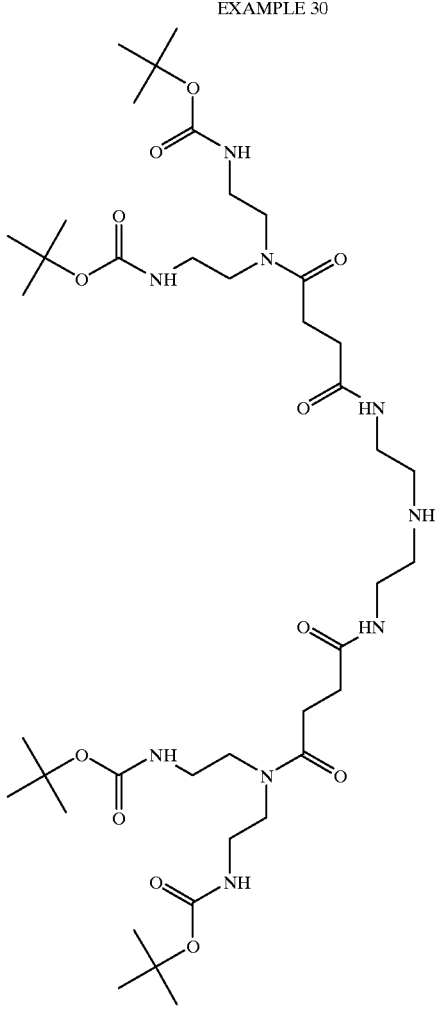

EXAMPLE 31

Formation of BEHA-SAn-DTA-SAn-TAEA-Dend

A solution of BEHA (6.000 g, 24.85 mmol) and succinic anhydride (2.48 g, 24.85 mmol) in toluene (100 ml) was stirred at room temperature for 5 hours. CDT (4.03 g, 24.85 mmol) was added. The reaction was left to stir at room temperature until effervescence had ceased. A solution of DTA (1.28 g, 12.42 mmol) in toluene (10 ml) was slowly added and the solution was left to stir overnight. The reaction mixture was concentrated in vacuo and the residue was dissolved in dichloromethane, washed with water, dried (MgSO$_4$), filtered and concentrated in vacuo to give the product BEHA-SAn-DTA-NH (7.93 g, 85%). The purified product (5.13 g, 6.84 mmol) and succinic anhydride (0.68 g, 6.84 mmol) were stirred in toluene (100 ml) at room temperature for 5 hours. CDI (1.11 g, 6.84 mmol) was added. The reaction mixture was left to stir at room temperature until effervescence had ceased. A solution of TAEA (0.33 g, 2.23 mmol) in toluene (10 ml) was slowly added and the solution was left to stir overnight. The reaction mixture was concentrated in vacuo and the residue was dissolved in dichloromethane, washed with water, dried (MgSO$_4$), filter and concentrated in vacuo to give the product BEHA-SAn-DTA-SAn-TAEA-Dend (5.21 g, 85%).

EXAMPLE 31

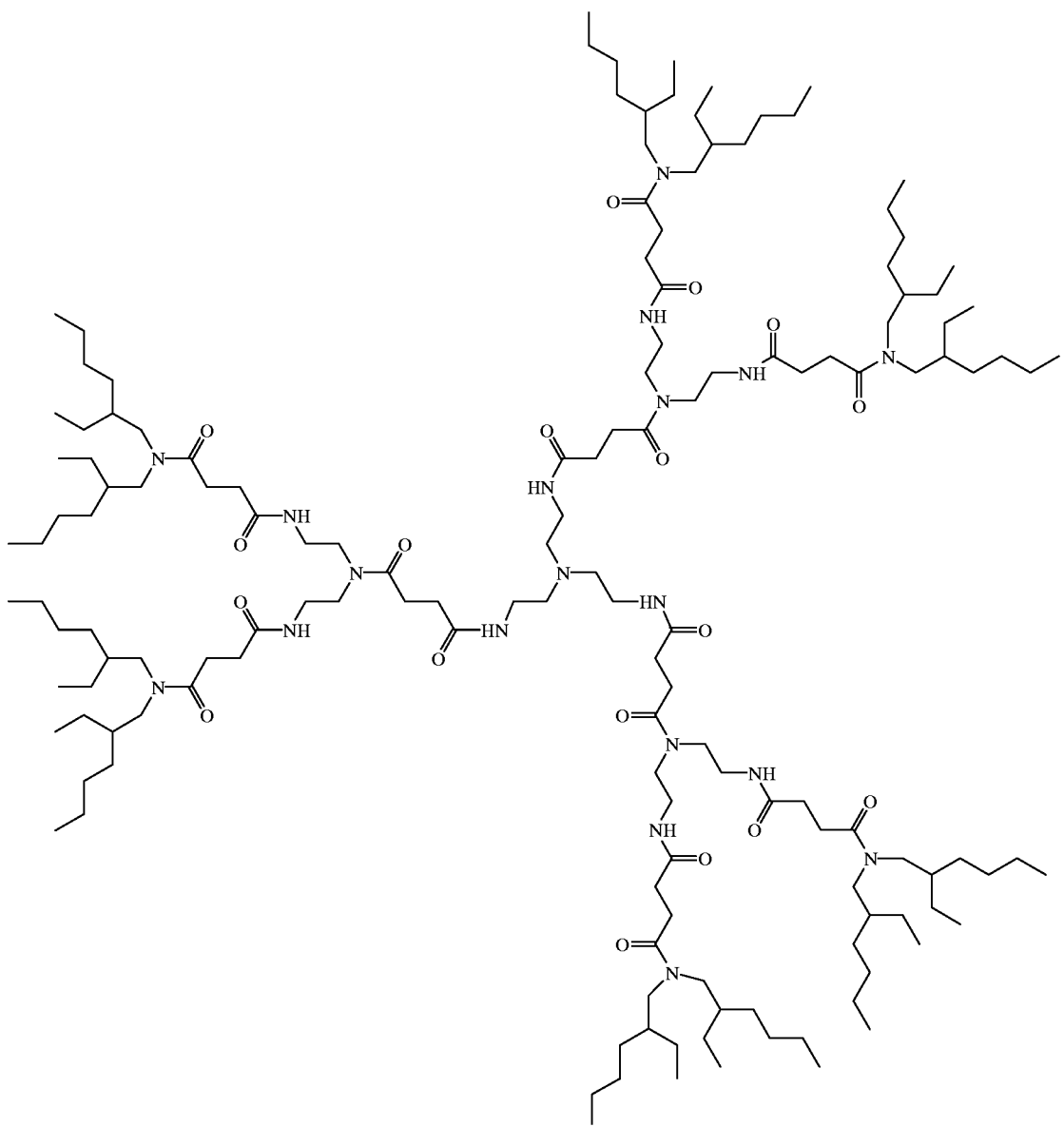

The glass transition temperatures of the dendrimers of the invention show the effects of changing internal branch type, chemical link, surface chemistry, generation and core structure. The accurate control of the Tg of materials for use in coatings, sealants or adhesives is a real possibility using this chemistry.

The effect of increasing generation on glass transition temperature may be explained by the packing or the surface groups restricting the motion of the internal branches. Increases in dendrimer molecular weight are obtained by increasing generation. As the generation increases the diameter of the molecule increases by a factor determined by the size of the branching group. The number of surface groups increases rapidly and must pack increasingly closer together, occupying the available surface area that is formed according to the increasing diameter. The increased packing a the dendrimer surface results in decreased mobility within the molecule and strain being imposed on the internal arms. The Tg may therefore increase with increasing generation. The polycarbonate dendrimers containing dimethyl-heptyl surface groups show no noticeable increase between the second and third generations (CIH-TEA and CIH-HEAP-TEA prepared in Examples 12 and 13 respectively) both have a Tg of −62° C. The fourth generation CIH-HEAP-HEAP-TEA prepared in Example 14 shows a slight increase in Tg to −56° C.

The increase in Tg is highly dependent upon the internal structure of the dendrimer. Polyamide dendrimers show a much greater increase. Structures containing bis(ethyl hexyl) surface show a 52° C. increase in Tg on increasing generation from 2 to 3, that is from BEHA-SAn-TAEA prepared in Example 25, which has a Tg of −97° C. to BEHA-SAn-DTA-SAn-TAEA prepared in Example 31, which has a Tg of −45° C. This may be due to the size of the surface group but also due to the hydrogen bonding within the molecule.

By changing the nature and size of surface groups at the same generation, differences in Tg also occur. The polycarbonate dendrimers with dimethyl-heptyl and t-butyl surfaces CIH-HEAP-TEA (Example 13) and CIB-HEAP-TEA (Example 16) have Tgs of −62°° C. and −26° C. respectively demonstrating the effect of increasing surface group size.

The effect of changing surface can also be seen in the polyamide dendrimers. BEHA-SAn-DTA-SAn-TAEA prepared in Example 31 is a third generation polyamide dendrimer with bis(ethyl hexyl) surface and is a viscous liquid having a Tg=−45° C. CIB-DTA-SAn-TAEA is an analagous dendrimer where the surface is changed to a t-butyl urethane group and is a solid with a Tg of 16° C. and a melting point of over 100° C.

Carbonyl diimidazole may be used to form a number of chemical links chosen from carbonate, urethane, urea, amide or ester. If the chemical link is changed within the same structure, large effects can be seen on the Tg of a small dendrimer. The polycarbonate CIH-TEA of Example 12 was a free-flowing liquid of Tg −62° C. but the polyurethane CIH-TAEA of Example 11 was a solid material with a melting point of 86° C.

The effect of changing the internal chemistry of the core molecule can also be seen at higher generations but the effect is not as noticeable. The third generation polycarbonate dendrimer CIH-HEAP-TEA prepared in Example 13 has a Tg of −62° C. If the core is changed so that it is linked via three urethane links (CIH-HEAP-TAEA prepared in Example 23), the Tg increases by 6° C. The surface effect is more important than internal chemical changes around the core, but this is another route to affect the physical properties of dendrimers without changing the surface characteristics.

The nature of the core molecule ultimately determines the success of a convergent dendrimer synthesis. If the dendritic wedges cannot pack sufficiently well around the core it wall be impossible to couple all of them in the final step. The core also plays a large role in determining the physical properties of the final molecules. The larger the core, the lower the constraints imposed on the branches and the higher the mobility. When the core was changed for a second generation polycarbonate dendrimer from triethanolamine to TMP, the Tg increased by 18° C. CIH-TEA of Example 12 had a Tg of −62° C. whereas CIH-TMP of Example 4 had a Tg of −44° C.

The glass transition temperature of dendritic polymers is an indication of the internal mobility of the molecule. This is dependent on the structure of the branches as well as the chemical links and surface groups. Polycarbonate-polyarethane copolymer dendrimers have been synthesised that have identical cores, chemical links and surface groups but different internal branches derived from HEAP and TMP. TMP is a much smaller and more crowded branch molecule with five atoms between carbonate and urethane carbonyls. Also, it has an ethyl substituent at the branch point which reduces the available "free volume" and restricts motion. HEAP has seven atoms between carbonyls and no extra substitution at the branch point. CIH-HEAP-TAEA of Example 23 had a Tg of −56° C. whereas CIH-TMP-TAEA of Example 5(b) had a Tg of −30° C.

EXAMPLE 32

Formation of BA-DHBA-DHBA-CO$_2$H

Carbonyl diimidazole (6.64 g, 40.94 mmol) was slowly added at room temperature to a solution of benzoic acid (5.00 g, 40.94 mmol) in THF (100 ml). When the effervescence had ceased, the reaction was heated to 60° C. for 4 hours to ensure complete formation of the imidazolide. The reaction was cooled to room temperature and a solution of 3,5-dihyroxy benzoic acid (3.15 g, 20.47 mmol) in THF (20 ml) was added dropwise. KOH (0.1 g, 1.80 mmol) was added and the mixture was heated to 60° C. for a further 4 hours. The resulting solution was concentrated in vacuo and the residue was dissolved in dichloromethane, washed with water, dried (MgSO$_4$), filtered and concentrated in vacuo to give the product (BA-DHBA-CO$_2$H) as a yellow/brown solid. BA-DHBA-CO$_2$H (2.44 g, 6.73 mmol) was dissolved in THF (100 ml). Carbonyl diimidazole (1.09 g, 6.73 mmol) was slowly added at room temperature. After full addition, the reaction was heated to 60° C. for 4 hours. The reaction was cooled to room temperature and a solution of 3,5-dihydroxy benzoic acid (0.41 g, 3.36 mmol) in THF (10 ml) was added dropwise. KOH (0.05 g, 0.90 mmol) was added and the mixture was heated to 60° C. for a further 4 hours. The resulting solution was concentrated in vacuo and the residue was dissolved in dichloromethane, washed with water, dried (MgSO$_4$), filtered and concentrated in vacuo to give the product (BA-DHBA-DHBA-CO$_2$H) as a yellow/brown solid.

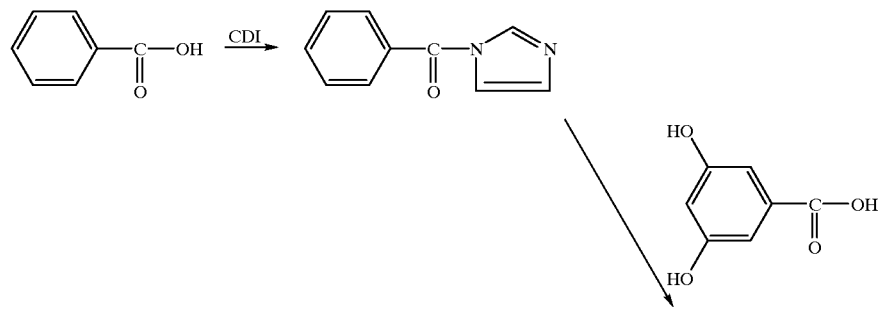

-continued

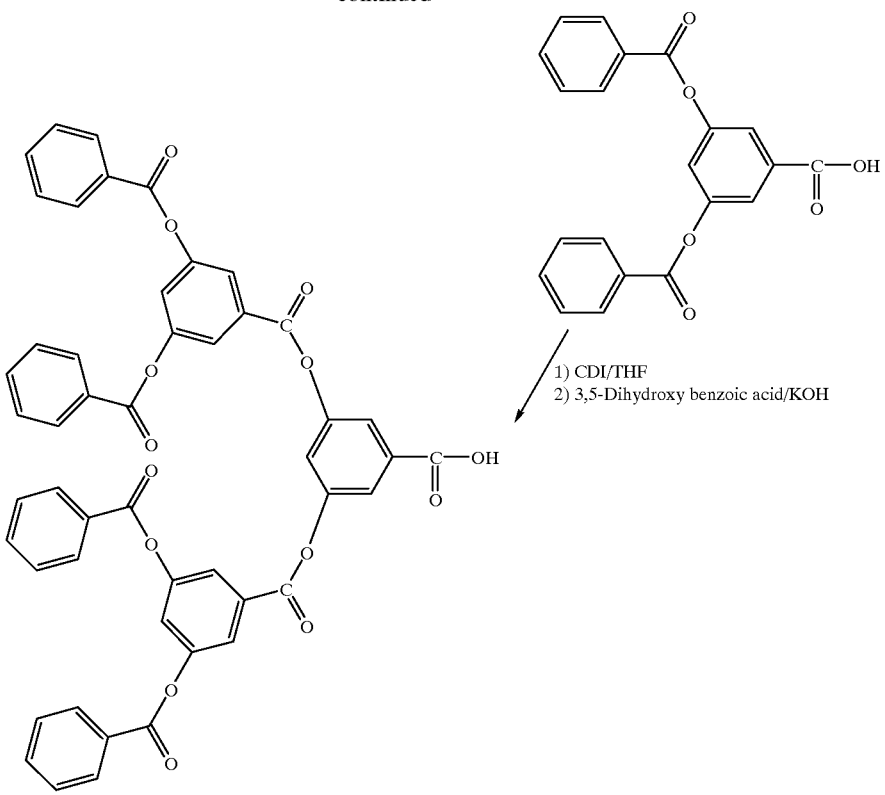

1) CDI/THF
2) 3,5-Dihydroxy benzoic acid/KOH

EXAMPLE 33

Formation of CIH-AEAE-SAn-AEAE-NH

A solution of CIH (5.88 g, 24.67 mmol) and 2-(2-Aminoethylamino) ethanol (1.28 g, 12.30 mmol) in THF (100 ml) was heated to 60° C. with KOH (0.10 g, 1.80 mmol) for 6 hours. The resulting solution was filtered and concentrated in vacuo. The residue was dissolved in dichloromethane, washed with water, dried ($MgSO_4$), filtered and concentrated in vacuo to give the product (CIH-AEAE-NH) as a clear colourless liquid. Succinic anhydride (6.75 g, 6.75 mmol) was added slowly to a solution of CIH-AEAE-NH (3.00 g, 6.75 mmol) in THF (50 ml) at room temperature and allowed to stir for 5 hours. Carbonyl diimidazole (1.09 g, 6.75 mmol) was added slowly to the solution. After complete addition, the reaction was heated to 60° C. and AEAE (0.35 g, 3.37 mmol) and KOH (0.05 g, 0.90 mmol) were added and reaction was stirred for a further 4 hours. The resulting solution was concentrated in vacuo and the residue was dissolved in dichloromethane, washed with water, dried ($MgSO_4$), filtered and concentrated in vacuo to give the product (CIH-AEAE-SAn-AEAE-NH) as a yellow liquid.

85 86
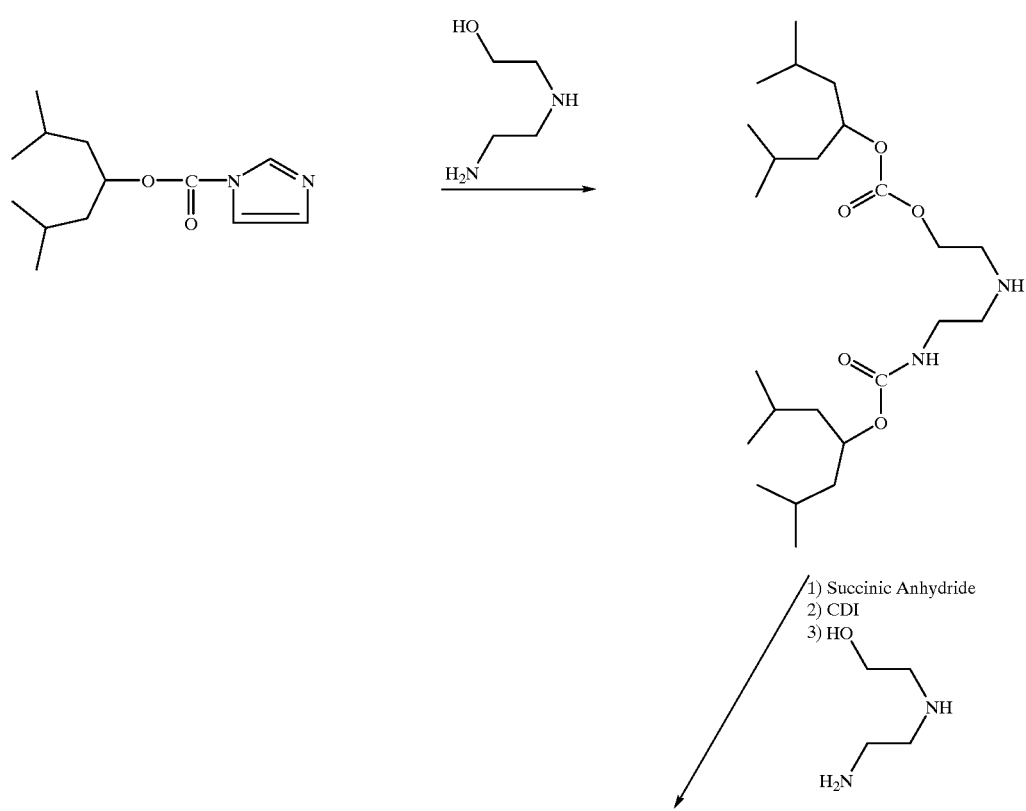
1) Succinic Anhydride
2) CDI
3) HO⌒NH⌒H₂N

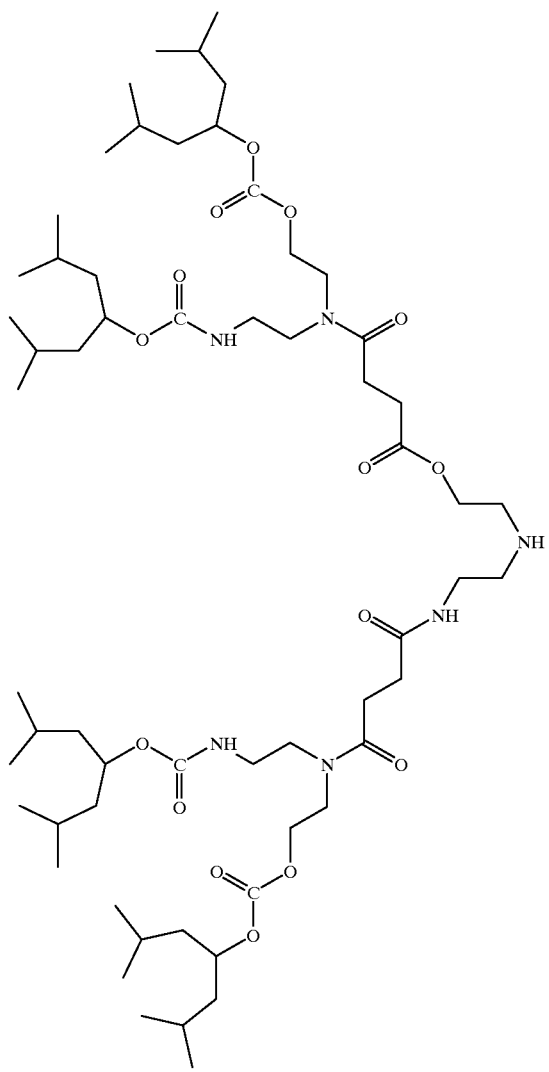

EXAMPLE 34

Formation or a Thiol Tipped Polyether Amine

Carbonyl diimidazole (2.00 g, 12.30 mmol) was added to a solution of mercaptoacetic acid (1.14 g, 2.30 mmol) in methanol (50 ml) at 0° C. After the effervescence had ceased, the solution was stirred at room temperature for a further 4 hours. A solution of 4,9-dioxa-1,12-dodecanediamine (1.26 g, 6.16 mmol) in methanol (10 ml) was added dropwise to the solution and the mixture was left to stir at room temperature for 1 hour. The reaction was heated to 60° C. for a further 2.5 hours and then left to cool. The resulting solution was concentrated in vacuo and the residue was dissolved in dichloromethane, washed with water, dried (MgSO$_4$), filtered and concentrated in vacuo to give the product as a yellow liquid

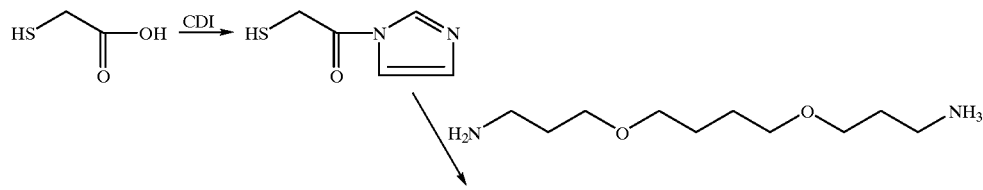

-continued

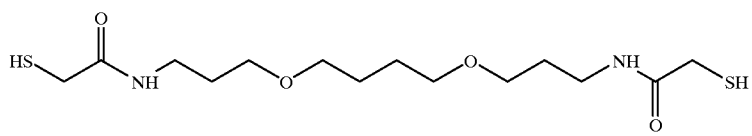

EXAMPLE 35

Formation of THAM-SAn-TAEA

A solution of trihydroxymethylaminomethane (19.90 g, 0.16 mol) and succinic anhydride (16.44 g, 0.16 mol) in methanol (so ml) was stirred at room temperature or 20 hours. Carbonyl diimidazole (26.64 g, 0.16 mol) was added to the reaction and stirred at room temperature for 2 hours. Tris (aminoethyl) amine (8.00 g, 0.055 mol) was added and the reaction mixture stirred at room temperature or 20 hours. The reaction mixture as concentrated in vacuo to give the crude product (still containing imidazole) as a yellow viscous liquid.

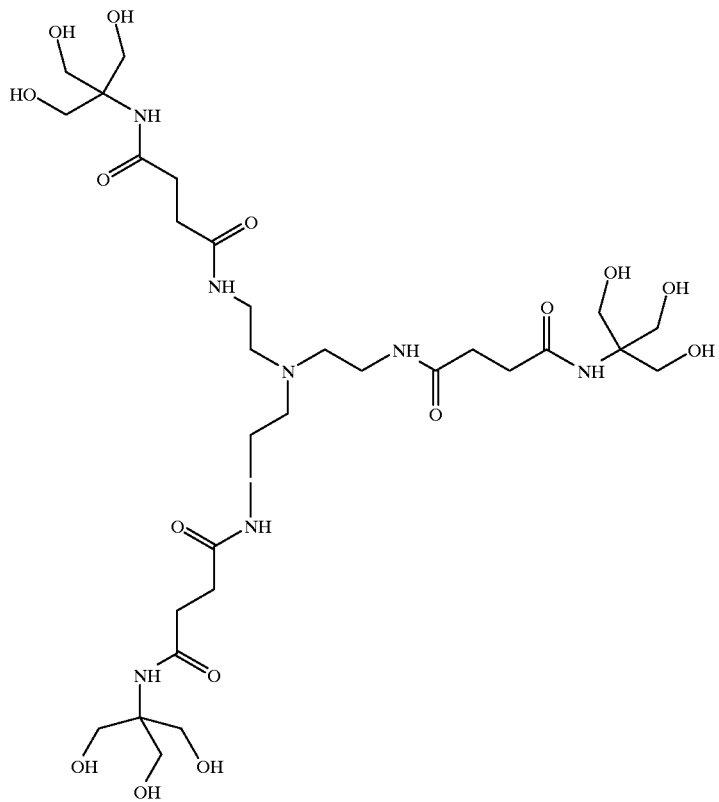

EXAMPLE 36

(a) Formation of DTA-SAn-DTA-NH

A sample of dendrimer wedge CIB-DTA-SAn-DTA-NH prepared in example 30 (1 g, 1.1 mmol) and trifluoroacetic acid (0.13 g, 1.1 mmol) in dichloromethane (30 ml) was stirred at room temperature for 4 hours then concentrated in vacuo to give the product.

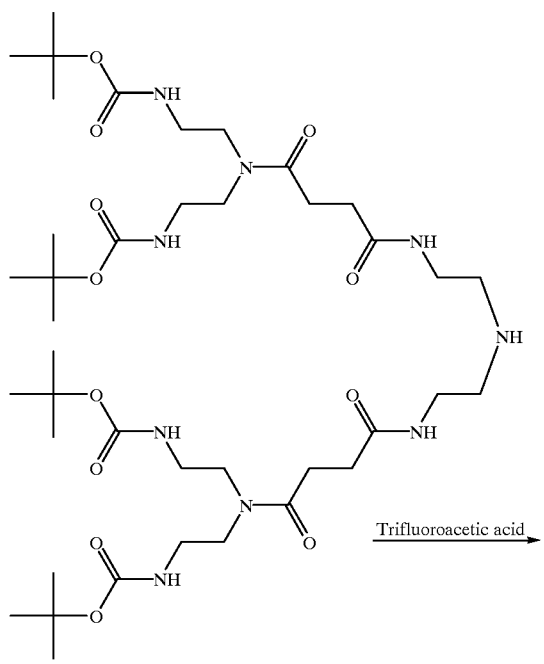
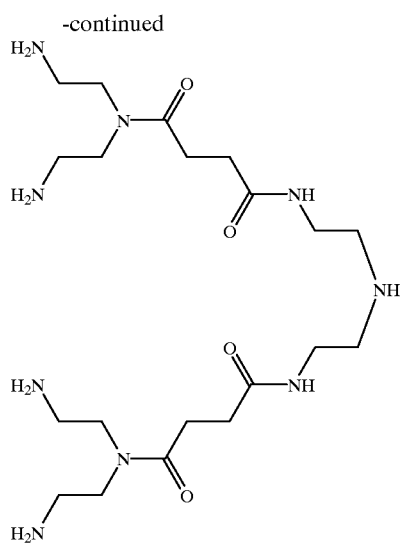

(b) Accelerated Synthesis—Formation of DPA-SAn-DTA-SAn-DTA-NH dendrimer wedge

Dipropylamine (1.00 g, 9.9 mmol) and succinic anhydride (0.99 g, 9.9 mmol) in methanol (30 ml) were stirred at room temperature for 24 hours. Carbonyl diimidazole (1.60 g, 0.99 mmol) was added and the reaction stirred at room temperature For 6 hours. Dendrimer wedge DTA-SAn-DTA-NH (1.17 g, 2.48 mmol) was added and the reaction mixture heated to 60° C. for 6 hours and cooled then concentrated in vacuo. The residue was dissolved in dichloromethane, washed with water, dried (MgSO$_4$), filtered and concentrated in vacuo to give the product.

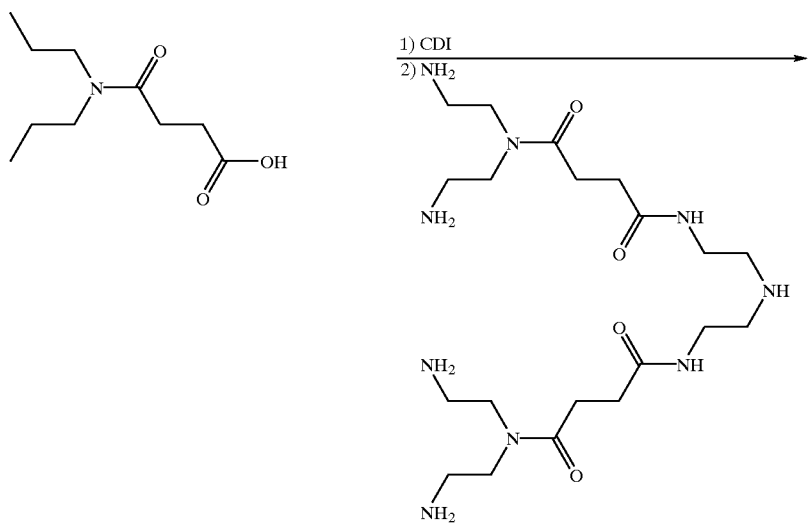

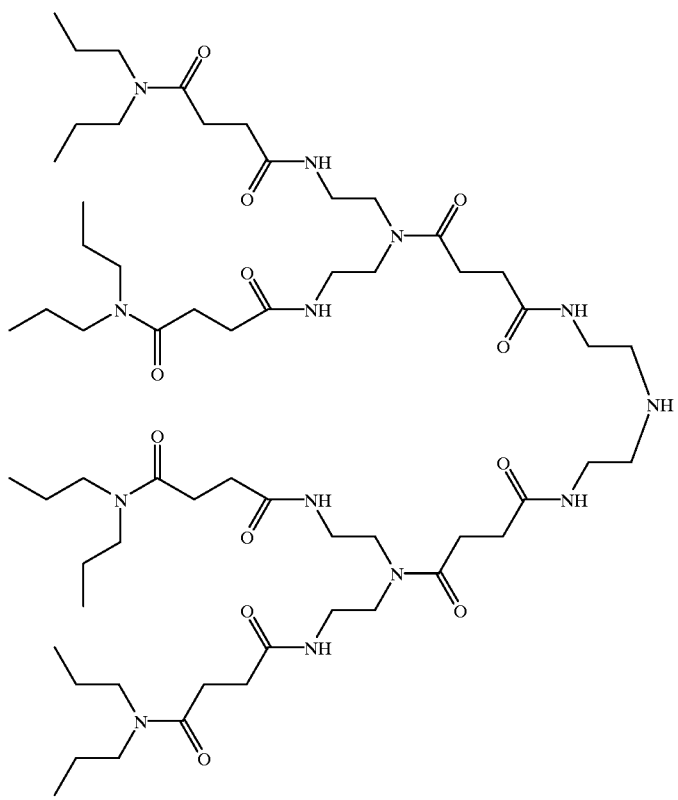

EXAMPLE 37

Formation of BEHA-TPA

A solution of terephthalic Acid (1.03 g, 6.2 mmol) in THF 150 ml) was heated to 60° C. Carbonyl diimidazole (2 g, 12.3 mmol) was added and the reaction mixture heated at 60° C. for 3 hours. Bisethylhexylamine (2.98 g, 12.3 mmol) was added and the reaction heated to 60° C. for 3 hours than concentrated in vacuo. The residue was dissolved in toluene and the imidazole removed by filtration. The filtrate was concentrated in vacuo to give the product as a colourless liquid.

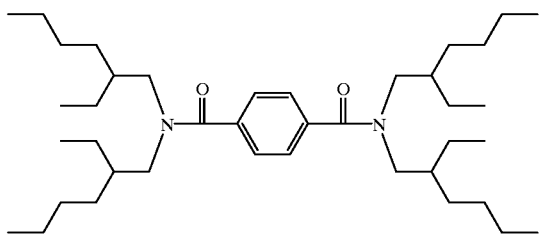

The bis(imidazolide) of Terephthalic acid can be reacted similarly with secondary amine-functional dendritic wedges such as those produced in Example 30 or 36.

EXAMPLE 38

Selective Coupling Reaction: Formation of BEHA-SAn-AEAE-CIB

A solution of bisethylhexylamine (3.00 g, 12.4 mmol) and succinic anhydride (1.24 g, 12.4 mmol) in toluene (50 ml) was stirred at room temperature for 6 hours. Carbonyl diimidazole (2.01 g, 12.4 mmol) was added and the reaction stirred at room temperature for 16 hours. Aminoethylaminoethanol (1.29 g, 12.4 mmol) was added and stirred at room temperature for 6 hours. CIB (2.09 g, 12.4 mmol) and potassium hydroxide (0.1 g, 1.2 mmol) was added and the reaction heated at 60° C. for 6 hours and concentrated in vacuo. The residue was dissolved in toluene, washed with water, dried $MgSO_4$ filtered and concentrated in vacuo to give the product as a pale yellow liquid.

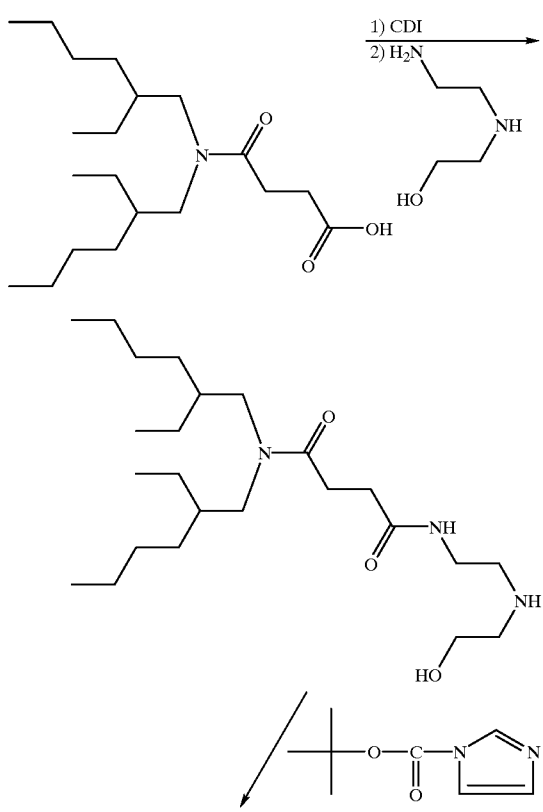
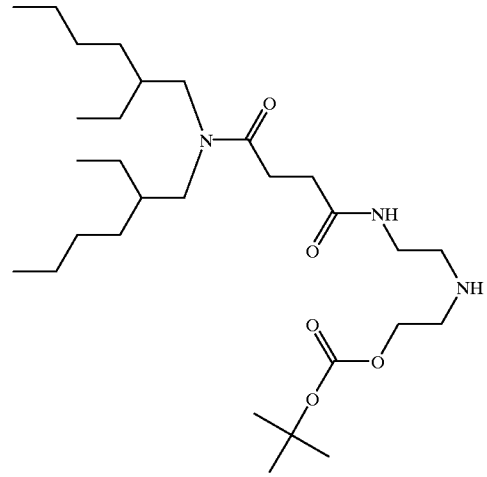

EXAMPLE 39
Formation of a Thiol Tipped Dendrimer: MAA-DTA-SAn-TAEA

A solution of mercaptoacetic acid (14.46 g, 0.16 mol), carbonyl diimidazole (25.47 g, 0.16 mol) in methanol (50 ml) was stirred at 0° C. for 6 hours. Diethylene triamine (8.10, g, 0.08 mol) was added and stirred at room temperature for 20 hours. The reaction mixture was concentrated in vacuo. The residue was extracted with hot ethyl, acetate to remove the imidazole and the remaining residue dried in vacuo. A solution of the residue (13.73 g, 0.05 mol) and succinic anhydride (5.47 g, 0.05 mol) in methanol (50 ml) was stirred at room temperature for 24 hours. Carbonyl diimidazole (8.86 g, 0.05 mol) was added stirred at 0° C. for 6 hours. Tris(aminoethyl)amine (2.66 g, 18 mmol) was added and stirred at room temperature for 20 hours. The reaction mixture was concentrated in vacuo. The residue was extracted with hot ethyl acetate to remove the imidazole and the remaining yellow oil dried in vacuo to give the product (18.03 g, 60%).

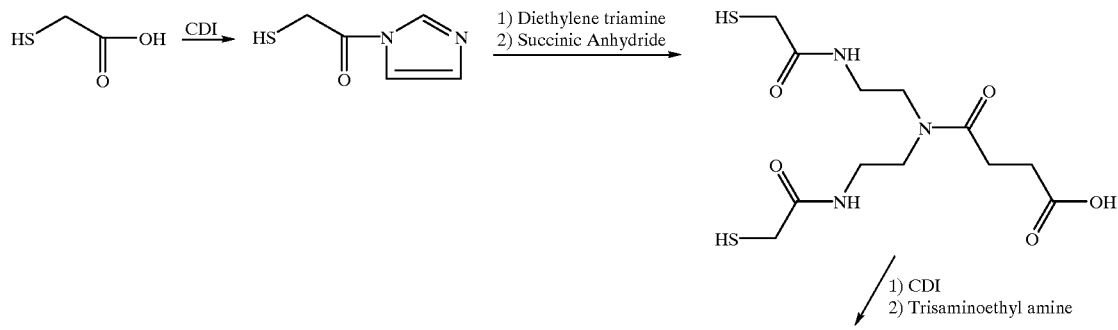

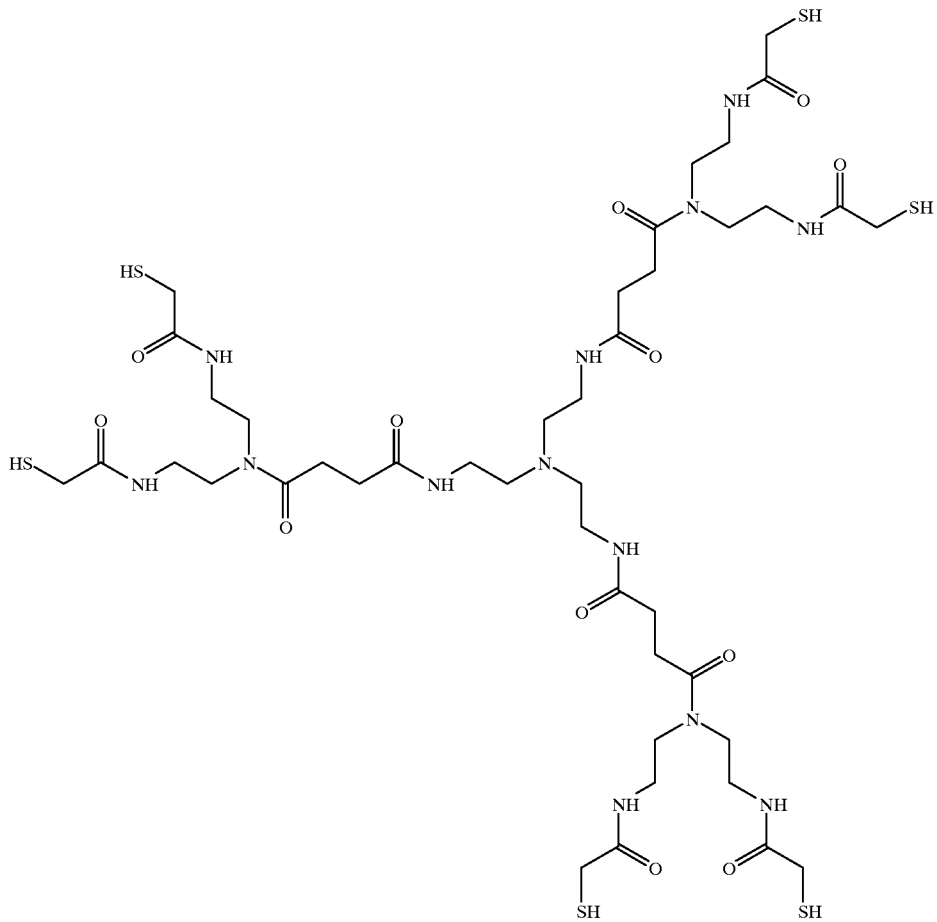

EXAMPLE 40

Formation of a Dendrimer with a Controlled Number of Functional Groups

A solution of CIB (10.0 g, 59.0 mmol) and 2-(propylamino) ethanol (6.13 g, 59.0 mmol) in THF (100 ml) was heated to 60° C. with KOH (0.30 g, 5.40 mmol) for 6 hours. The resulting solution was filtered and concentrated in vacuo. The residue was dissolved in dichloromethane, washed with water, dried (MgSO$_4$), filtered and concentrated in vacuo to give the product (CIB-PAE-NH) as a clear colourless liquid. Succinic anhydride (4.93 g, 49.0 mmol) was added slowly to a solution of CIB-PAE-NH (10.0 g, 49.0 mmol) in THF (100 ml) at room temperature and allowed to stir for 5 hours. Carbonyl diimidazole (7.98 g, 49.0 mmol) was added slowly to the solution. After complete addition, the reaction was heated to 60° C. and AEAE (5.12 g, 49.0 mmol) and KOH (0.30 g, 5.40 mmol) were added and reaction was stirred for a further 4 hours. A solution of an acid imidazolide (12.36 g, 49.0 mmol) (derived from the reaction of dipropyl amine, succinic anhydride and CDI) in THF (50 ml) was added dropwise to the reaction in the presence of KOH (0.30 g, 5.40 mmol). The resulting solution was filtered and concentrated in vacuo. The residue was dissolved in dichloromethane, washed with water, dried (MgSO$_4$), filtered and concentrated in vacuo to give an amide wedge with one protected OH group. Succinic anhydride (3.50 g, 35.0 mmol) was added to a solution of the wedge (20 g, 35.0 mmol) in THF (100 ml) and allowed to stri at room temperature for 5 hours. Carbonyl diimidazole (5.66 g, 35.0 mmol) was added slowly to the solution. After complete addition, the reaction was heated to 60° C. and TAEA (1.70 g, 11.6 mmol) was added and stirred for a further 4 hours at 60° C. The resulting solution was filtered and concentrated in vacuo. The residue was dissolved in dichloromethane, washed with water, dried (MgSO$_4$), filtered and concentrated in vacuo to give the product as a brown gum. The product was heated at approximately 170° C. for 1 hour and cooled to give the the OH functional dendrimer.

99
100
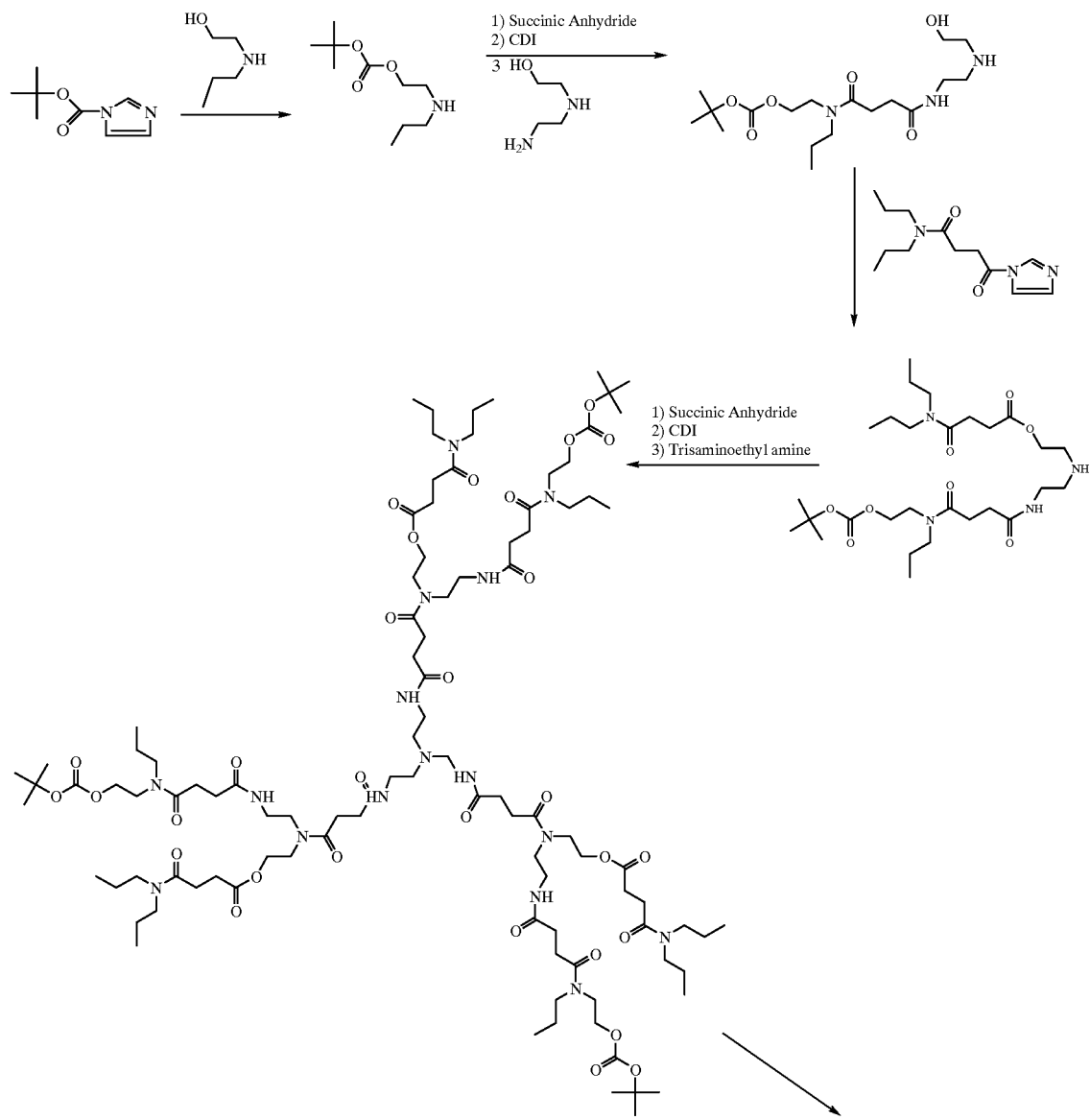

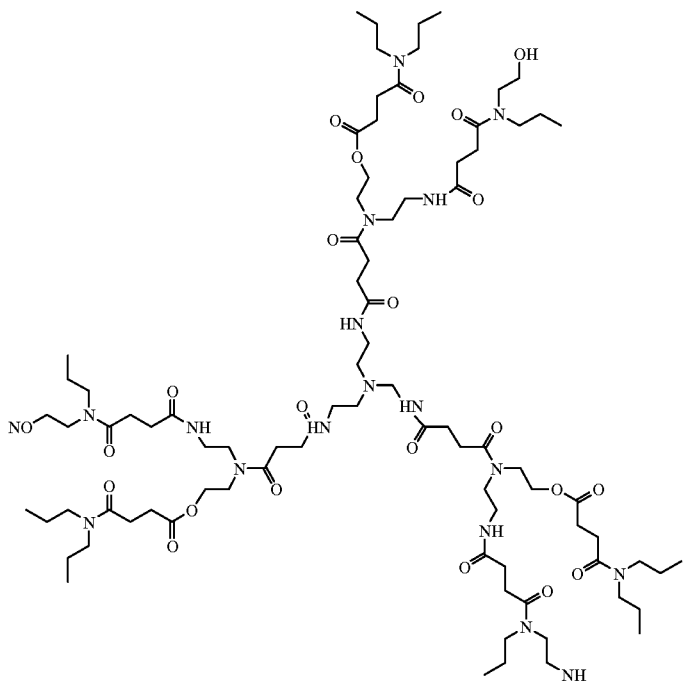

EXAMPLE 41

Formation of a Dendrimer with Reduced Functionality

A solution of tertiary butanol (44.4 g, 0.6 mol), carbonyl diimidazole (97.2 g, 0.6 mol) and potassium hydroxide (3.36 g, 0.06 mol) in toluene (300 ml) was heated at 60° C. for 6 hours. Diethyldiethylene triamine (95.4 g, 0.6 mol) was added and heated at 60° C. for 6 hours and cooled. The reaction mixture as filtered and concentrated in vacuo. The residue was dissolved in dichloromethane, washed with water, dried (MgSO$_4$), filtered and concentrated in vacuo to give the product. The residue was dissolved in toluene (300 ml), glutaric anhydride (68.4 g, 0.6 mol) was added and stirred at room temperature for 24 hours. Carbonyl diimidazole (97.2 gm 0.6 mol) was added and the reaction mixture stirred at room temperature for 6 hours. Tris (aminoethyl)amine (29.2 g, 0.2 mol) was added and the reaction mixture heated at 60° C. for 6 hours and cooled. The reaction mixture as filtered and concentrated in vacuo. The residue was dissolved in dichloromethane, washed with water, dried (MgSO$_4$) filtered and concentrated in vacuo to give the product as a brown liquid. A sample of dendrimer (0.91 g, 0.75 mmol) was heated at about 200° C. for 1 hour and cooled to give the product as a brown gum.

What is claimed is:

1. A process for the preparation of a compound or polymer having at least one functional group selected from hydroxyl, thiol, amino and carboxylic acid groups, characterised in which process a compound or polymer (A) comprising a group of the formula:

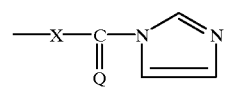

(I)

where Q represents O or S and X represents —O—, —S—, —NH— or a direct bond, the group being linked to the remainder of the compound or polymer through a carbon atom, is reacted with a compound (B) comprising at least two functional groups selected from hydroxyl, thiol, amino and carboxylic acid groups, one of which functional groups (II) reacts with the group of formula (I) and one of which functional groups (III) is substantially unreactive with the group of Formula (I) under the conditions of reaction, so that the compound (B) becomes bonded to (A) through the reaction of groups (I) and (II) forming a compound or polymer containing unreacted functional groups (III).

2. A process according to claim 1 for the preparation of a substituted amide, in which process a compound or polymer (A) of the formula:

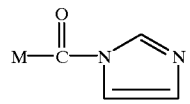

derived from an aliphatic carboxylic acid MCOOH in which M is an aliphatic group is reacted with a compound (B) comprising at least one primary amine group and at least one substituent selected from alcohol, thiol, carboxylic acid and secondary amine groups to produce the substituted amide.

3. A process according to claim 1 for the preparation of a substituted amide, in which process a compound or polymer (A) of the formula:

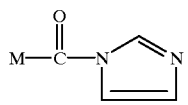

derived from an aromatic carboxylic acid MCOOCH in which M is a phenyl, substituted phenyl, benzyl or substituted benzyl group is reacted with a compound (B) containing at least one amine group and at least one substituent selected from alcohol, thiol and carboxylic acid groups to produce the substituted amide.

4. A process according to claim 1 for the preparation of a substituted ester, in which process a compound or polymer (A) of the formula:

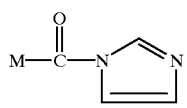

derived from a carboxylic acid MCOOH is reacted with a compound (B) comprising at least one primary or secondary hydroxyl group and at least one substituent selected from tertiary alcohol and carboxylic acid groups in the presence of a base to produce the substituted ester.

5. A process according to claim 1 for the preparation of a substituted urethane, in which process a compound or polymer (A) of the formula:

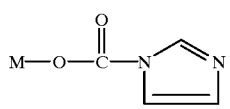

derived from a secondary or tertiary aliphatic alcohol MOH where M is a secondary or tertiary aliphatic group containing at least 4 carbon atoms is reacted with a compound (B) comprising at least one primary amine group and at least one substituent selected from alcohol, thiol, carboxylic acid and secondary amine groups to produce the substituted urethane.

6. A process according to claim 1 for the preparation of a substituted urethane, in which process a compound or polymer (A) of the formula:

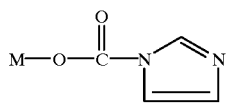

derived from a primary alcohol MOH is reacted with a compound (B) comprising at least one amine group and at least one substituent selected from alcohol, thiol and carboxylic acid groups to produce the substituted urethane.

7. A process according to claim 1 for the preparation of a substituted organic carbonate, in which process a compound or polymer (A) of the formula:

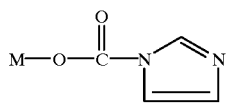

derived from an aliphatic alcohol MOH is reacted with a compound (B) comprising at least one primary alcohol group and at least one substituent selected from secondary or tertiary alcohol, thiol and carboxylic acid groups in the presence of a basic catalyst to produce the substituted carbonate.

8. A process according to claim 1 for the preparation of a branched compound or polymer containing at least two linkages selected from carbonate, urethane, urea, amide and ester linkages, in which process the compound (B) contains at least two functional groups (II) which are reactive with the group of formula (I).

9. A process according to claim 8, wherein the said branched compound or polymer is further reacted with carbonyl diimidazole or thiocarbonyl diimidazole to produce a branched compound or polymer of the formula:

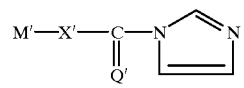

(IV)

where Q' represents O or S, X' represents —O—, —S—, —NH— or a direct bond and M' represents a branched organic radical formed by the reaction of compound or polymer (A) and compound (B).

10. A process according to claim 9, wherein the branched compound or polymer of formula (IV) is further reacted with a compound or polymer (C) comprising at least two groups reactive with the group of formula:

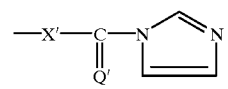

thereby forming a dendritic polymer comprising at least two of the branched organic radicals M' by convergent growth.

11. A process according to claim 10 for forming a dendritic polymer comprising a functional group selected from hydroxyl, thiol, amino and carboxylic acid groups, in which process the compound or polymer (C) additionally contains a functional group selected from hydroxyl, thiol, amino and carboxylic acid groups which is substantially unreactive with the group of formula:

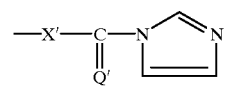

12. A process according to claim 11, wherein the said dendritic polymer is further reacted with carbonyl diimidazole or thiocarbonyl diimidazole to produce a dendrite polymer (D) in which the said functional group is converted to a group of the formula:

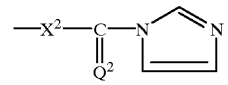

where $Q^2$ represents O or S and $X^2$ represents —O—, —S—, —NH— or a direct bond.

13. A process according to claim 12, wherein the dendritic polymer (D) is further reacted with a compound or polymer (E) comprising at least two groups reactive with the group of formula:

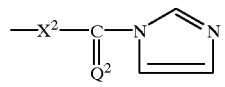

thereby forming a dendritic polymer containing an increased number of branches.

14. A process according to claim 10 wherein the compound or polymer (C) or (E) containing at least two reactive groups is a polymer in which said reactive groups are present as chain-terminating groups, whereby a polymer capped with at least two dendritic structures is produced.

15. A process according to claim 9 wherein successive reactions are carried out in the same aromatic hydrocarbon solvent with removal of imidazole by-product and/or excess carbonyl diimidazole by cooling and separating the precipitated imidazole and/or carbonyl diimidazole but without isolation of the reaction product.

16. A process according to claim 2, wherein the compound (B) contains two primary amine groups and one secondary amine group and the substituted amide formed, which contains two amide linkages and a secondary amine group, is further reacted with a cyclic carboxylic acid anhydride to form a carboxylic acid-substituted alkyl amide group on the secondary amine group and then with carbonyl diimidazole followed by a compound comprising at least two primary amine groups to produce a dendritic polyamide.

17. A process according to claim 1, for the preparation of a compound or polymer having at least two functional groups selected from hydroxyl, thiol, amino and carboxylic acid groups, in which process the compound (B) comprises at least two functional groups (III) which are substantially unreactive with the group of formula (I).

18. A process for the preparation of a substituted amide, characterised in that a compound comprising an aliphatic carboxylic acid group and at least one substituent selected from alcohol and thiol groups is reacted with carbonyl diimidazole to convert the carboxylic acid group to a group of the formula:

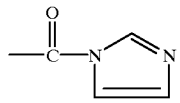

and the resulting compound (A') is reacted with a compound or polymer (B') comprising at least one primary amine group to produce the substituted amide.

19. A process according to claim 18, for the preparation of a compound or polymer comprising at least two functional groups selected from alcohol or thiol groups, in which process the compound or polymer (B') contains at least two primary amine groups.

20. A process according to claim 19, wherein the compound or polymer having at least two functional groups is further reacted with carbonyl diimidazole or thiocarbonyl diimidazole to produce a compound or polymer of the formula:

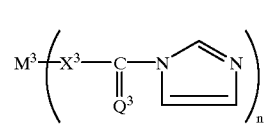

where $Q^3$ represents O or S, $X^3$ represents —O—, —S—, —NH— or a direct bond, $M^3$ represents an organic radical formed either by the reaction of compound or polymer (A) with compound (B) or by the reaction or compound (A') with compound or polymer (B') and n is an integer of at least 2 corresponding to the number of functional groups (III) in compound (B) or the number of primary amine groups in compound or polymer (B').

21. A process according to claim 20, wherein the compound or polymer (V) is reacted with a compound (F) having at least one functional group selected from hydroxyl, thiol and amino groups which is reactive with the group of formula:

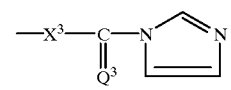

thereby forming a branched molecule having a linkage, selected from carbonate, urethane, urea, amide and ester linkages, in each branch.

22. A process according to claim 21, wherein the compound (F) additionally comprises at least two functional groups selected from hydroxyl, thiol, amino and carboxylic acid groups which are substantially unreactive with the

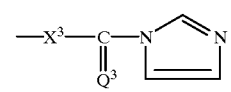

group but which are reactive with carbonyl diimidazole, and the said branched molecule is reacted with carbonyl diimidazole or thiocarbonyl diimidazole to form at least two

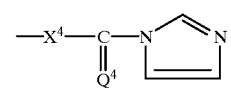

groups in each branch, where $Q^4$ represents O or S and $X^4$ represents —O—, —S—, —NH— or a direct bond, and is then reacted with a compound having at least one functional group selected from hydroxyl, thiol and amino groups which is reactive with the group of formula:

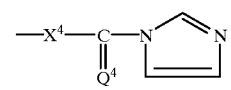

thereby forming a dendritic polymer by divergent growth.

23. A process according to claim 1, wherein the compound or polymer (B) comprises a functional group (III) which is capable of reaction with a group of formula (I) only under conditions of reaction different from the conditions of reaction, and in that the reaction product containing unreacted functional groups (III) is subsequently reacted with a compound or polymer (A') which contains a group of the formula (I) but is different from the compound or polymer (A).